United States Patent
Wang et al.

(10) Patent No.: US 11,407,717 B2
(45) Date of Patent: Aug. 9, 2022

(54) BENZIMIDAZOLE DERIVATIVES AND USE THEREOF AS IDH1 INHIBITORS

(71) Applicant: KPC PHARMACEUTICALS, INC., Yunnan (CN)

(72) Inventors: Dahai Wang, Shanghai (CN); Wenyuan Qian, Shanghai (CN); Shilan Liu, Shanghai (CN); Shuhui Chen, Shanghai (CN)

(73) Assignee: KPC PHARMACEUTICALS, INC., Yunnan (CN)

( * ) Notice: Subject to any disclaimer, the term of this patent is extended or adjusted under 35 U.S.C. 154(b) by 0 days.

(21) Appl. No.: 17/254,890

(22) PCT Filed: Jun. 26, 2019

(86) PCT No.: PCT/CN2019/092997
§ 371 (c)(1),
(2) Date: Dec. 22, 2020

(87) PCT Pub. No.: WO2020/001474
PCT Pub. Date: Jan. 2, 2020

(65) Prior Publication Data
US 2021/0206728 A1     Jul. 8, 2021

(30) Foreign Application Priority Data
Jun. 26, 2018  (CN) .......................... 201810672394.3

(51) Int. Cl.
*C07D 235/30*     (2006.01)
(52) U.S. Cl.
CPC .................. *C07D 235/30* (2013.01)
(58) Field of Classification Search
CPC .................................................. C07D 235/30
See application file for complete search history.

(56) References Cited

U.S. PATENT DOCUMENTS

| | | | | |
|---|---|---|---|---|
| 2007/0105930 A1* | 5/2007 | Parmee | ................ | C07D 235/30 514/394 |
| 2014/0235620 A1 | 8/2014 | Caferro et al. | | |
| 2017/0107194 A1 | 4/2017 | Konteatis et al. | | |
| 2018/0118759 A1 | 5/2018 | Bauer et al. | | |
| 2018/0222871 A1 | 8/2018 | Schirmer et al. | | |
| 2019/0161473 A1 | 5/2019 | Wang et al. | | |

FOREIGN PATENT DOCUMENTS

| | | |
|---|---|---|
| CN | 103958506 | 7/2014 |
| CN | 107641114 | 1/2018 |
| CN | 107848985 | 3/2018 |
| CN | 107849059 | 3/2018 |
| WO | WO 2015/121209 | 8/2015 |
| WO | WO 2016/171756 | 10/2016 |
| WO | WO 2017/009325 | 1/2017 |
| WO | WO 2017/012967 | 1/2017 |
| WO | WO 2018/010637 | 1/2018 |
| WO | WO 2018/071404 | 4/2018 |

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Dang et al., "Cancer-associated IDH1 mutations produce 2-hydroxyglutarate," *Nature*, 462(7274):739, 18 pages, 2009.
English translation of International Search Report issued in International Patent Application No. PCT/CN2019/092997, dated Oct. 8, 2019.
Hartmann et al., "Type and frequency of IDH1 and IDH2 mutations are related to astrocytic and oligodendroglial differentiation and age: a study of 1,010 diffuse gliomas," *Acta Neuropathol.*, 118:469-474, 2009.
Pusch et al., "Pan-mutant IDH1 inhibitor BAY 1436032 for effective treatment of IDH1 mutant astrocytoma in vivo," *Acta Neuropathol.*, 133(4):629-644, 2017.

* cited by examiner

*Primary Examiner* — Shawquia Jackson
(74) *Attorney, Agent, or Firm* — Parker Highlander PLLC

(57) ABSTRACT

The present invention relates to benzimidazole compounds and an application thereof as IDH1 mutant inhibitors, in particular, to a compound as represented by formula (I), tautomers thereof, or pharmaceutically acceptable salts thereof.

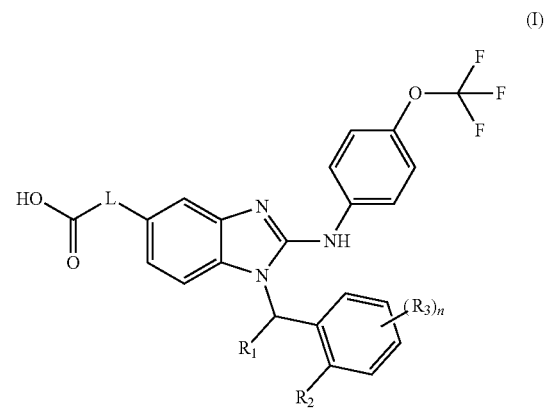

16 Claims, No Drawings

BENZIMIDAZOLE DERIVATIVES AND USE THEREOF AS IDH1 INHIBITORS

CROSS REFERENCE TO RELATED APPLICATIONS

This application is a national phase application under 35 U.S.C. § 371 of International Application No. PCT/CN2019/092997, filed Jun. 26, 2019, which claims the priority of Chinese Patent Application No. CN201810672394.3 filed on Jun. 26, 2018. The entire contents of each aforementioned disclosure are incorporated herein by reference.

FIELD

The present disclosure relates to a series of benzimidazole compounds and an application thereof as IDH1 mutant inhibitors, in particular, to a compound as represented by formula (I), a tautomer thereof, or a pharmaceutically acceptable salt thereof.

BACKGROUND

Isocitrate dehydrogenase is an important enzyme in the citric acid cycle, and catalyzes the oxidative decarboxylation of isocitrate to 2-oxoglutarate (i.e. 2-α-ketoglutarate, α-KG). The protein encoded by the IDH1 gene is NADP(+)-dependent isocitrate dehydrogenase comprising a PTS-1 peroxidase targeting signal sequence found in the cytoplasm and peroxisomes. The presence of this enzyme in peroxisomes suggests a role for internal NADPH regeneration.

Non-mutant enzyme, such as wild-type IDH, catalyzes the oxidative decarboxylation of isocitrate while reducing $NAD^+(NADP^+)$ to NADP (NADPH):

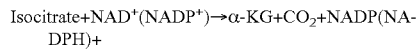

IDH 1/2 mutant protein (IDH 1/2 m) has been found in a variety of tumors, including glioma, acute myeloid leukemia (AML), chondrosarcoma, intrahepatic cholangioma, melanoma, prostate cancer, angioimmunoblastic T cell lymphoma. In gliomas, more than 70% of non-primary glioblastomas have IDH1 mutations, and 92.7% of IDH1 mutant tumors have arginine replaced by histidine (i.e. IDH1 R132H) (Hartmann C, Acta Neuropathol. 2009 October; 1 18(4):469-74).

The IDH mutant protein has a new function, that is, it catalyzes the reduction of α-KG to produce a carcinogenic metabolite 2-hydroxyglutarate (2-HG). The production of 2-HG is believed to contribute to the formation and development of cancer (Dang L, Nature, 2009 Dec. 10; 462 (7274):739-44). Normal cells produce very low levels of 2-HG, but cells with IDH mutations are able to produce high levels of 2-HG. High levels of 2-HG can also be found in tumors with IDH mutations.

Therefore, the inhibition of mutant IDH and the new activity thereof is a potential method for cancer treatment. Therefore, there is a need to obtain inhibitors of IDH mutants to inhibit the production of 2-HG.

Acta Neuropathol (2017, Vol(133), Issue 4, 629-644) discloses the specific structure of compound BAY1436032.

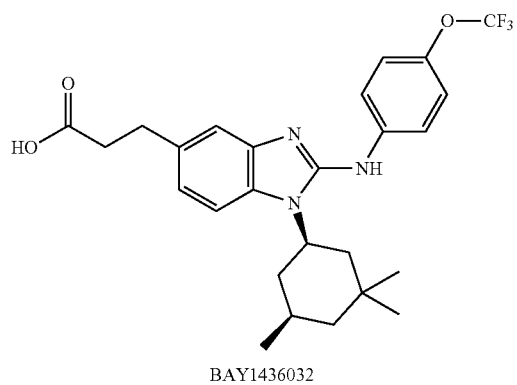

BAY1436032

SUMMARY

The present disclosure provides a compound as shown in formula (I),

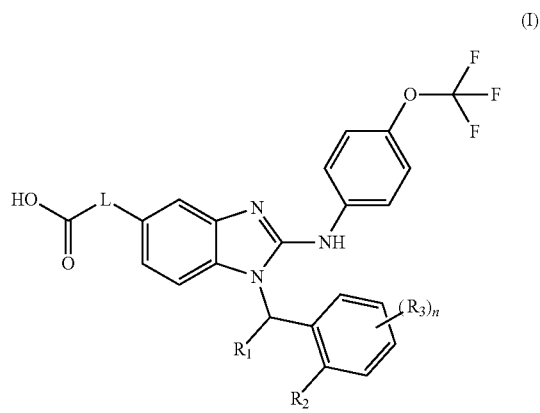

(I)

wherein $R_1$ is selected from $C_{1-6}$ alkyl, $C_{3-6}$ cycloalkyl and phenyl, the $C_{1-6}$ alkyl, $C_{3-6}$ cycloalkyl and phenyl being optionally substituted with 1, 2 or 3 $R_a$;

$R_2$ and $R_3$ are each independently selected from H, F, Cl, Br, I, OH, $NH_2$, CN, COOH, $C_{1-6}$ alkyl and $C_{1-6}$ alkoxy, the $C_{1-6}$ alkyl and $C_{1-6}$ alkoxy being optionally substituted with 1, 2 or 3 $R_b$;

alternatively, $R_1$ and $R_2$ are joined together to form a $C_{4-6}$ cycloalkenyl optionally substituted with 1, 2 or 3 $R_c$;

L is selected from —$CH_2CH_2$— and —$C_{3-6}$ cycloalkyl-$CH_2$—;

n is selected from 1, 2 and 3; and $R_a$, $R_b$, and $R_c$ are each independently selected from F, Cl, Br, I, OH, $NH_2$, CN, COOH, and Me;

or an isomer thereof, or a pharmaceutically acceptable salt thereof.

In some embodiments of the present disclosure, the above-mentioned $R_1$ is selected from $C_{1-3}$ alkyl, cyclopropanyl and phenyl, the $C_{1-3}$ alkyl, cyclopropanyl and phenyl being optionally substituted with 1, 2 or 3 $R_a$, and other variables are as defined in the present disclosure.

In some embodiments of the present disclosure, the above-mentioned $R_1$ is selected from $CH_3$, $CH_2F$, $CHF_2$, $CF_3$, $CH_2CH_3$, $CH_2CF_3$, $CH_2CH_2CH_3$, $C(CH_3)_3$,

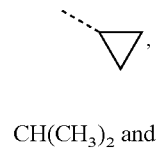

CH(CH$_3$)$_2$ and

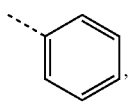

and other variables are as defined in the present disclosure.

In some embodiments of the present disclosure, the above-mentioned R$_2$ and R$_3$ are each independently selected from H, F, Cl, Br, I, OH, NH$_2$, CN, COOH, C$_{1-3}$ alkyl and C$_{1-3}$ alkoxy, the C$_{1-3}$ alkyl and C$_{1-3}$ alkoxy being optionally substituted with 1, 2 or 3 R$_b$, and other variables are as defined in the present disclosure.

In some embodiments of the present disclosure, the above-mentioned R$_2$ and R$_3$ are each independently selected from H, F, Cl, Br, I, OH, NH$_2$, CN, COOH, CH$_3$ and CH$_3$O, the CH$_3$ and CH$_3$O being optionally substituted with 1, 2 or 3 R$_b$, and other variables are as defined in the present disclosure.

In some embodiments of the present disclosure, the above-mentioned R$_2$ and R$_3$ are each independently selected from H, F, Cl, Br, I, OH, NH$_2$, CN, COOH, CH$_3$, CH$_2$F, CHF$_2$, CF$_3$ and OCH$_3$, and other variables are as defined in the present disclosure.

In some embodiments of the present disclosure, the above-mentioned L is selected from —CH$_2$CH$_2$— and

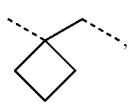

and other variables are as defined in the present disclosure.

In some embodiments of the present disclosure, the above structural unit

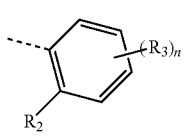

is selected from

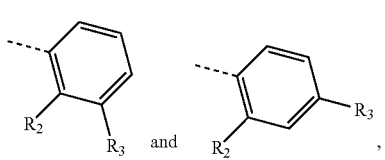

and other variables are as defined in the present disclosure.

In some embodiments of the present disclosure, the above structural unit

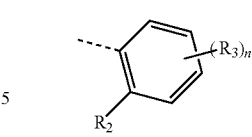

is selected from

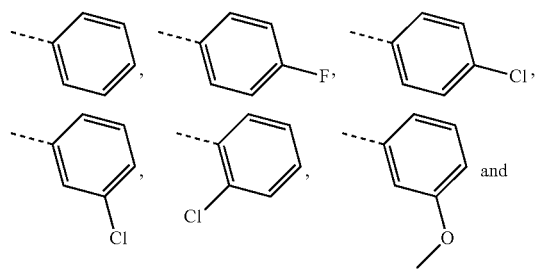

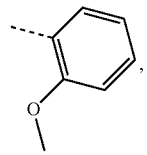

and other variables are as defined in the present disclosure.

In some embodiments of the present disclosure, the above structural unit

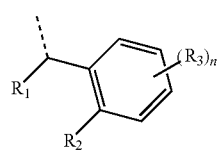

is selected from

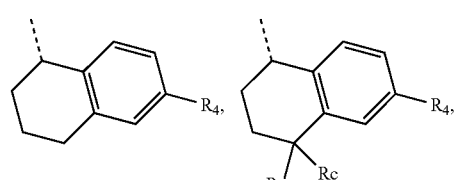

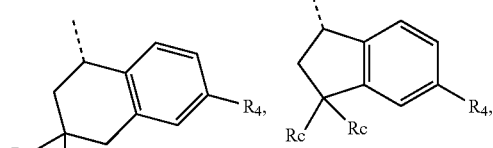

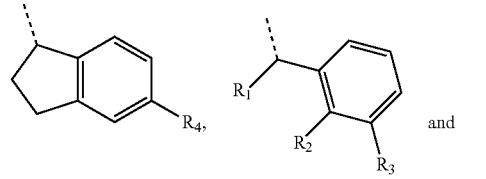

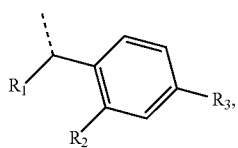

and other variables are as defined in the present disclosure.

In some embodiments of the present disclosure, the above structural unit

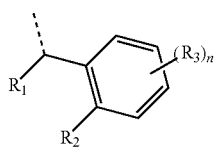

is selected from

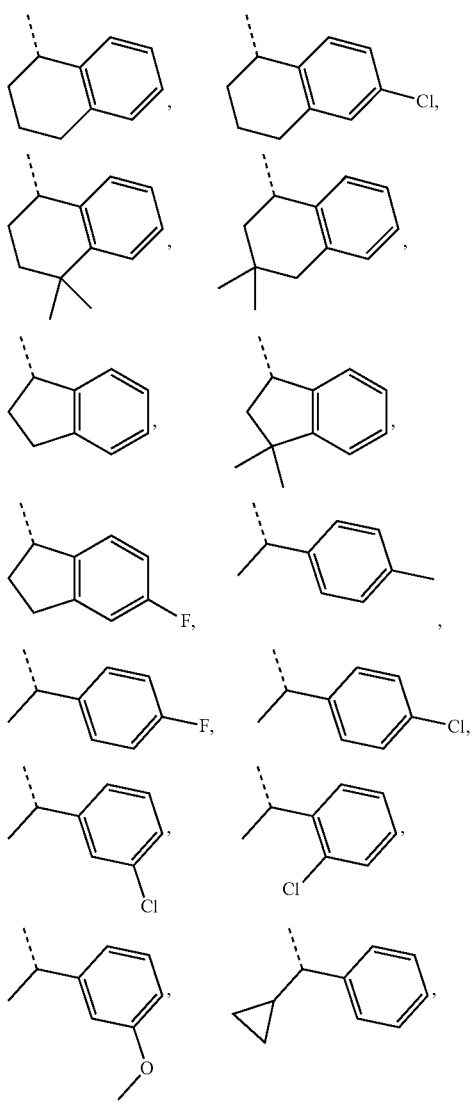

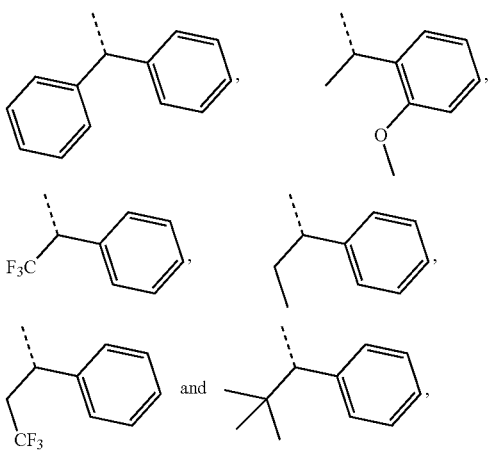

and other variables are as defined in the present disclosure.

There are also some embodiments of the present disclosure obtained from any combination of the above variables.

In some embodiments of the present disclosure, the above-mentioned compound, or an isomer thereof, or a pharmaceutically acceptable salt thereof is selected from

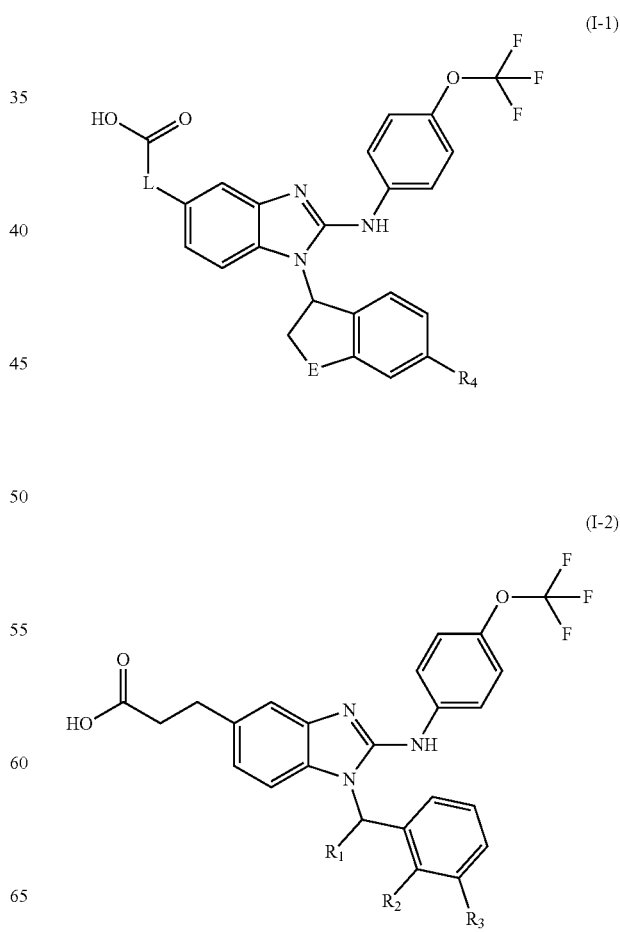

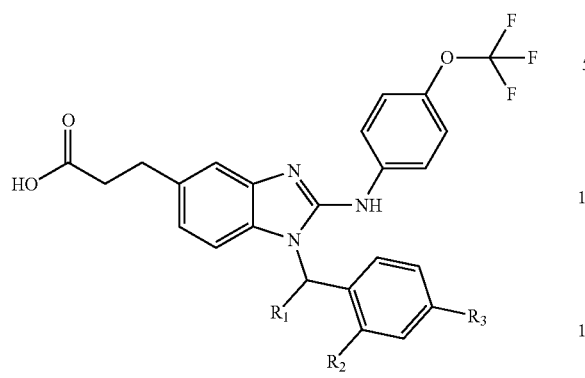
(I-3)
wherein
E is selected from —CH$_2$—, —CH$_2$CH$_2$—, —C(CH$_3$)$_2$— and —C(CH$_3$)$_2$CH$_2$—;
L is selected from —CH$_2$CH$_2$— and
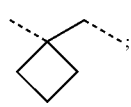
and
R$_1$, R$_2$ and R$_3$ are as defined in the present disclosure.
In some embodiments of the present disclosure, the above-mentioned compound, or an isomer thereof, or a pharmaceutically acceptable salt thereof is selected from
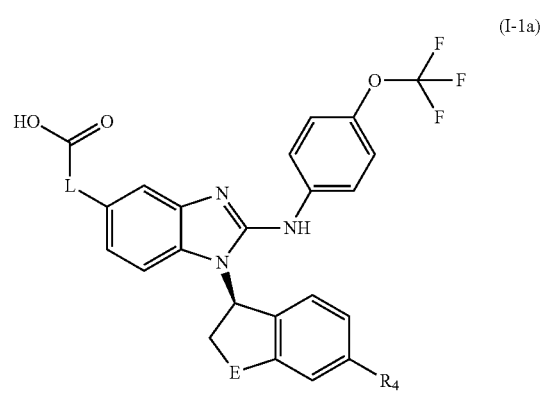
(I-1a)
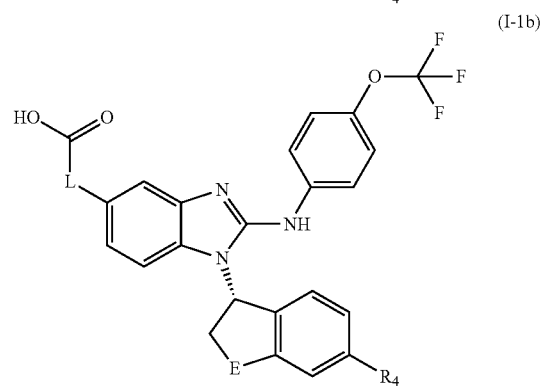
(I-1b)
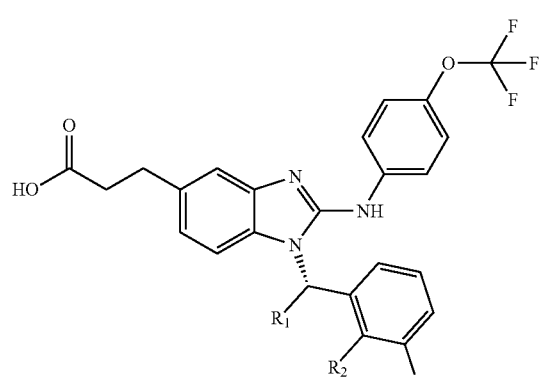
(I-2a)
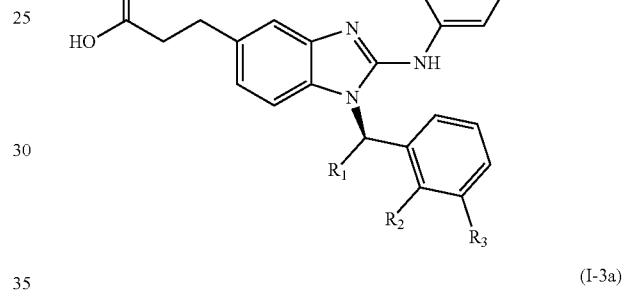
(I-2b)
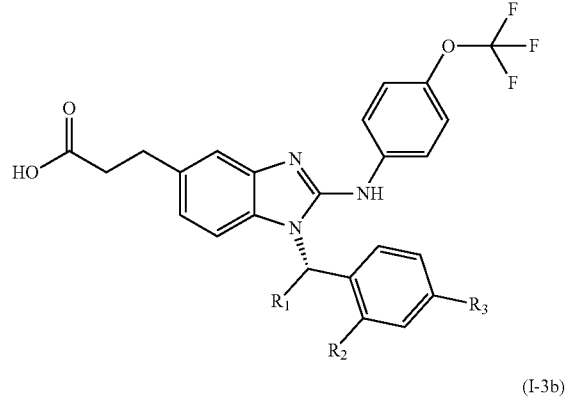
(I-3a)
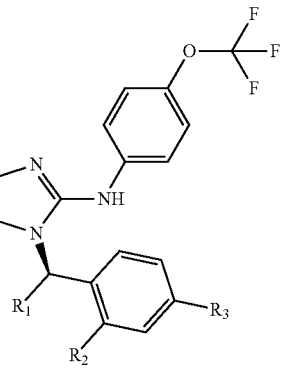
(I-3b)

wherein
E, L, $R_1$, $R_2$ and $R_3$ are as defined in the present disclosure.
The present disclosure also provides the compound as shown in the following formula, or an isomer thereof, or a pharmaceutically acceptable salt thereof, which is selected from
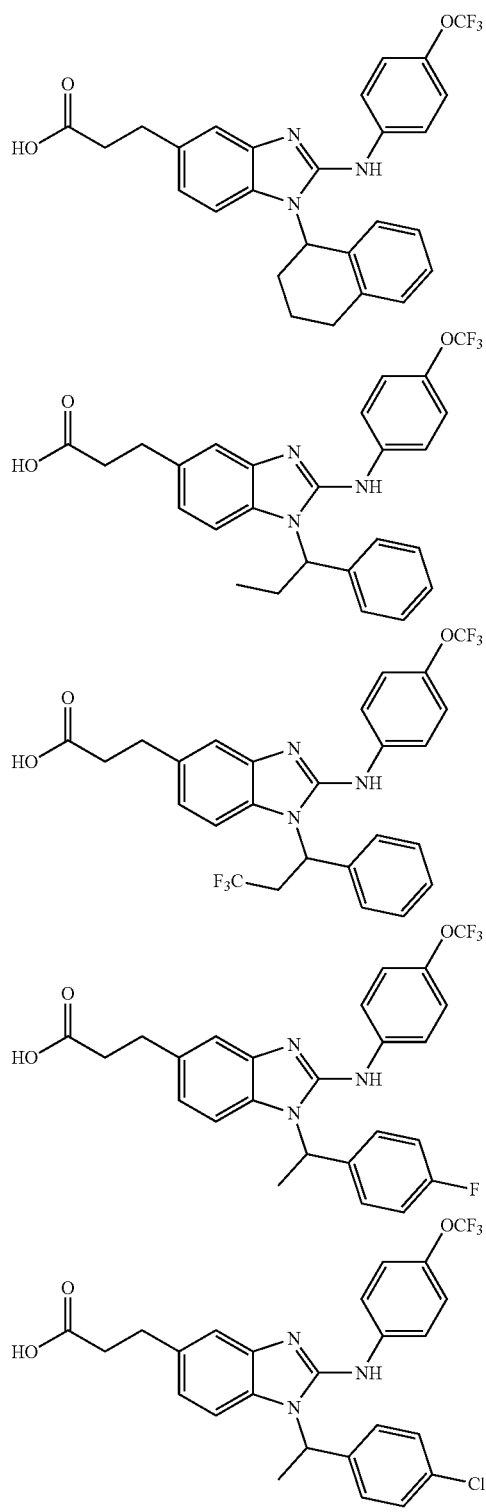
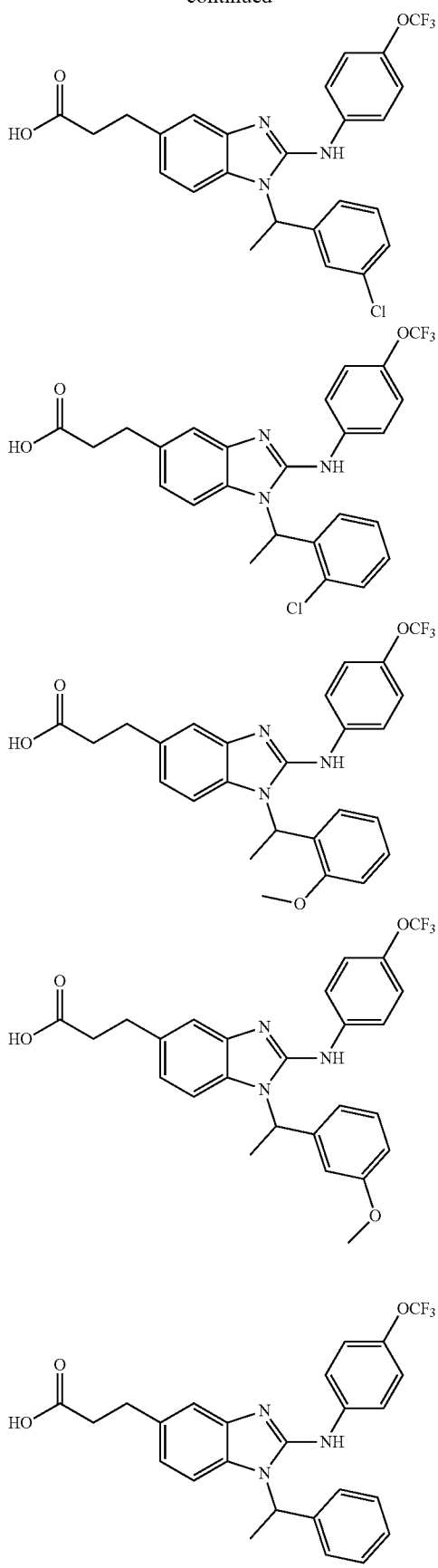

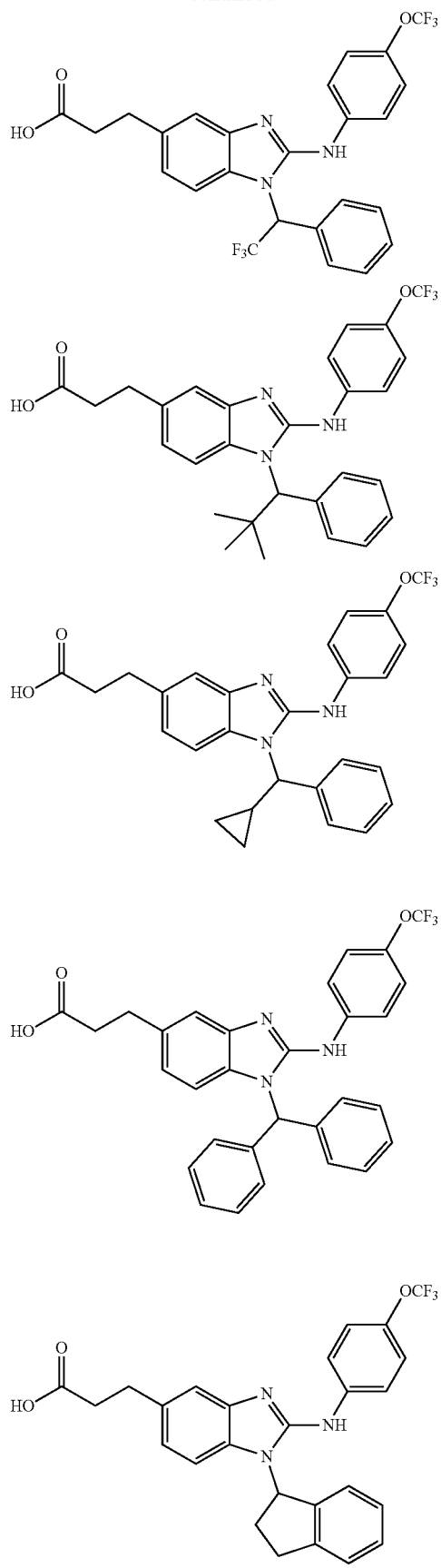
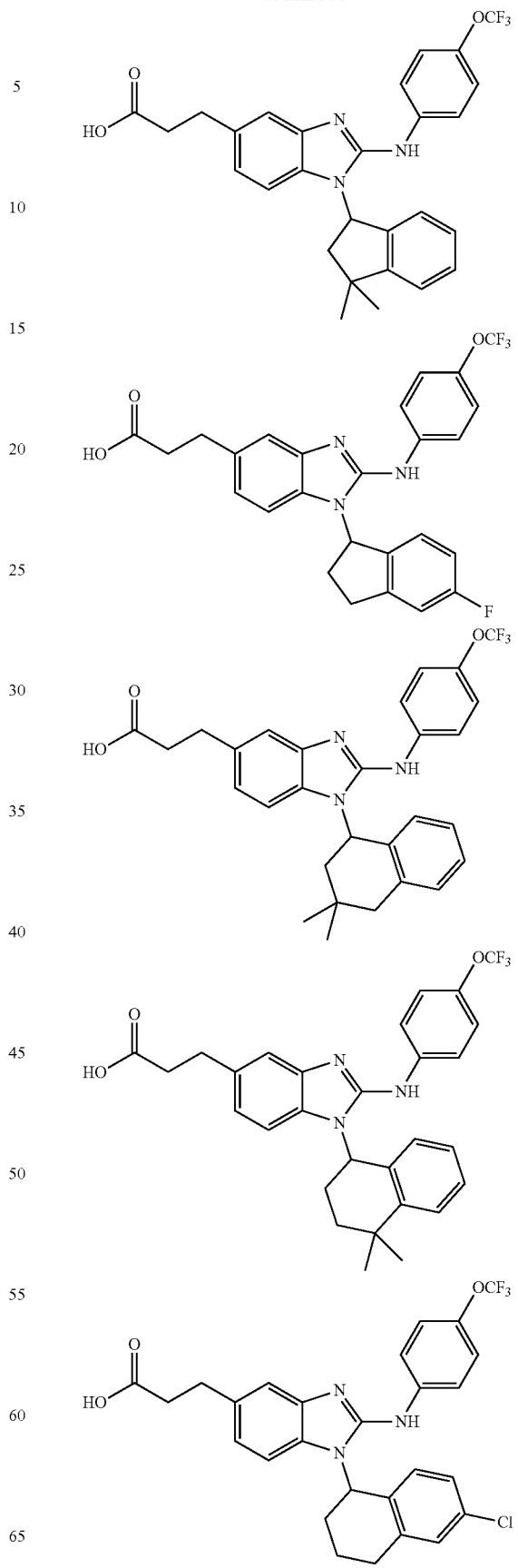

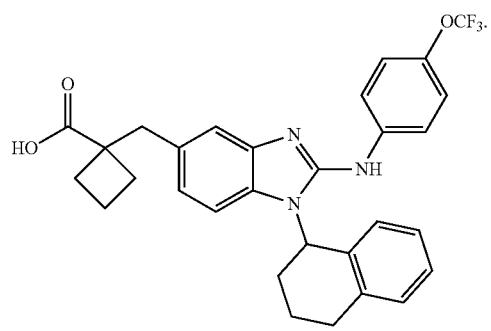 [SMILES: O=C(O)C1(Cc2ccc3c(c2)nc(Nc2ccc(OC(F)(F)F)cc2)n3C2CCCc3ccccc32)CCC1]
In some embodiments of the present disclosure, the above-mentioned compound is selected from
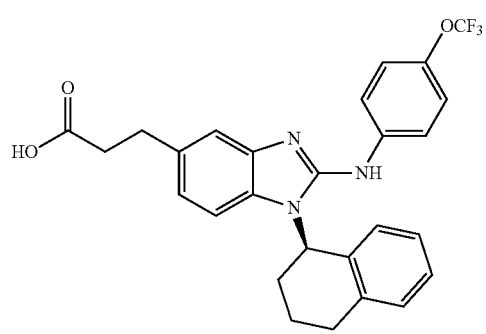
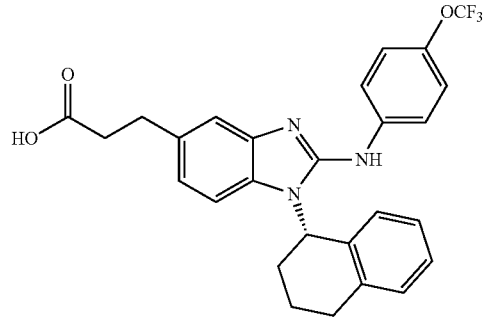
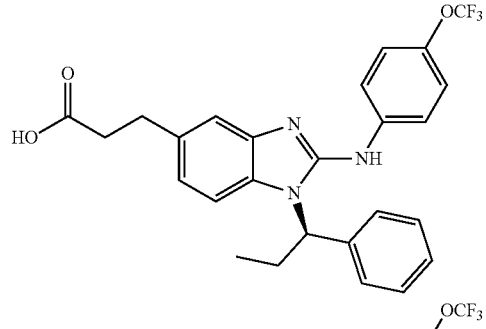
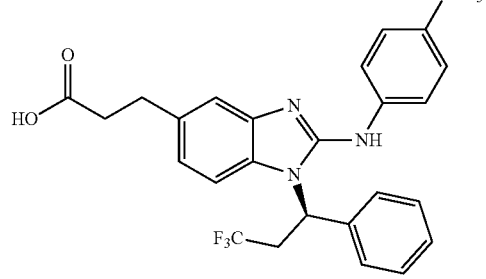
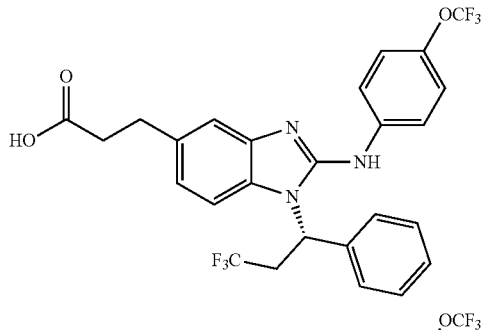
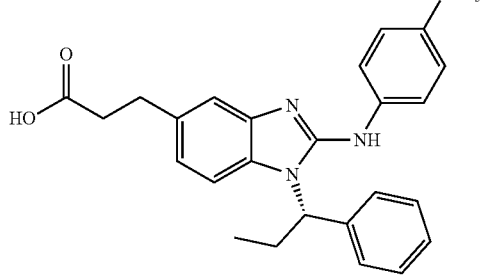
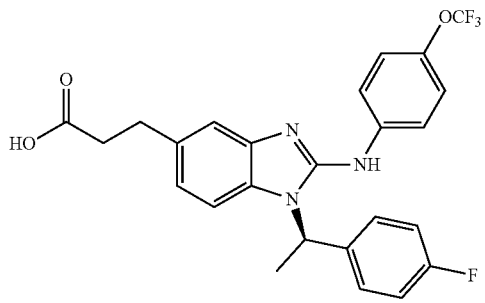
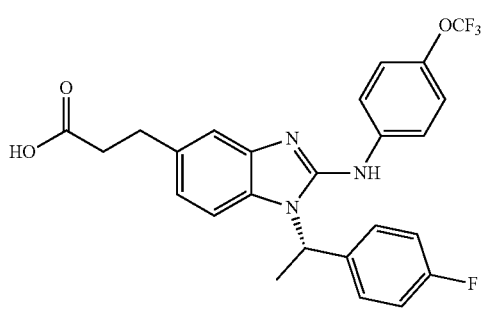
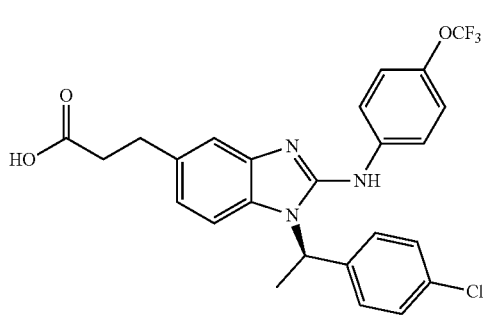

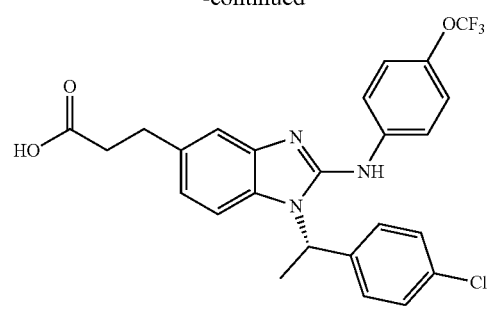
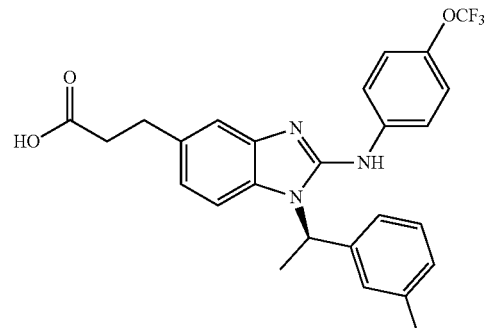
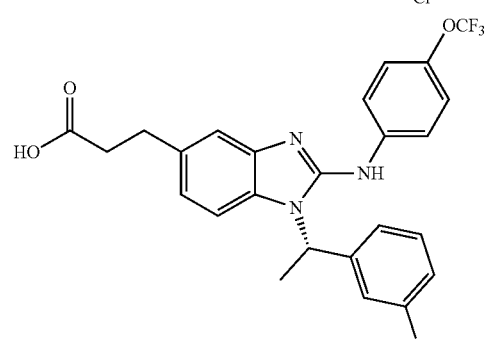
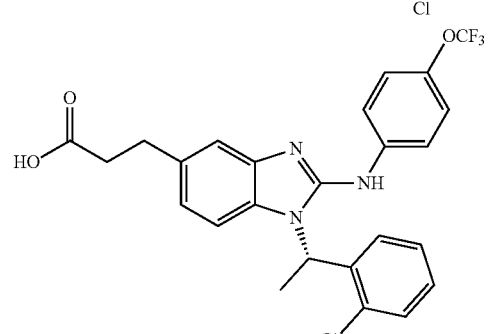
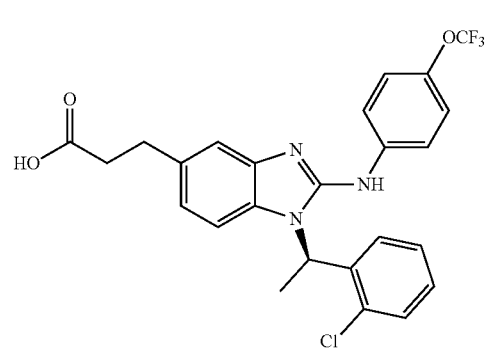
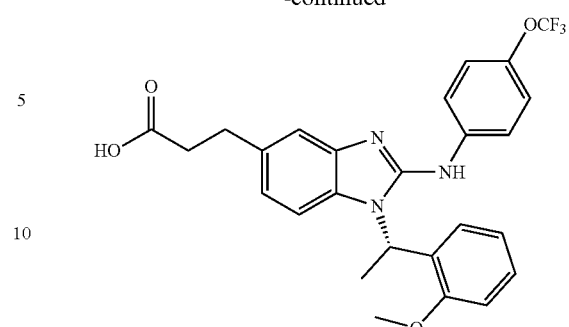
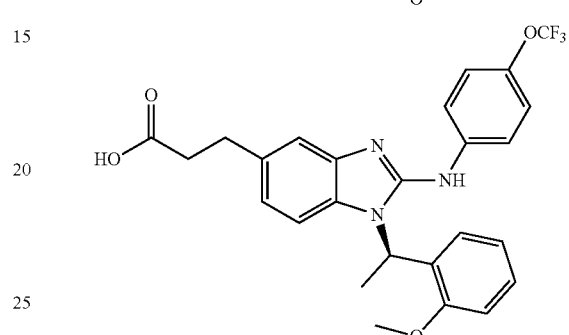
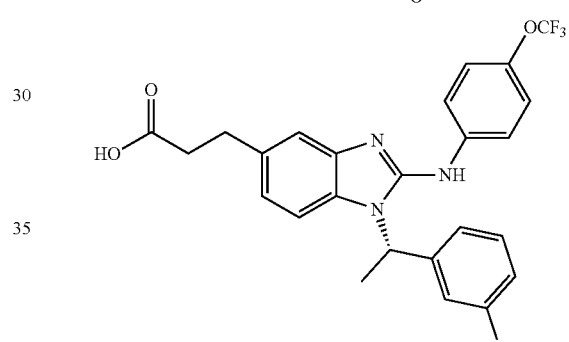
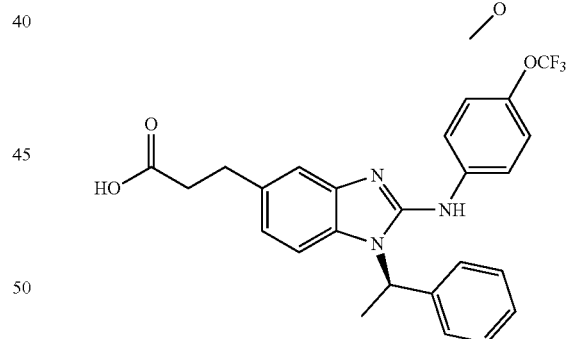
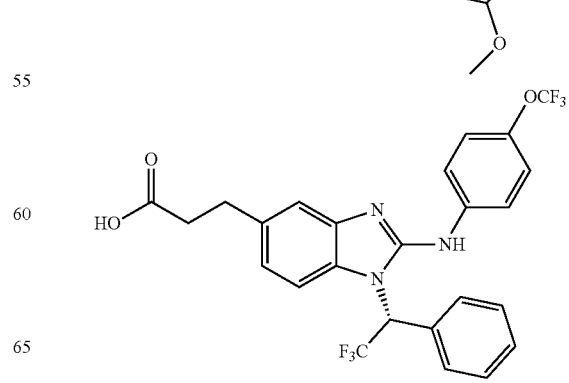

-continued
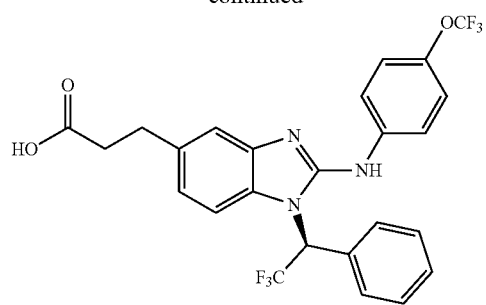
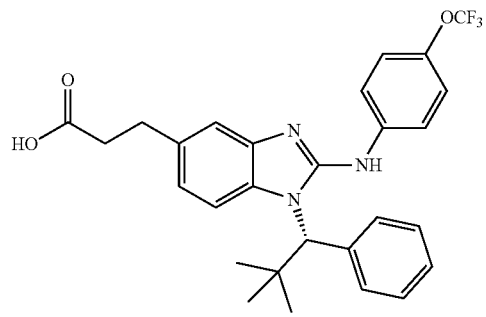
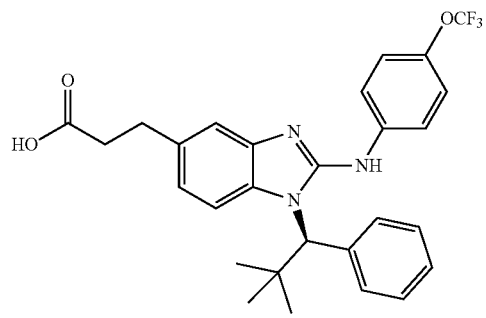
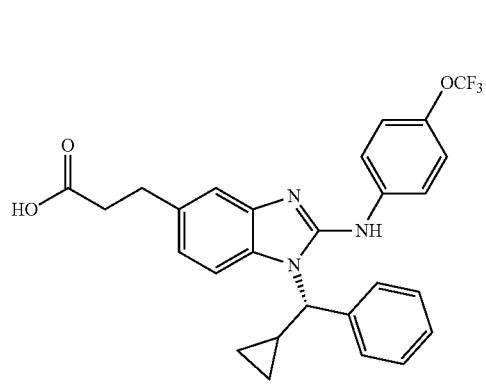
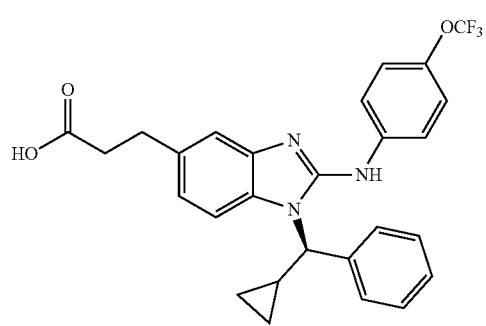
-continued
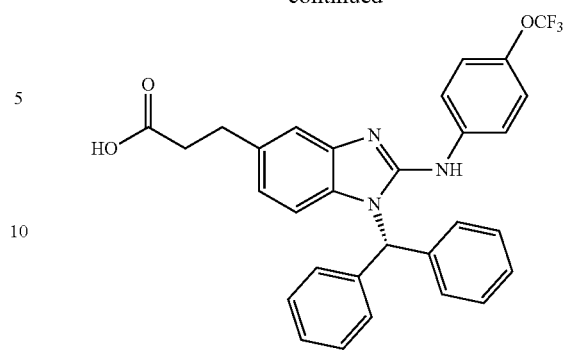
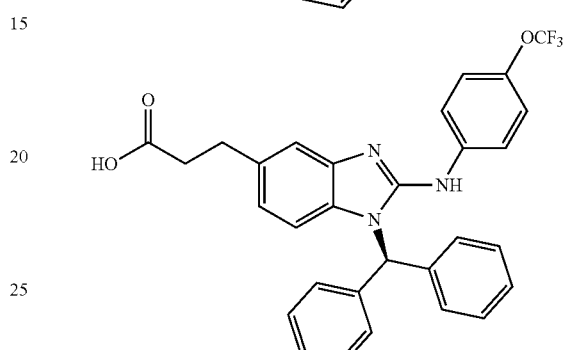
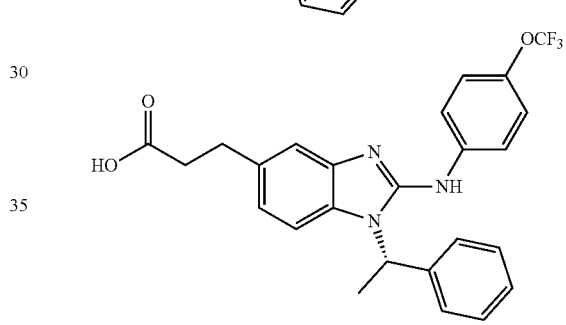
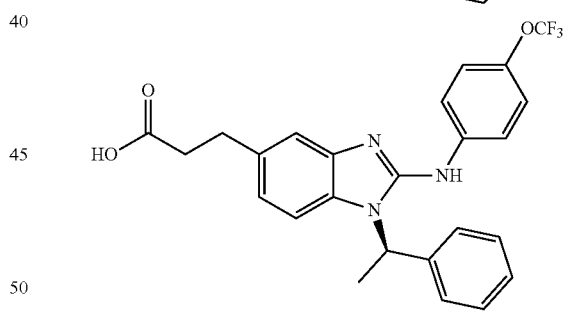
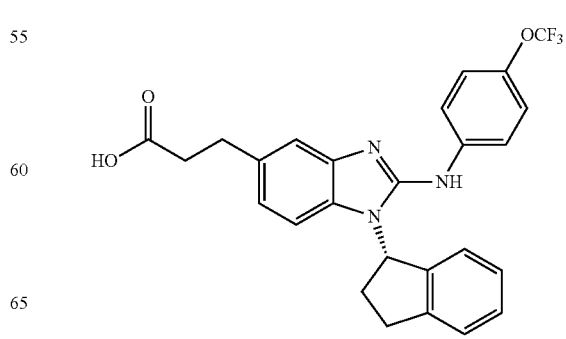

-continued
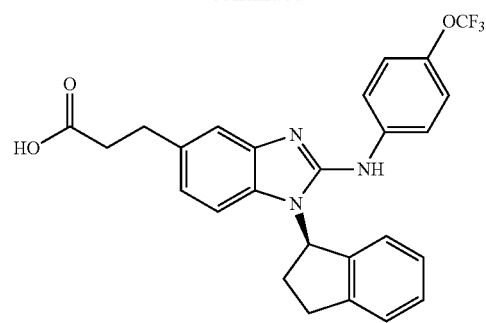
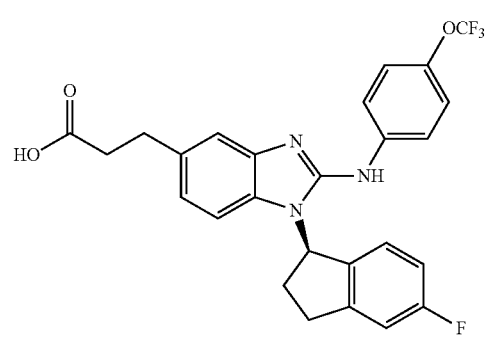
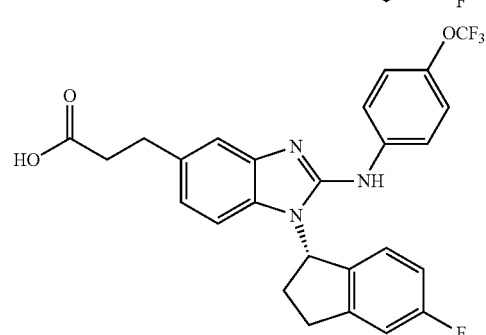
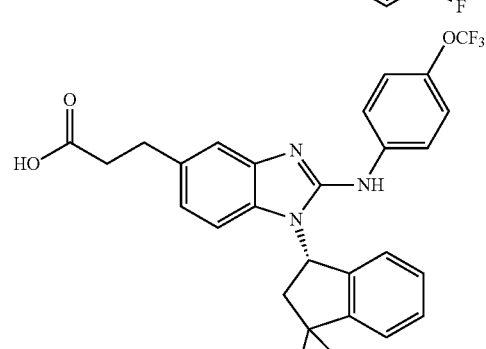
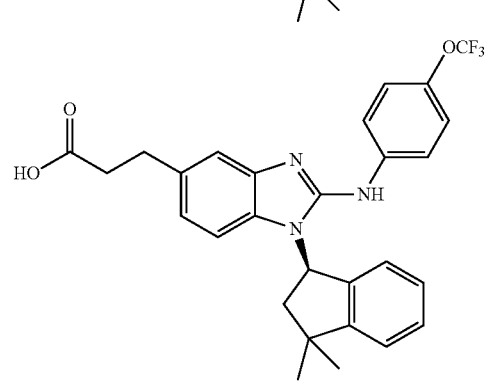
-continued
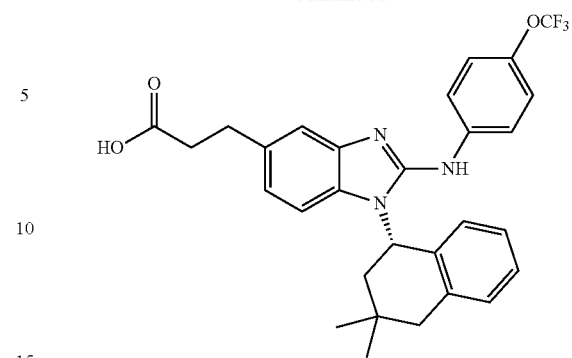
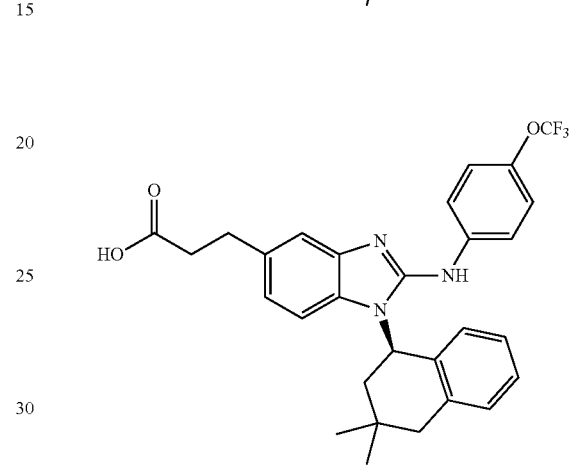
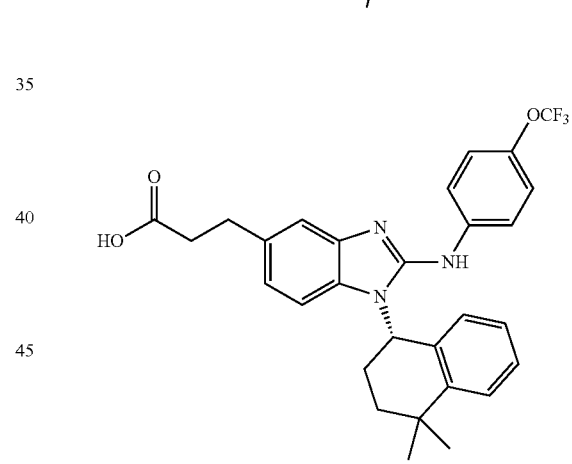
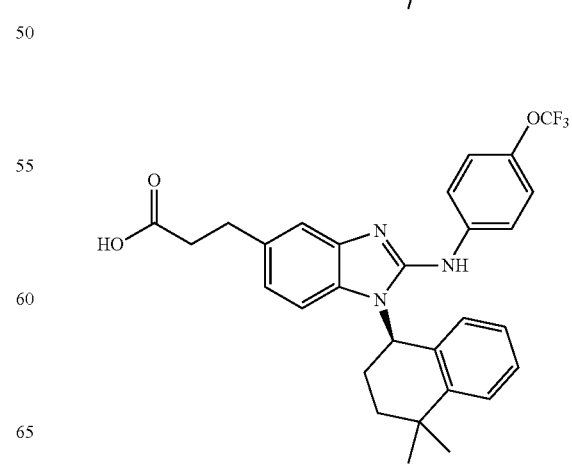

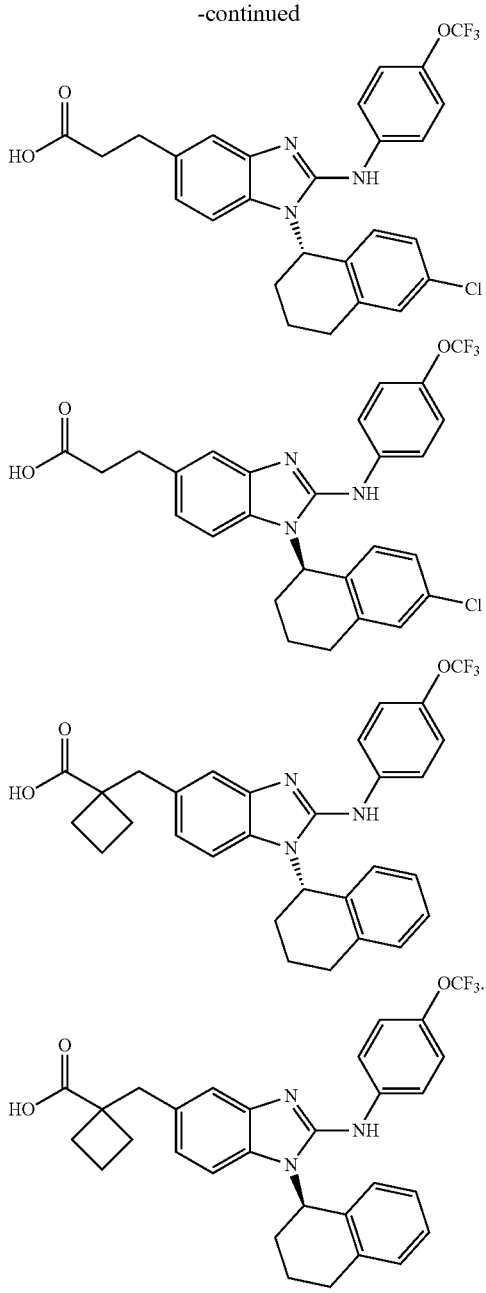

The present disclosure also provides use of the above-mentioned compound, or an isomer thereof, or a pharmaceutically acceptable salt thereof in the manufacture of a medicament for treating a disease related to IDH1.

Definition and Description

Unless otherwise stated, the following terms and phrases used herein are intended to have the following meanings. A specific term or phrase for which no special definition is provided should not be considered uncertain or unclear, but should be understood in its ordinary meaning. When a trade name appears herein, it is meant to refer to the corresponding commodity or the active ingredient thereof.

The term "pharmaceutically acceptable" used herein refers to those compounds, materials, compositions and/or dosage forms that within the scope of reliable medical judgment are suitable for contacting with human and animal tissues, without excessive toxicity, irritation, allergic reactions or other problems or complications, and that are commensurate with a reasonable benefit/risk ratio.

The term "pharmaceutically acceptable salt" refers to a salt of the compound of the present disclosure, which is prepared from a compound with specific substituents discovered in the present disclosure and a relatively non-toxic acid or base. When the compound of the present disclosure contains a relatively acidic functional group, a base addition salt can be obtained by contacting the neutral form of the compound with a sufficient amount of base in a pure solution or a suitable inert solvent. Pharmaceutically acceptable base addition salts include sodium, potassium, calcium, ammonium, organic ammonia or magnesium salt or similar salts. When the compound of the present disclosure contains a relatively basic functional group, an acid addition salt can be obtained by contacting the neutral form of the compound with a sufficient amount of acid in a pure solution or a suitable inert solvent. Examples of pharmaceutically acceptable acid addition salts include inorganic acid salts including, for example, hydrochloride, hydrobromide, nitrate, carbonate, bicarbonate, phosphate, monohydrogen phosphate, dihydrogen phosphate, sulfate, hydrogen sulfate, hydroiodide, phosphite, etc.; as well as organic acid salts, wherein the organic acid includes, for example, acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, p-toluene sulfonic acid, citric acid, tartaric acid and methanesulfonic acid, etc.; and also include salts of amino acids (such as arginine, etc.), and salts of organic acids such as glucuronic acid. Certain specific compounds of the present disclosure contain both basic and acidic functional groups, and thus can be converted into any base or acid addition salt.

The pharmaceutically acceptable salt of the present disclosure can be synthesized from the parent compound containing an acidic or basic functional group by conventional chemical methods. Generally, such salts are prepared by reacting these compounds in free acid or base form with stoichiometric amounts of appropriate bases or acids in water or organic solvents or a mixture of both.

The compounds of the present disclosure may exist in specific geometric or isomeric forms. The present disclosure contemplates all such compounds, including cis and trans isomers, (−)- and (+)-enantiomers, (R)- and (S)-enantiomers, diastereomers, (D)-isomers, (L)-isomers, and the racemic mixture and other mixtures thereof, such as enantiomers or diastereomeric enriched mixtures, which are all within the scope of the present disclosure. Additional asymmetric carbon atoms may be present in a substituent, such as alkyl. All these isomers and their mixtures are included in the scope of the present disclosure.

Unless otherwise specified, the term "enantiomer" or "optical isomer" refers to isomers that are mirror images of each other.

Unless otherwise specified, the term "cis-trans isomer" or "geometric isomer" is caused by the inability to rotate freely because of double bonds or single bonds of ring-forming carbon atoms.

Unless otherwise specified, the term "diastereomer" refers to stereoisomers which have two or more chiral centers and the molecules are non-mirror-image relationship.

Unless otherwise specified, "(D)" or "(+)" means dextrorotation, "(L)" or "(−)" means levorotatory, and "(DL)" or "(±)" means racemic.

Unless otherwise specified, the wedge-shaped solid line)(◥) and the wedge-shaped dashed line ( ) are used to indicate the absolute configuration of a stereocenter, the straight solid line (◥) and the straight dashed line ( ) are used to indicate the relative configuration of a stereocenter, the wavy line ( ) is used to indicate a wedge-shaped solid line (◥) or a wedge-shaped dashed line ( ) and the wavy line ( ) is used to indicate a straight solid line (◥) and a straight dashed line ( ).

Unless otherwise specified, for a compound in which there is a double bond, such as a carbon-carbon double bond, a carbon-nitrogen double bond, and a nitrogen-nitrogen double bond, and each atom on the double bond is connected to two different substituents (in a double bond containing a nitrogen atom, a lone pair of electrons on the nitrogen atom is regarded as a substituent connected thereto), if the atom on the double bond in the compound is connected to the substituent of the compound with a wavy line ( ), it means the (Z) isomer, (E) isomer or a mixture of two isomers of the compound. For example, the following formula (A) means that the compound exists as a single isomer of formula (A-1) or formula (A-2) or as a mixture of the two isomers of formula (A-1) and formula (A-2). The following formula (B) means that the compound exists as a single isomer of formula (B-1) or formula (B-2) or as a mixture of the two isomers of formula (B-1) and formula (B-2). The following formula (C) represents that the compound exists as a single isomer of formula (C-1) or formula (C-2) or as a mixture of the two isomers of formula (C-1) and formula (C-2).

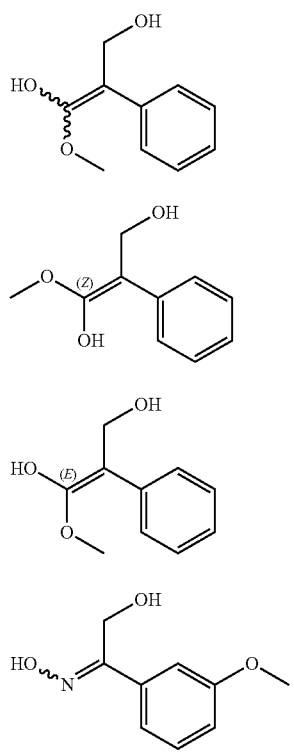

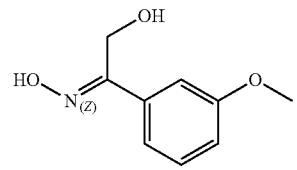

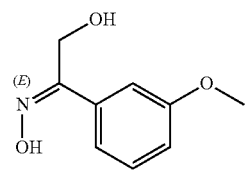

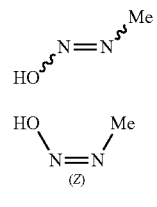

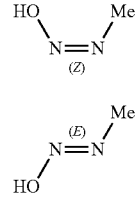

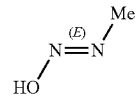

The compounds of the present disclosure may exist in specific forms. Unless otherwise specified, the term "tautomer" or "tautomeric form" means that at room temperature, the isomers with different functional groups are in dynamic equilibrium and can be transformed into each other quickly. If tautomers are possible (such as in a solution), the chemical equilibrium of the tautomers can be reached. For example, proton tautomer, also referred to as prototropic tautomer, includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers pentane-2,4-dione and 4-hydroxypent-3-en-2-one.

Unless otherwise specified, the terms "enriched in one isomer", "isomer enrichment", "enriched in one enantiomer" or "enantiomeric enrichment" means that the content of one isomer or enantiomer is less than 100%, and the content of the isomer or enantiomer is 60% or greater, or 70% or greater, or 80% or greater, or 90% or greater, or 95% or greater, or 96% or greater, or 97% or greater, or 98% or greater, or 99% or greater, or 99.5% or greater, or 99.6% or greater, or 99.7% or greater, or 99.8% or greater, or 99.9% or greater.

Unless otherwise stated, the term "isomer excess" or "enantiomeric excess" refers to the difference between the relative percentages of two isomers or two enantiomers. For example, if the content of one isomer or enantiomer is 90% and the content of the other isomer or enantiomer is 10%, the isomer or enantiomer excess (ee value) is 80%.

The optically active (R)- and (S)-isomers and D and L isomers can be prepared by chiral synthesis or chiral reagents or other conventional techniques. In order to obtain an enantiomer of a compound of the present disclosure, it can be prepared by asymmetric synthesis or derivatization with chiral auxiliary agents, in which the resulting mixture of diastereomers is separated, and the auxiliary group is cleaved to provide the pure desired enantiomer. Alternatively, when the molecule contains a basic functional group (such as an amino group) or an acidic functional group (such as a carboxyl group), it can form diastereomeric salts with appropriate optically active acids or bases, and then diastereomers can be resolved by conventional methods known in the art to recover the pure enantiomers. In addition, the separation of enantiomers and diastereomers is usually accomplished through the use of chromatography, which employs a chiral stationary phase and is optionally combined with chemical derivatization (for example, carbamate is generated from an amine). The compounds of the present disclosure may contain unnatural proportions of atomic isotopes on one or more of the atoms constituting the compound. For example, compounds can be labeled with radioisotopes, such as tritium ($^3$H), iodine-125 ($^{125}$I) or C-14 ($^{14}$C). For another example, deuterated drugs can be formed by replacing hydrogen with deuterium. The bond between deuterium and carbon is stronger than that of ordinary hydrogen and carbon. Compared with non-deuterated drugs, deuterated drugs have reduced toxic side effects and increased drug stability, enhanced efficacy, extend biological half-life and other advantages. All changes in the isotopic composition of the compounds of the present disclosure, whether radioactive or not, are included in the scope of the present disclosure.

"Optional" or "optionally" means that the event or condition described later may but not necessarily occur, and the description includes both the situation where the event or condition occurs and the situation where the event or condition does not occur.

The term "substituted" means that any one or more hydrogen atoms on a specific atom are replaced by substituents, including deuterium and hydrogen variants, as long as the valence of the specific atom is normal and the substituted compound is stable. When the substituent is oxygen (i.e. =O), it means that two hydrogen atoms are replaced. Oxygen substitution does not occur on aromatic groups. The term "optionally substituted" means that the group may be substituted or unsubstituted. Unless otherwise specified, the type and number of substituents can be arbitrary on the basis that they can be chemically realized.

When any variable (such as R) occurs more than once in the composition or structure of a compound, its definition in each case is independent. Thus, for example, if a group is substituted with 0-2 Rs, the group can optionally be substituted with up to two Rs, and in each case R is selected independently. In addition, combinations of substituents and/or variants thereof are only permitted if such combinations result in stable compounds.

When the number of a linking group is 0, such as —(CRR)$_0$—, it means that the linking group is a single bond.

When one of the variables is selected from a single bond, it means that the two groups connected are directly connected. For example, when L in A-L-Z represents a single bond, it means that the structure is actually A-Z.

When a substituent is vacant, it means that the substituent is absent. For example, when X in A-X is vacant, it means that the structure is actually A. When it is not specified through which atom the listed substituent is connected to the substituted group, such substituents can be bonded at any atom. For example, the pyridyl group as a substituent can be connected to the substituted group through any carbon atom on the pyridine ring. When it is not specified the connection direction of the listed linking groups, the connection direction is arbitrary. For example, if the linking group L in

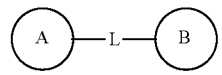

is -M-W—, then -M-W— can connect ring A and ring B in the same direction as the reading order from left to right to form

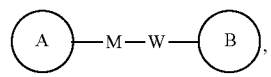, and can also connect ring A and ring B in the opposite direction to the reading order from left to right to form

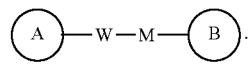.

Combinations of the linking groups, substituents, and/or variants thereof are only permitted if such combinations result in stable compounds.

Unless otherwise specified, the term "$C_{1-6}$ alkyl" is used to indicate a linear or branched saturated hydrocarbon group composed of 1 to 6 carbon atoms. The $C_{1-6}$ alkyl group includes $C_{1-5}$, $C_{1-4}$, $C_{1-3}$, $C_{1-2}$, $C_{2-6}$, $C_{2-4}$, $C_6$ and $C_5$ alkyl groups, etc.; and can be monovalent (such as methyl), divalent (such as methylene) or multivalent (such as methyne). Examples of $C_{1-6}$ alkyl groups include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, etc.

Unless otherwise specified, the term "$C_{1-3}$ alkyl" is used to denote a linear or branched saturated hydrocarbon group composed of 1 to 3 carbon atoms. The $C_{1-3}$ alkyl group includes $C_{1-2}$ and $C_{2-3}$ alkyl groups, etc.; and can be monovalent (such as methyl), divalent (such as methylene) or multivalent (such as methine). Examples of $C_{1-3}$ alkyl groups include, but are not limited to, methyl (Me), ethyl (Et), propyl (including n-propyl and isopropyl), and the like.

Unless otherwise specified, the term "$C_{1-6}$ alkoxy" refers to an alkyl group containing 1 to 6 carbon atoms that is attached to the rest of the molecule through an oxygen atom. The $C_{1-6}$ alkoxy group includes $C_{1-4}$, $C_{1-3}$, $C_{1-2}$, $C_{2-6}$, $C_{2-4}$, $C_6$, $C_5$, $C_4$, $C_3$ alkoxy, etc. Examples of $C_{1-6}$ alkoxy include but are not limited to methoxy, ethoxy, propoxy (including n-propoxy and isopropoxy), butoxy (including n-butoxy, isobutoxy, s-butoxy and t-butoxy), pentoxy (including n-pentoxy, isopentoxy and neopentoxy), hexoxy and the like.

Unless otherwise specified, the term "$C_{1-3}$ alkoxy" refers to an alkyl group containing 1 to 3 carbon atoms that are attached to the rest of the molecule through an oxygen atom. The $C_{1-3}$ alkoxy group includes $C_{1-2}$, $C_{2-3}$, $C_3$ and $C_2$ alkoxy groups, etc. Examples of $C_{1-3}$ alkoxy groups include, but are not limited to, methoxy, ethoxy, propoxy (including n-propoxy and isopropoxy) and the like.

Unless otherwise specified, "$C_{3-6}$ cycloalkyl" means a saturated cyclic hydrocarbon group composed of 3 to 6 carbon atoms, which is a monocyclic and bicyclic ring system. The $C_{3-6}$ cycloalkyl includes $C_{3-5}$, $C_{4-5}$ and $C_{5-6}$ cycloalkyl, etc.; and can be monovalent, divalent or multivalent. Examples of $C_{3-6}$ cycloalkyl groups include, but are not limited to, cyclopropyl, cyclobutyl, cyclopentyl, cyclohexyl and the like.

Unless otherwise specified, "$C_{4-6}$ cycloalkenyl" means a partially unsaturated cyclic hydrocarbon group composed of 4 to 6 carbon atoms containing at least one carbon-carbon double bond, which is monocyclic and bicyclic systems, wherein the bicyclic system includes spiro ring, fused ring and bridged ring, in which each ring is non-aromatic. The $C_{4-6}$ cycloalkenyl group includes a $C_{4-5}$ or $C_{5-6}$ cycloalkenyl group, etc.; and may be monovalent, divalent or multivalent. Examples of $C_{4-6}$ cycloalkenyl include, but are not limited to, cyclobutenyl, cyclopentenyl, cyclopentadienyl, cyclohexenyl, cyclohexadienyl, and the like.

Unless otherwise specified, the terms "$C_{6-12}$ aromatic ring" and "$C_{6-12}$ aryl" can be used interchangeably herein. The term "$C_{6-12}$ aromatic ring" or "$C_{6-12}$ aryl" means a cyclic hydrocarbon group composed of 6 to 12 carbon atoms with a conjugated π-electron system, which can be a single ring, a fused bicyclic ring or condensed tricyclic ring system in which each ring is aromatic. It can be monovalent, divalent or multivalent. $C_{6-12}$ aryl groups include $C_{6-10}$, $C_{6-9}$, $C_{6-8}$, $C_{12}$, $C_{10}$, and $C_6$ aryl groups. Examples of $C_{6-12}$ aryl groups include, but are not limited to, phenyl, naphthyl (including 1-naphthyl, 2-naphthyl, etc.).

Unless otherwise specified, $C_{n-n+m}$ or $C_n-C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, including any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc. Similarly, n-membered to n+m-membered means that the number of atoms in the ring is from n to n+m, for example, a 3-12-membered ring includes a 3-membered ring, 4-membered ring, 5-membered ring, 6-membered ring, 7-membered ring, 8-membered ring, 9-membered ring, 10-membered ring, 11-membered ring, and 12-membered ring, including any range from n to n+m, for example, 3-12 membered ring includes 3-6 membered ring, 3-9 membered ring, 5-6 membered ring, 5-7 membered ring, 6-7 membered ring, 6-8 membered ring, and 6-10 membered ring and the like.

The term "leaving group" refers to a functional group or atom that can be replaced by another functional group or atom through a substitution reaction (for example, an affinity substitution reaction). For example, representative leaving groups include triflate; chlorine, bromine, iodine; sulfonate, such as mesylate, tosylate, p-bromobenzenesulfonate, p-toluenesulfonate, etc.; acyloxy, such as acetoxy, trifluoroacetoxy, etc.

The term "protecting group" includes, but is not limited to, "amino protecting group", "hydroxy protecting group" or "thiol protecting group". The term "amino protecting group" refers to a protecting group suitable for preventing side reactions at the amino nitrogen position. Representative amino protecting groups include, but are not limited to: formyl; acyl, such as alkanoyl (such as acetyl, trichloroacetyl or trifluoroacetyl); alkoxycarbonyl, such as tert-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; silyl, such as trimethylsilyl (TMS) and tert-butyldimethylsilyl (TBS) and so on. The term "hydroxyl protecting group" refers to a protecting group suitable for preventing side reactions of the hydroxyl group. Representative hydroxy protecting groups include but are not limited to: alkyl groups, such as methyl, ethyl, and tert-butyl; acyl groups, such as alkanoyl (such as acetyl); arylmethyl, such as benzyl (Bn), p-methyloxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and so on.

The compounds of the present disclosure can be prepared by a variety of synthetic methods well known to those skilled in the art, including the specific embodiments listed below, the embodiments formed by their combination with other chemical synthesis methods, and equivalents or alternatives thereof known to those skilled in the art. Preferred embodiments include but are not limited to the examples of the present disclosure.

The solvent used in the present disclosure is commercially available. The present disclosure uses the following abbreviations: aq stands for water; HATU stands for O-(7-azabenzotriazol-1-yl)-N,N,N',N'-tetramethyluronium hexafluorophosphate; EDC stands for N-(3-dimethylaminopropyl)-N'-ethylcarbodiimide hydrochloride; m-CPBA stands for 3-chloroperoxybenzoic acid; eq stands for equivalent; CDI stands for carbonyl diimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH stands for methanol; CBz stands for benzyloxycarbonyl, which is an amine protecting group; BOC stands for tert-butoxycarbonyl which is an amine protecting group; HOAc stands for acetic acid; $NaCNBH_3$ stands for sodium cyanoborohydride; r.t. stands for room temperature; O/N stands for overnight; THF stands for tetrahydrofuran; $Boc_2O$ stands for di-tert-butyl dicarbonate; TFA stands for trifluoroacetic acid; DIPEA stands for diisopropylethylamine; $SOCl_2$ stands for thionyl chloride; $CS_2$ stands for carbon disulfide; TsOH stands for p-toluenesulfonic acid; NFSI stands for N-fluoro-N-(benzenesulfonyl)benzenesulfonamide; NCS stands for 1-chloropyrrolidine-2,5-dione; $n-Bu_4NF$ stands for tetrabutylammonium fluoride; iPrOH stands for 2-propanol; mp stands for melting point; EDCI stands for 1-(3-dimethylaminopropyl)-3-ethylcarbodiimide hydrochloride.

Compounds are named manually or by ChemDraw® software, and commercially available compounds are indicated by supplier catalog names.

Technical effect: At the enzymatic level, the compound of the present disclosure has a good inhibitory effect on the mutant IDH1R132H and IDH1R132C, and at the same time has no inhibitory effect on the wild-type IDH protein; at the cellular level, the compound of the present disclosure has a good 2-HG inhibitory effect on U87MG glioma cells with IDH1R132H mutation; the compound of the present disclosure has significant IDH1 mutant inhibitory effect and good selectivity, and at the same time has a better distribution ratio in brain tumors and parabrain tissues, which may reduce potential side effects on normal brain tissues

DETAILED DESCRIPTION

The following examples are intended to describe the present disclosure in detail, but are not meant to limit the present disclosure in any way. The present disclosure has been described in detail herein, and its specific embodiments are also disclosed. It will be obvious to those skilled in the art that various changes and improvements can be made to the specific embodiments of the present disclosure without departing from the spirit and scope of the present disclosure.

Process A

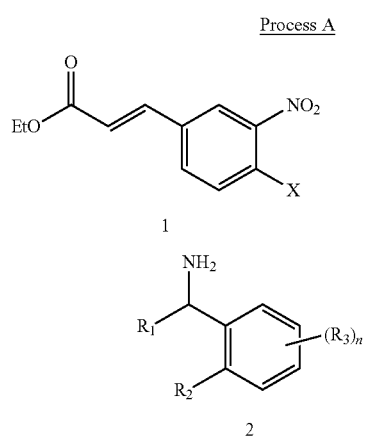

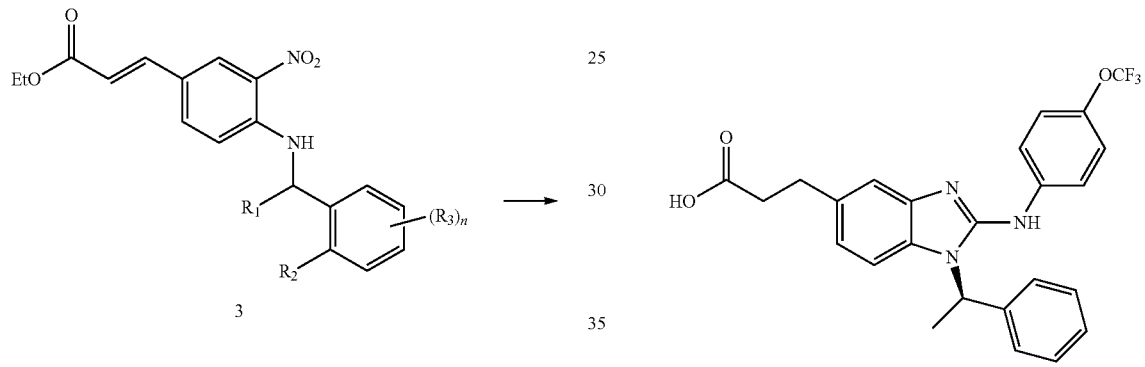

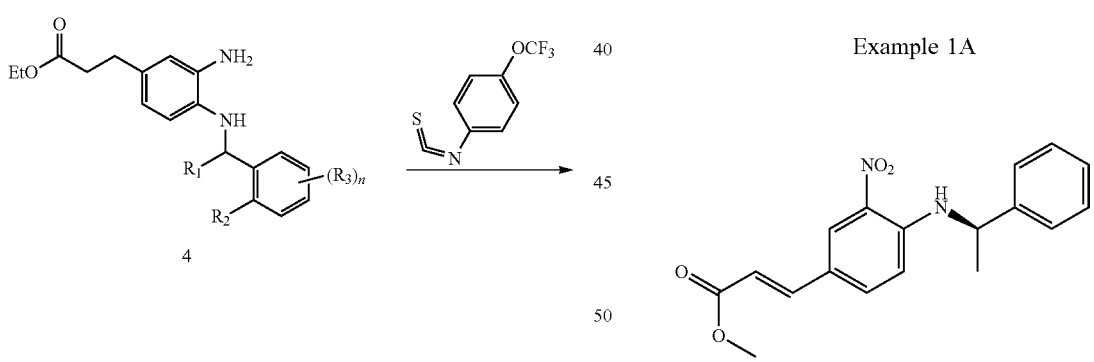

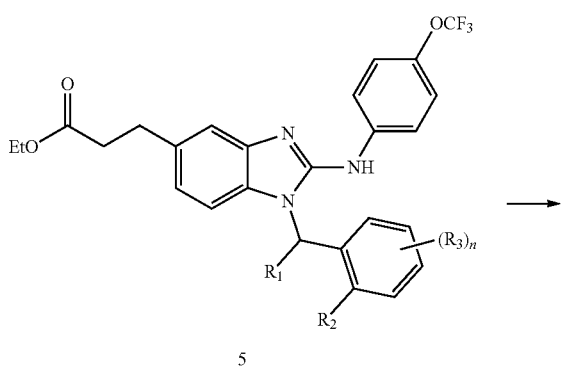

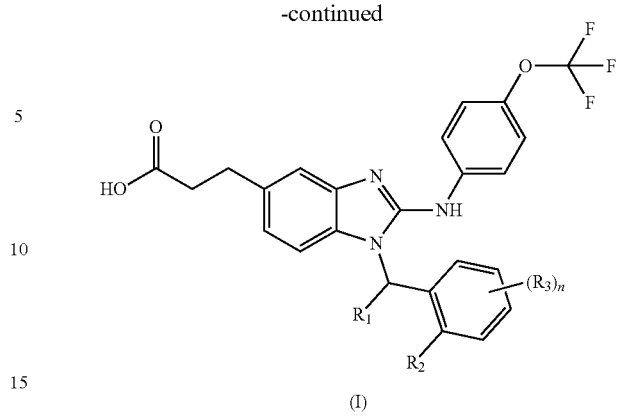

wherein, the groups are as defined in the compound of formula (I) of the present disclosure.

Example 1

Example 1A

Potassium carbonate (2.46 g, 17.76 mmol) was added to a solution of methyl (E)-3-(4-Fluoro-3-nitrophenyl)acrylate (2 g, 8.88 mmol) and (R)-1-phenylethylamine (1.18 g, 9.77 mmol, 1.26 mL) in tetrahydrofuran (20 mL), and the mixed solution was stirred at 50° C. for 16 hours. The reaction solution was diluted with 50 mL of water, and then extracted with ethyl acetate (30 mL×3). The combined organic phase was dried over anhydrous sodium sulfate, filtered, and concentrated under reduced pressure to obtain a crude product. At 15° C., the crude product was stirred in petroleum ether: ethyl acetate=10:1 (11 mL) for 30 minutes, filtered, and the solid was concentrated under reduced pressure to obtain Example 1A. $^1$H NMR (400 MHz, CDCl$_3$) δ=8.65 (d, J=5.4 Hz, 1H), 8.35 (d, J=2.1 Hz, 1H), 7.60-7.44

(m, 2H), 7.42-7.29 (m, 5H), 6.70 (d, J=8.9 Hz, 1H), 6.27 (d, J=15.9 Hz, 1H), 4.76 (q, J=6.5 Hz, 1H), 3.80 (s, 3H), 1.70 (d, J=6.7 Hz, 3H).

Example 1B

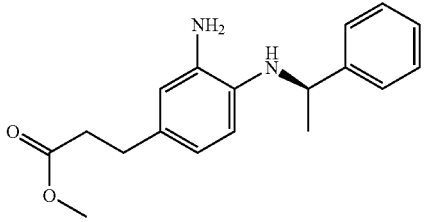 [SMILES: COC(=O)CCc1ccc(N[C@H](C)c2ccccc2)c(N)c1]

Under the protection of nitrogen gas, nickel chloride (1.99 g, 15.32 mmol) was added to a solution of Example 1A (1 g, 3.06 mmol) in methanol (20 mL), and after cooling to 0° C., sodium borohydride (695.57 mg, 18.39 mmol) was slowly added, and the mixed solution was stirred at 15° C. for 1 hour. The reaction was quenched by adding 100 mL of saturated ammonium chloride solution and stirring for 15 minutes. The reaction solution was extracted with ethyl acetate (80 mL×3), and the combined organic phase was dried over anhydrous sodium sulfate, filtered, and concentrated under reduced pressure to obtain Example 1B, which was used directly in the next step without purification.

Example 1C

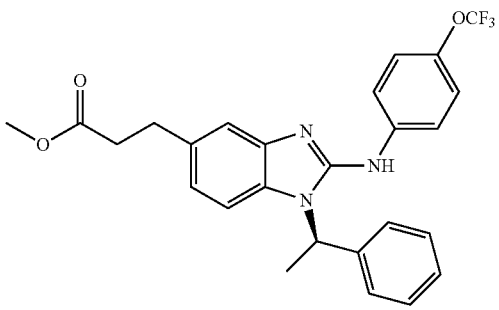 [SMILES: COC(=O)CCc1ccc2c(c1)nc(Nc1ccc(OC(F)(F)F)cc1)n2[C@H](C)c1ccccc1]

4-(trifluoromethoxy)phenyl isothiocyanate (888.84 mg, 4.06 mmol) was added to a solution of Example 1B (1.1 g, 3.69 mmol) in tetrahydrofuran (20 mL), stirred at 40° C. for half an hour, then EDC.HCl (1.41 g, 7.37 mmol) was added and stirred at 70° C. for 16 hours. The reaction solution was diluted with 30 mL of water, and then extracted with ethyl acetate (30 mL×3). The combined organic phase was dried over anhydrous sodium sulfate, filtered, and concentrated under reduced pressure to obtain a crude product, which was purified by column chromatography to obtain Example 1C. $^1$H NMR (400 MHz, CDCl$_3$) δ=7.43-7.29 (m, 6H), 7.21-7.17 (m, 2H), 7.09-6.98 (m, 3H), 6.91 (br d, J=7.9 Hz, 1H), 5.80 (br s, 1H), 5.67 (q, J=7.1 Hz, 1H), 3.70-3.48 (m, 3H), 2.98 (t, J=7.9 Hz, 2H), 2.61 (t, J=7.9 Hz, 2H), 1.82 (d, J=7.1 Hz, 3H).

Example 1

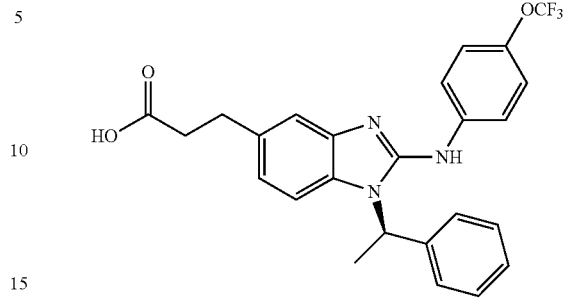

Lithium hydroxide (334.35 mg, 13.96 mmol) was added to a solution of Example 1C (1.35 g, 2.79 mmol) in tetrahydrofuran (10 mL) and water (10 mL), stirred at 15° C. for 16 hours, and the reaction solution was adjusted to pH 6 with 1M hydrochloric acid. The reaction solution was extracted with ethyl acetate (30 mL×3), and the combined organic phase was dried over anhydrous sodium sulfate, filtered, and concentrated under reduced pressure to obtain a crude product. The crude product was diluted with 5 ml of ethyl acetate, and then 20 ml of petroleum ether was added to precipitate a white solid. The solid was filtered, concentrated under reduced pressure, and then diluted with 10 ml of methyl tert-butyl ether, stirred for ten minutes, filtered, and the solid was concentrated under reduced pressure to obtain Example 1. $^1$H NMR (400 MHz, METHANOL-d4) δ=7.57 (br d, J=8.9 Hz, 2H), 7.43-7.21 (m, 8H), 6.90-6.63 (m, 2H), 5.97 (br d, J=6.8 Hz, 1H), 3.02-2.83 (m, 2H), 2.59 (br t, J=7.0 Hz, 2H), 2.03-1.92 (m, 3H)

Example 2

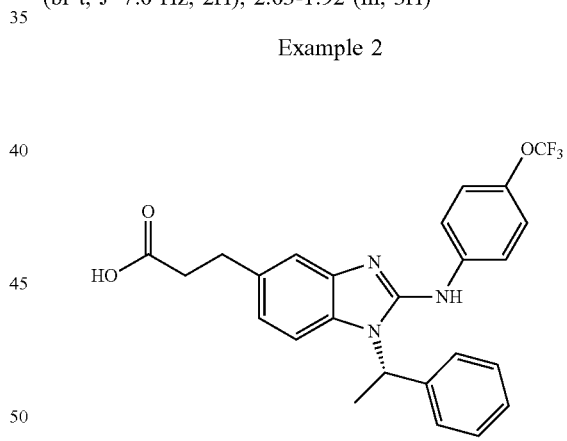

Example 2A

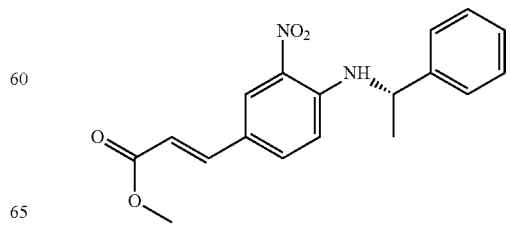

Potassium carbonate (2.46 g, 17.76 mmol) was added to a solution of methyl (E)-3-(4-fluoro-3-nitrophenyl)acrylate (2 g, 8.88 mmol) and (S)-1-phenylethylamine (1.08 g, 8.88 mmol) in tetrahydrofuran (20 mL), and the mixed solution was stirred at 50° C. for 16 hours. The reaction solution was diluted with 50 mL of water, and then extracted with ethyl acetate (30 mL×3). The combined organic phase was dried over anhydrous sodium sulfate, filtered, and concentrated under reduced pressure to obtain a crude product. At 15° C., the crude product was stirred in petroleum ether: ethyl acetate=10:1 (11 mL) for 30 minutes, filtered, and the solid was concentrated under reduced pressure to obtain Example 2A. $^1$H NMR (400 MHz, CDCl$_3$) δ=8.65 (br d, J=5.5 Hz, 1H), 8.35 (d, J=2.1 Hz, 1H), 7.56 (d, J=15.9 Hz, 1H), 7.47 (dd, J=2.0, 8.9 Hz, 1H), 7.41-7.29 (m, 5H), 6.70 (d, J=9.0 Hz, 1H), 6.27 (d, J=15.9 Hz, 1H), 4.76 (q, J=6.5 Hz, 1H), 3.80 (s, 3H), 1.70 (d, J=6.7 Hz, 3H).

Example 2B

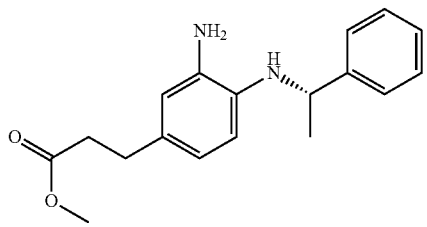 [SMILES: COC(=O)CCc1ccc(N[C@@H](C)c2ccccc2)c(N)c1]

Under the protection of nitrogen gas, nickel chloride (1.99 g, 15.32 mmol) was added to a solution of Example 2A (1 g, 3.06 mmol) in methanol (20 mL), and after cooling to 0° C., sodium borohydride (695.57 mg, 18.39 mmol) was slowly added, and the mixed solution was stirred at 15° C. for 1 hour. The reaction was quenched by adding 100 mL of saturated ammonium chloride solution and stirring for 15 minutes. The reaction solution was extracted with ethyl acetate (80 mL×3), and the combined organic phase was dried over anhydrous sodium sulfate, filtered, and concentrated under reduced pressure to obtain Example 2B, which was used directly in the next step without purification.

Example 2C

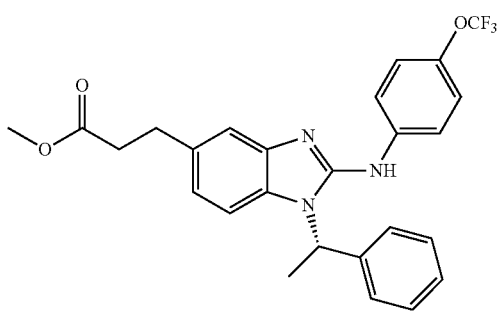 [SMILES: COC(=O)CCc1ccc2c(c1)nc(Nc1ccc(OC(F)(F)F)cc1)n2[C@@H](C)c1ccccc1]

4-(trifluoromethoxy)phenyl isothiocyanate (767.64 mg, 3.50 mmol) was added to a solution of Example 2B (950.00 mg, 3.18 mmol) in tetrahydrofuran (2 mL), stirred at 40° C. for half an hour, then EDCI (1.22 g, 6.37 mmol) was added and stirred at 70° C. for 16 hours. The reaction solution was diluted with 30 mL of water, and then extracted with ethyl acetate (30 mL×3). The combined organic phase was dried over anhydrous sodium sulfate, filtered, and concentrated under reduced pressure to obtain a crude product, which was purified by column chromatography to obtain Example 2C. $^1$H NMR (400 MHz, CDCl$_3$) δ=7.43-7.27 (m, 6H), 7.23-7.17 (m, 2H), 7.07-6.97 (m, 3H), 6.95-6.86 (m, 1H), 5.82 (br s, 1H), 5.67 (q, J=7.0 Hz, 1H), 3.61 (s, 3H), 2.97 (t, J=7.9 Hz, 2H), 2.61 (t, J=7.9 Hz, 2H), 1.82 (d, J=7.1 Hz, 3H).

Example 2

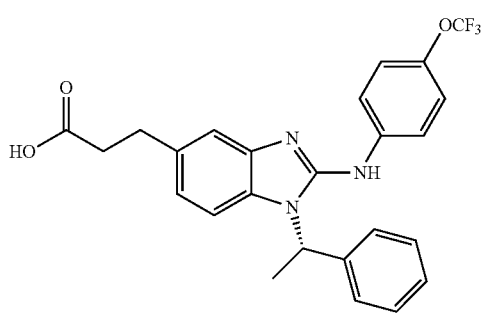 [SMILES: C[C@@H](c1ccccc1)n1c(Nc2ccc(OC(F)(F)F)cc2)nc2cc(CCC(=O)O)ccc21]

Lithium hydroxide (329.42 mg, 13.75 mmol) was added to a mixed solution of Example 2C (1.33 g, 2.75 mmol) in tetrahydrofuran (10 mL) and water (10 mL), stirred at 15° C. for 16 hours, and the reaction solution was adjusted to pH 6 with 1M hydrochloric acid. The reaction solution was extracted with ethyl acetate (30 mL×3), and the combined organic phase was dried over anhydrous sodium sulfate, filtered, and concentrated under reduced pressure to obtain a crude product. The crude product was diluted with 5 ml of ethyl acetate, and then 20 ml of petroleum ether was added to precipitate a white solid. The solid was filtered, concentrated under reduced pressure, and then diluted with 10 ml of methyl tert-butyl ether, stirred for ten minutes, filtered, and the solid was concentrated under reduced pressure to obtain Example 2. $^1$H NMR (400 MHz, METHANOL-d4) δ=7.56 (br d, J=7.2 Hz, 2H), 7.42-7.22 (m, 8H), 6.86-6.71 (m, 2H), 6.03-5.88 (m, 1H), 2.98-2.87 (m, 2H), 2.63-2.53 (m, 2H), 2.05-1.92 (m, 3H).

Example 3

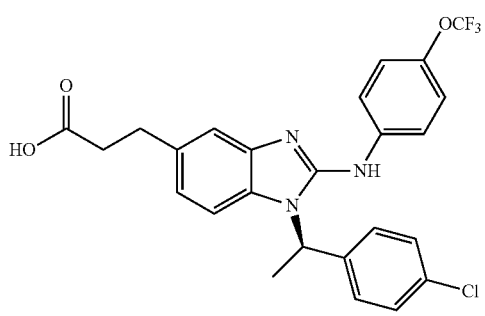 [SMILES: C[C@H](c1ccc(Cl)cc1)n1c(Nc2ccc(OC(F)(F)F)cc2)nc2cc(CCC(=O)O)ccc21]

Example 3A

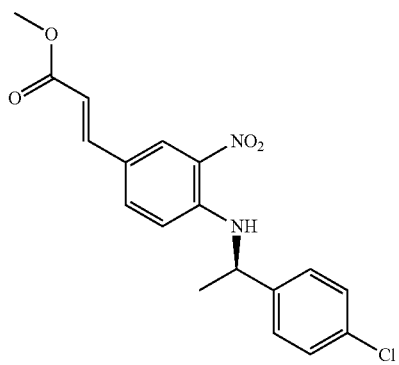 [SMILES: COC(=O)/C=C/c1ccc(N[C@H](C)c2ccc(Cl)cc2)c([N+](=O)[O-])c1]

Potassium carbonate (982.04 mg, 7.11 mmol) and (1R)-1-(4-chlorophenyl)ethylamine (552.91 mg, 3.55 mmol) were added to a solution of (E)-3-(4-fluoro-3-nitro-phenyl)prop-2-enoic acid methyl ester (800 mg, 3.55 mmol) in tetrahydrofuran (15 mL), and the mixture was stirred at 45° C. for 20 hours. The reaction mixture was concentrated under reduced pressure to remove the solvent. The residue was diluted with 100 mL of water and extracted with 300 mL (100 mL×3) of ethyl acetate. The combined organic layer was washed with 200 mL (100 mL×2) of saturated aqueous sodium chloride solution and dried over anhydrous sodium sulfate, filtered and concentrated under reduced pressure to obtain a residue. The residue was purified by column chromatography to obtain Example 3A. $^1$H NMR (400 MHz, CDCl$_3$) δ=8.58 (br d, J=5.4 Hz, 1H), 8.34 (d, J=2.1 Hz, 1H), 7.55 (d, J=16.0 Hz, 1H), 7.47 (dd, J=2.1, 9.0 Hz, 1H), 7.36-7.32 (m, 2H), 7.29-7.27 (m, 2H), 6.62 (d, J=9.0 Hz, 1H), 6.27 (d, J=16.0 Hz, 1H), 4.71 (quin, J=6.4 Hz, 1H), 3.79 (s, 3H), 1.66 (d, J=6.7 Hz, 3H).

Example 3B

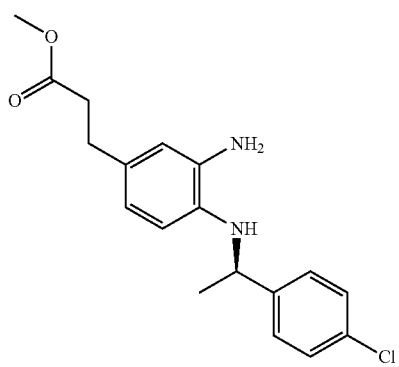 [SMILES: COC(=O)CCc1ccc(N[C@H](C)c2ccc(Cl)cc2)c(N)c1]

To a solution of Example 3A (1.01 g, 2.80 mmol) in methanol (10 mL) and tetrahydrofuran (6 mL), nickel chloride (3.33 g, 14.00 mmol) was added and then a solution of sodium borohydride (1.38 g, 36.39 mmol) in dimethylformamide (3 mL) was added dropwise, while controlling the internal temperature not to exceed 10° C., and then the reaction mixture was stirred at 10° C. for 1 hour. Water (80 mL) and ethyl acetate (30 mL) were added to the mixture and filtered through a pad of celite. The filter cake was washed with ethyl acetate (40 mL×3), and the filtrate was extracted with 150 mL of ethyl acetate. The combined organic phase was washed with saturated brine (100 mL×2), dried over anhydrous sodium sulfate and concentrated in vacuo to obtain Example 3B, which was used directly in the next step without purification.

Example 3C

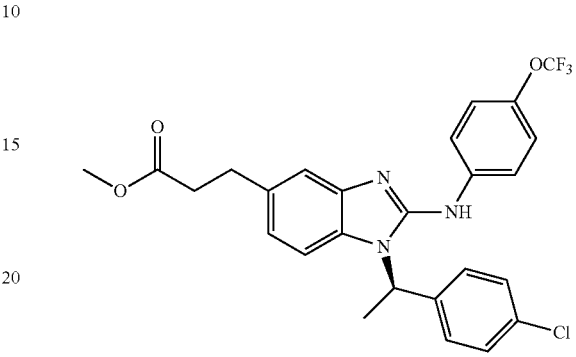

1-isothiocyanato-4-(trifluoromethoxy)benzene (515.06 mg, 2.35 mmol, 381.52 μL) was added to a solution of Example 3B (711 mg, 2.14 mmol) in tetrahydrofuran (8 mL), and the mixture was stirred at 45° C. for 1 hour, then EDCI (409.53 mg, 2.14 mmol) was added and the mixture was stirred at 70° C. for 15 hours. The reaction mixture was concentrated under reduced pressure to remove the solvent. The residue was diluted with 50 mL of water and extracted with 100 mL (50 mL×2) of ethyl acetate. The combined organic layer was washed with 100 mL (50 mL×2) of saturated aqueous sodium chloride solution, and dried over anhydrous sodium sulfate, filtered and concentrated under reduced pressure to obtain a residue. The residue was purified by column chromatography (SiO$_2$, petroleum ether/ethyl acetate=1/0 to 10:1) to obtain Example 3C, which was used directly in the next step without purification.

Example 3

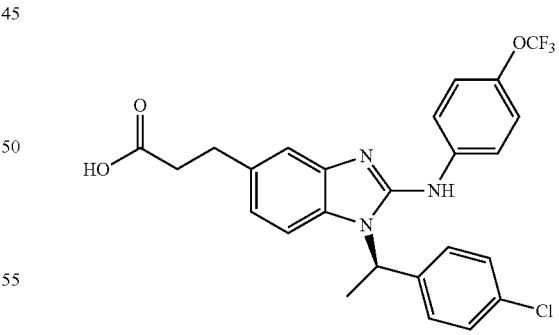

Lithium hydroxide (288.84 mg, 6.88 mmol) was added to a solution of Example 3C (713 mg, 1.38 mmol) in tetrahydrofuran (4 mL) and water (2 mL), and the mixture was stirred at 20° C. for 16 hours. The mixture was acidified to pH=6 with dilute hydrochloric acid (1N), and extracted with 200 mL (100 mL×2) of ethyl acetate. The combined organic layer was washed with 200 mL (100 mL×2) of saturated aqueous salt solution, dried with anhydrous sodium sulfate, filtered, and concentrated under reduced pressure to obtain a residue. The residue was purified by high performance liquid chromatography (TFA conditions) to obtain Example 3D. ¹H NMR (400 MHz, DMSO-d6) δ=7.78 (br s, 2H), 7.47 (s, 6H), 7.26 (s, 1H), 6.98-6.76 (m, 2H), 6.14-6.03 (m, 1H), 3.42 (br s, 2H), 2.85 (br t, J=7.3 Hz, 2H), 1.96 (br d, J=6.7 Hz, 3H).

Example 4

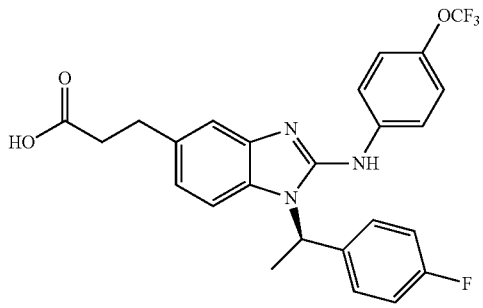 [SMILES: C[C@H](c1ccc(F)cc1)n1c(Nc2ccc(OC(F)(F)F)cc2)nc2cc(CCC(=O)O)ccc21]

Example 4A

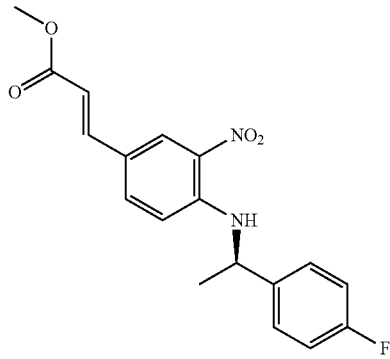 [SMILES: COC(=O)/C=C/c1ccc(N[C@H](C)c2ccc(F)cc2)c([N+](=O)[O-])c1]

Potassium carbonate (982.04 mg, 7.11 mmol) and (1R)-1-(4-fluorophenyl)ethylamine (494.45 mg, 3.55 mmol) were added to a solution of (E)-3-(4-fluoro-3-nitro-phenyl)prop-2-enoic acid methyl ester (800 mg, 3.55 mmol) in tetrahydrofuran (15 mL), and the mixture was stirred at 45° C. for 20 hours. The reaction mixture was concentrated under reduced pressure to remove the solvent. The residue was diluted with 100 mL of water and extracted with 300 mL (100 mL×3) of ethyl acetate. The combined organic layer was washed with 200 mL (100 mL×2) of brine, dried over anhydrous sodium sulfate, filtered, and concentrated under reduced pressure to obtain a residue. The residue was purified by column chromatography (SiO₂, petroleum ether/ethyl acetate=1/0 to 5:1) to obtain Example 4A. ¹H NMR (400 MHz, CDCl₃) δ=8.59 (br d, J=5.1 Hz, 1H), 8.34 (d, J=2.2 Hz, 1H), 7.55 (d, J=15.9 Hz, 1H), 7.48 (dd, J=2.1, 8.9 Hz, 1H), 7.34-7.28 (m, 2H), 7.09-7.01 (m, 2H), 6.65 (d, J=8.9 Hz, 1H), 6.27 (d, J=16.0 Hz, 1H), 4.73 (quin, J=6.5 Hz, 1H), 3.79 (s, 3H), 1.66 (d, J=6.7 Hz, 3H).

Example 4B

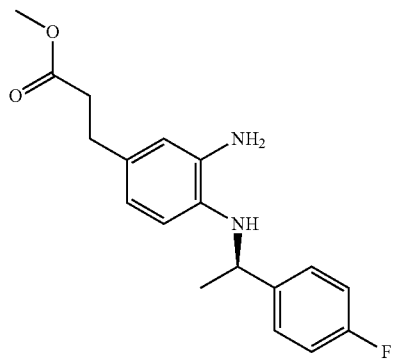 [SMILES: COC(=O)CCc1ccc(N[C@H](C)c2ccc(F)cc2)c(N)c1]

To a solution of Example 4A (1.01 g, 2.93 mmol) in methanol (6 mL) and tetrahydrofuran (6 mL), nickel chloride (3.49 g, 14.67 mmol) was added and then a solution of sodium borohydride (1.4 g, 38.1 mmol) in dimethylformamide (3 mL) was added dropwise, while controlling the internal temperature not to exceed 10° C., and then the reaction mixture was stirred at 10° C. for 1 hour. The mixture was poured into water (80 mL) and ethyl acetate (30 mL) and filtered through a pad of celite. The filter cake was washed with ethyl acetate (40 mL×3), the mixture was extracted with 150 mL of ethyl acetate. The combined organic phase was washed with saturated brine (100 mL×2), dried over anhydrous sodium sulfate and concentrated in vacuo to obtain Example 4B, which was used directly in the next step without purification.

Example 4C

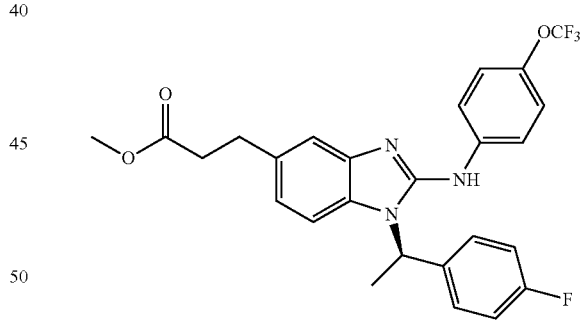

1-isothiocyanoyl-4-(trifluoromethoxy)benzene (313.22 mg, 1.43 mmol) was added to a solution of Example 4B (411 mg, 1.30 mmol) in tetrahydrofuran (6 mL), and the mixture was stirred at 45° C. for 1 hour, then EDCI (249.04 mg, 1.30 mmol) was added and the mixture was stirred at 70° C. for 15 hours. The reaction mixture was concentrated under reduced pressure to remove the solvent. The residue was diluted with 50 mL of water and extracted with 100 mL (50 mL×2) of ethyl acetate. The combined organic layer was washed with 100 mL (50 mL×2) of aqueous solution, dried over anhydrous sodium sulfate, filtered and concentrated under reduced pressure to obtain a residue. The residue was purified by column chromatography to obtain Example 4C, which was used directly in the next step without purification.

Example 4

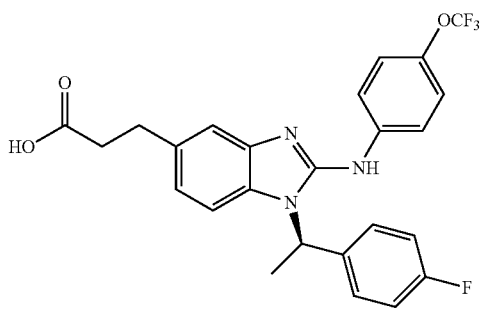 [SMILES: C[C@H](c1ccc(F)cc1)n1c(Nc2ccc(OC(F)(F)F)cc2)nc2cc(CCC(=O)O)ccc21]

Lithium hydroxide (139.33 mg, 3.32 mmol) was added to a solution of Example 4C (333 mg, 664.05 μmol) in tetrahydrofuran (4 mL) and water (2 mL), and the mixture was stirred at 20° C. for 16 hours. The mixture was acidified with dilute hydrochloric acid (1N, 6 mL) to pH=6, and extracted with 200 mL (100 mL×2) of ethyl acetate. The combined organic layer was washed with 200 mL (100 mL×2) of saline solution, and dried with anhydrous sodium sulfate, filtered and concentrated under reduced pressure to obtain a residue. The residue was purified by high performance liquid chromatography (TFA conditions) to obtain Example 4. $^1$H NMR (400 MHz, DMSO-d6) δ=7.79 (br d, J=8.4 Hz, 2H), 7.49 (br s, 4H), 7.29-7.21 (m, 3H), 6.95-6.78 (m, 2H), 6.08 (br d, J=7.0 Hz, 1H), 3.44-3.39 (m, 2H), 2.84 (br t, J=7.4 Hz, 2H), 1.96 (br d, J=6.7 Hz, 3H).

Example 5

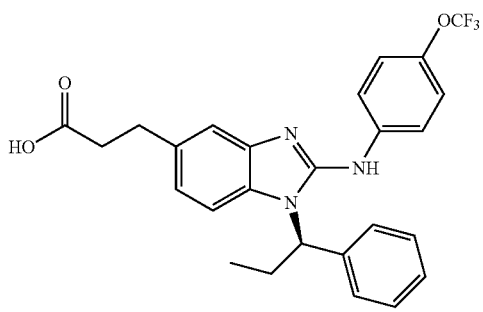 [SMILES: CC[C@H](c1ccccc1)n1c(Nc2ccc(OC(F)(F)F)cc2)nc2cc(CCC(=O)O)ccc21]

Example 5A

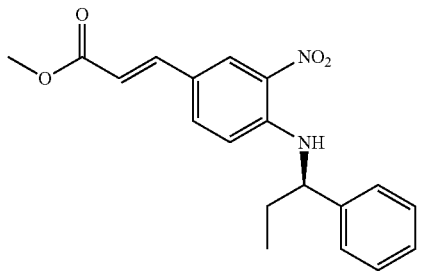 [SMILES: CC[C@@H](Nc1ccc(/C=C/C(=O)OC)cc1[N+](=O)[O-])c1ccccc1]

Potassium carbonate (920.67 mg, 6.66 mmol) and (1R)-1-Phenylprop-1-amine (330.25 mg, 2.44 mmol, 350.58 μL) were added to a solution of methyl (E)-3-(4-fluoro-3-nitrophenyl)acrylate (500 mg, 2.22 mmol) in tetrahydrofuran (10 mL), and the mixture was stirred at 50° C. for 16 hours. The reaction mixture was diluted with water (20 mL) and then extracted with ethyl acetate (10 mL×3). The combined organic layer was washed with brine (30 mL), dried over anhydrous sodium sulfate, filtered and concentrated under reduced pressure to obtain Example 5A, which was used directly in the next step without purification. $^1$H NMR (400 MHz, CDCl$_3$) δ=8.67 (br d, J=5.8 Hz, 1H), 8.24 (d, J=2.1 Hz, 1H), 7.46 (d, J=15.9 Hz, 1H), 7.36 (dd, J=2.1, 9.0 Hz, 1H), 7.32-7.19 (m, 6H), 6.60 (d, J=9.0 Hz, 1H), 6.16 (d, J=15.9 Hz, 1H), 4.41 (q, J=6.5 Hz, 1H), 3.70 (s, 3H), 1.95-1.85 (m, 2H), 0.96 (t, J=7.4 Hz, 3H)

Example 5B

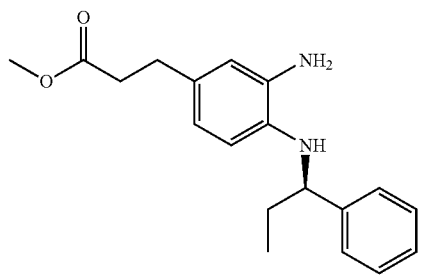 [SMILES: CC[C@@H](Nc1ccc(CCC(=O)OC)cc1N)c1ccccc1]

To a solution of Example 5A (400 mg, 1.18 mmol) in tetrahydrofuran (5 mL), nickel dichloride hexahydrate (1.12 g, 4.70 mmol) was added and then a solution of sodium borohydride (88.92 mg, 2.35 mmol) in dimethylformamide (1 mL) was added dropwise, while controlling the internal temperature not to exceed 10° C., and then the reaction mixture was stirred at 10° C. for 2 hours, then sodium borohydride (177.84 mg, 4.70 mmol) was added in batches at 0° C. and stirred at 15° C. 2 hours. The reaction mixture was diluted with water (20 mL) and then filtered. The filtrate was extracted with ethyl acetate (20 mL×4). The combined organic layer was washed with brine (40 mL×1), dried over anhydrous sodium sulfate, filtered and concentrated under reduced pressure to obtain Example 5B, which was used directly in the next step without purification.

Example 5C

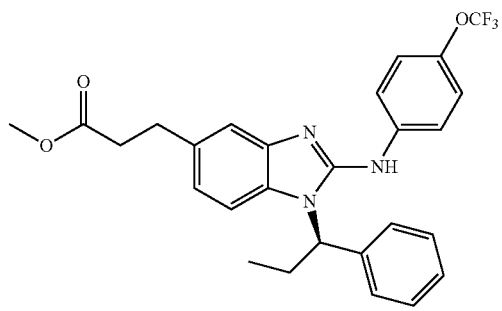 [SMILES: CC[C@H](c1ccccc1)n1c(Nc2ccc(OC(F)(F)F)cc2)nc2cc(CCC(=O)OC)ccc21]

4-(trifluoromethoxy)phenylthio isocyanate (270.12 mg, 1.23 mmol) was added to a solution of Example 5B (350 mg, 1.12 mmol) in tetrahydrofuran (5 mL), and the mixture was stirred at 25° C. for 1 hour. Then EDCI (429.54 mg, 2.24 mmol) was added to the mixture and reacted at 70° C. for 2 hours. The reaction mixture was concentrated under reduced pressure to remove tetrahydrofuran. The residue was diluted with water (10 mL) and extracted with ethyl acetate (10 mL×3). The combined organic layer was washed with HCl (1M, 5 mL) and brine (20 mL), dried over anhydrous sodium sulfate, filtered and concentrated under reduced pressure to obtain Example 5C, which was used directly in the next step without further purification.

Example 5

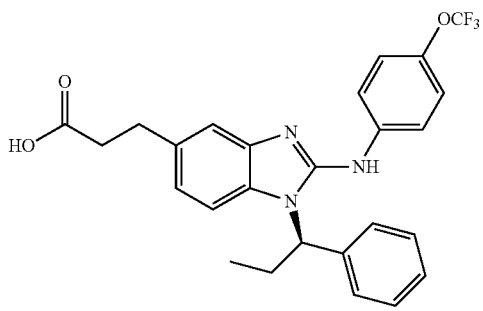 [SMILES: CC[C@H](c1ccccc1)n1c(Nc2ccc(OC(F)(F)F)cc2)nc2cc(CCC(=O)O)ccc21]

Lithium hydroxide monohydrate (126.52 mg, 3.02 mmol) was added to a solution of Example 5C (500 mg, 1.01 mmol) in water (5 mL), and the mixture was stirred at 20° C. for 16 hours. The mixture was adjusted to pH 6-7 with HCl (1M aqueous solution), and extracted with ethyl acetate (10 mL×4). The combined organic layer was washed with brine (20 m×1), dried with anhydrous sodium sulfate, and filtered and concentrated under reduced pressure to obtain the residue, which was separated and purified by high performance liquid chromatography (TFA conditions) to obtain Example 5. $^1$H NMR (400 MHz, METHANOL-d4) δ=7.67-7.60 (m, 2H), 7.56-7.43 (m, 6H), 7.42-7.36 (m, 1H), 7.32 (s, 1H), 7.08 (d, J=1.0 Hz, 2H), 5.84 (dd, J=5.5, 10.1 Hz, 1H), 2.98 (t, J=7.5 Hz, 2H), 2.76-2.65 (m, 1H), 2.65-2.54 (m, 3H), 1.06 (t, J=7.3 Hz, 3H).

Example 6

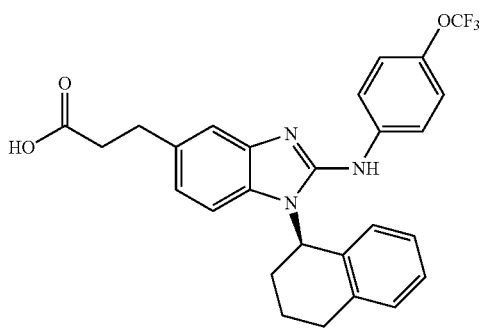 [SMILES: O=C(O)CCc1ccc2c(c1)nc(Nc1ccc(OC(F)(F)F)cc1)n2[C@@H]1CCCc2ccccc21]

Example 6A

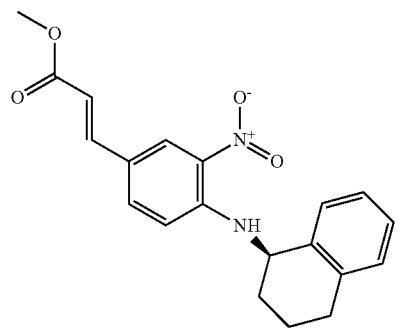 [SMILES: COC(=O)/C=C/c1ccc(N[C@@H]2CCCc3ccccc32)c([N+](=O)[O-])c1]

To a solution of methyl (E)-3-(4-fluoro-3-nitro-phenyl) prop-2-enoate (800 mg, 3.55 mmol) in tetrahydrofuran (10 mL) was added (1R)-tetrahydronaphthalene-1-amine (523.04 mg, 3.55 mmol) and potassium carbonate (982.04 mg, 7.11 mmol), and the mixture was stirred at 50° C. for 16 hours. The reaction mixture was concentrated under reduced pressure to remove the solvent. The residue was diluted with 100 mL of water and extracted with 200 mL (100 mL×2) of ethyl acetate. The combined organic layer was washed with 200 mL (100 mL×2) of saline solution, dried over anhydrous sodium sulfate, filtered, and concentrated under reduced pressure to obtain Example 6A, which was used directly in the next step without purification.

Example 6B

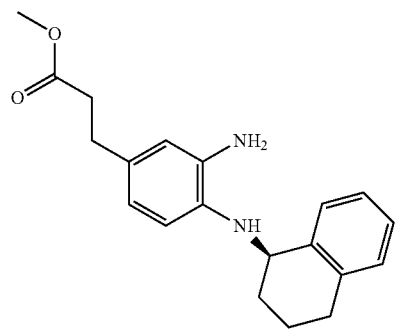 [SMILES: COC(=O)CCc1ccc(N[C@@H]2CCCc3ccccc32)c(N)c1]

To a solution of Example 6A (1.31 g, 3.72 mmol) in methanol (10 mL) was added nickel chloride (4.42 g, 18.59 mmol), and then a solution of sodium borohydride (1.97 g, 52.05 mmol) dissolved in dimethylformamide (3 mL) was added dropwise, while controlling the internal temperature not to exceed 10° C., and then the reaction mixture was stirred at 10° C. for 16 hours. The mixture was poured into water (100 mL), ethyl acetate (40 mL) and filtered through a pad of celite. The cake was washed with ethyl acetate (60 mL×3), and the mixture was extracted with 150 mL of ethyl acetate. The combined organic phase was washed with saturated brine (100 mL×2), dried over anhydrous sodium sulfate and concentrated under reduced pressure to obtain Example 6B, which was used directly in the next step without purification.

Example 6C

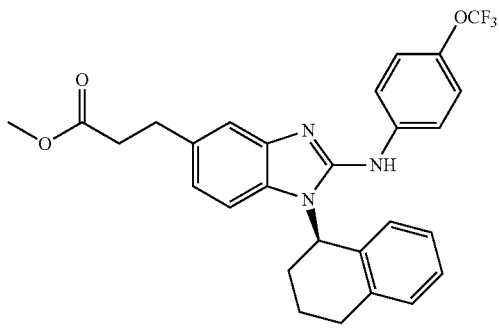 [SMILES: COC(=O)CCc1ccc2c(c1)nc(Nc1ccc(OC(F)(F)F)cc1)n2[C@@H]1CCCc2ccccc21]

To a solution of Example 6B (1.09 g, 2.99 mmol) in tetrahydrofuran (15 mL) was added isothiocyanoyl-4-(trifluoromethoxy)benzene (720.97 mg, 3.29 mmol), and the mixture was stirred at 50° C. for 1 hour. Then EDCI (573.25 mg, 2.99 mmol) was added and the mixture was stirred at 70° C. for 15 hours. The reaction mixture was concentrated under reduced pressure to remove the solvent. The residue was diluted with 100 mL of water and extracted with 200 mL (100 mL×2) of ethyl acetate. The combined organic layer was washed with 200 mL (100 mL×2) of saline solution, dried over anhydrous sodium sulfate, filtered and concentrated under reduced pressure to obtain a residue. The residue was purified by column chromatography (SiO$_2$, petroleum ether/ethyl acetate=1/0 to 12:1) to obtain Example 6C.

Example 6

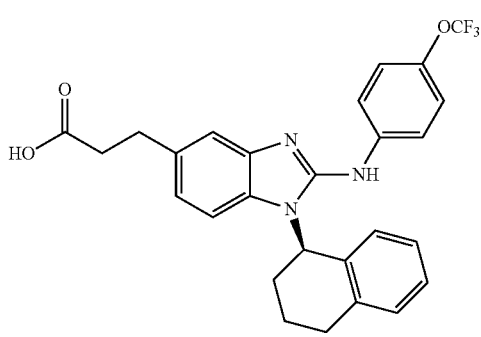 [SMILES: O=C(O)CCc1ccc2c(c1)nc(Nc1ccc(OC(F)(F)F)cc1)n2[C@@H]1CCCc2ccccc21]

To a solution of Example 6C (1.36 g, 2.64 mmol) in tetrahydrofuran (10 mL) and water (4 mL) was added lithium hydroxide (554.44 mg, 13.21 mmol), and the mixture was stirred at 25° C. for 16 hours. The mixture was acidified to pH=6 with dilute hydrochloric acid (1N, 4 ml), and extracted with 200 mL (100 mL×2) of ethyl acetate. The combined organic layer was washed with 200 mL (100 mL×2) of saline solution, dried over Na$_2$SO$_4$, filtered and concentrated under reduced pressure to obtain a residue. The residue was dissolved in EA (10 mL) and stirred at 25° C. for 30 min, then the mixture was filtered and washed with ethyl acetate (2×10 mL) to obtain Example 6. $^1$H NMR (400 MHz, METHANOL-d$_4$) δ=7.60 (br d, J=8.6 Hz, 2H), 7.33-7.15 (m, 5H), 7.04 (br t, J=7.0 Hz, 1H), 6.83 (br d, J=7.6 Hz, 1H), 6.74 (br d, J=7.9 Hz, 1H), 6.41 (br d, J=8.1 Hz, 1H), 5.88 (br t, J=8.1 Hz, 1H), 3.15-3.01 (m, 1H), 3.00-2.85 (m, 3H), 2.57 (br t, J=7.4 Hz, 2H), 2.30 (br s, 2H), 2.13 (br s, 1H), 2.01 (br d, J=16.1 Hz, 1H).

Example 7

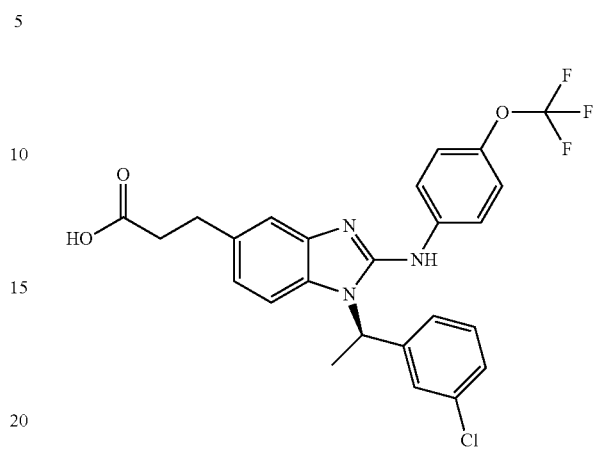

Example 7A

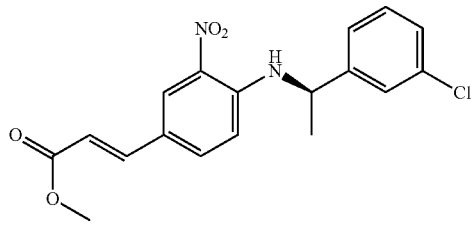 [SMILES: COC(=O)/C=C/c1ccc(N[C@H](C)c2cccc(Cl)c2)c([N+](=O)[O-])c1]

To a solution of methyl (E)-3-(4-Fluoro-3-nitrophenyl) acrylate (0.5 g, 2.22 mmol) and (R)-1-(3-chlorophenyl) ethylamine (380.12 mg, 2.44 mmol) in tetrahydrofuran (10 mL) was added potassium carbonate (613.78 mg, 4.44 mmol), and the mixed solution was stirred at 50° C. for 12 hours. The reaction solution was diluted with 30 mL of water, and then extracted with ethyl acetate (30 mL×3). The combined organic phase was dried over anhydrous sodium sulfate, filtered, and concentrated under reduced pressure to obtain a crude product. The crude product was purified by column chromatography to obtain Example 7A as a yellow oil. $^1$H NMR (400 MHz, CDCl$_3$) δ=8.49 (br d, J=5.5 Hz, 1H), 8.26 (d, J=2.1 Hz, 1H), 7.47 (d, J=15.9 Hz, 1H), 7.40 (dd, J=2.0, 9.0 Hz, 1H), 7.24 (s, 1H), 7.21-7.16 (m, 2H), 7.16-7.12 (m, 1H), 6.55 (d, J=9.0 Hz, 1H), 6.19 (d, J=15.9 Hz, 1H), 4.62 (quin, J=6.5 Hz, 1H), 3.71 (s, 3H), 1.59 (d, J=6.7 Hz, 3H).

Example 7B

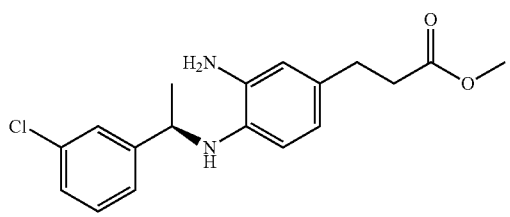 [SMILES: COC(=O)CCc1ccc(N[C@H](C)c2cccc(Cl)c2)c(N)c1]

Under the protection of nitrogen gas, nickel chloride (1.42 g, 10.95 mmol) was added to a solution of Example 7A (0.79 g, 2.19 mmol) in methanol (10 mL), and after cooling to 0° C., sodium borohydride (828.40 mg, 21.90 mmol) was slowly added, and the mixed solution was stirred at 15° C. for 0.5 hour. The reaction was quenched by adding 50 mL of saturated ammonium chloride solution and stirring for 15 minutes. The reaction solution was extracted with ethyl acetate (50 mL×3), and the combined organic phase was dried over anhydrous sodium sulfate, filtered, and concentrated under reduced pressure to obtain Example 7B as a yellow oil, which was used directly in the next step without further purification.

Example 7C

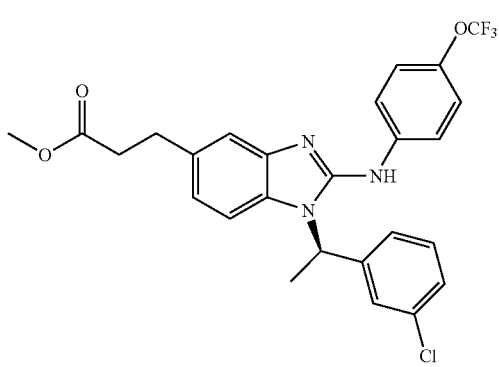 [SMILES: COC(=O)CCc1ccc2c(c1)nc(Nc1ccc(OC(F)(F)F)cc1)n2[C@H](C)c1cccc(Cl)c1]

To a solution of Example 7B (0.615 g, 1.85 mmol) in tetrahydrofuran (10 mL) was added 4-(trifluoromethoxy) phenyl isothiocyanate (486.02 mg, 2.22 mmol, 360.01 μL), the mixture was stirred at 40° C. for 0.5 hour, then EDC.HCl (708.46 mg, 3.70 mmol) was added and stirred at 70° C. for 5 hours. The reaction solution was diluted with 30 mL of water, and then extracted with ethyl acetate (30 mL×3). The combined organic phase was dried over anhydrous sodium sulfate, filtered, and concentrated under reduced pressure to obtain a crude product, which was purification by column chromatography to obtain Example 7C as a yellow solid.

Example 7

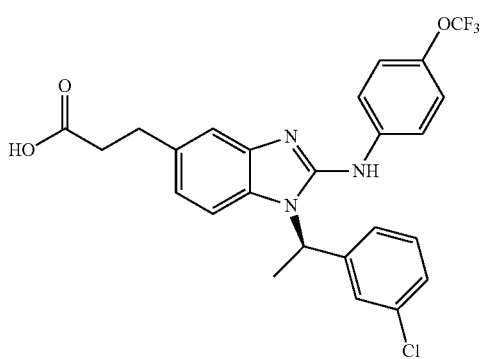 [SMILES: C[C@H](c1cccc(Cl)c1)n1c(Nc2ccc(OC(F)(F)F)cc2)nc2cc(CCC(=O)O)ccc21]

Lithium hydroxide (234.96 mg, 5.60 mmol) was added to a mixed solution of Example 7C (0.58 g, 1.12 mmol) in tetrahydrofuran (5 mL) and water (5 mL), and stirred at 20° C. for 16 hours. The reaction solution was adjusted to pH 6 with 1M hydrochloric acid, then diluted with 30 mL of water, and extracted with ethyl acetate (30 mL×3). The combined organic phase was dried over anhydrous sodium sulfate, filtered, and concentrated under reduced pressure to obtain a crude product. The crude product was purified by high performance liquid chromatography to obtain Example 7. $^1$H NMR (400 MHz, DMSO-d6) δ=9.27 (s, 1H), 7.93 (d, J=9.0 Hz, 2H), 7.44-7.32 (m, 5H), 7.28-7.21 (m, 2H), 6.79-6.68 (m, 2H), 6.07 (q, J=6.9 Hz, 1H), 2.82 (br t, J=7.5 Hz, 2H), 2.53 (br s, 2H), 1.90 (d, J=7.0 Hz, 3H).

Example 8

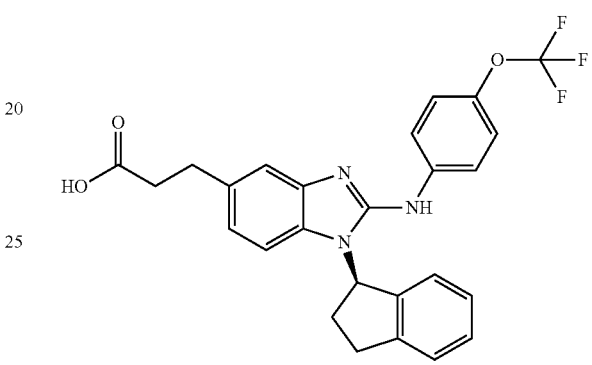

Example 8A

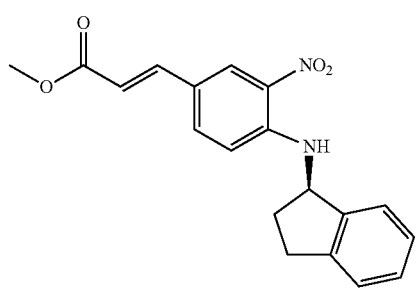 [SMILES: COC(=O)/C=C/c1ccc(N[C@@H]2CCc3ccccc32)c([N+](=O)[O-])c1]

To a solution of methyl (E)-3-(4-Fluoro-3-nitro-phenyl) prop-2-enoate (500 mg, 2.22 mmol) in THF (10 mL) was added K$_2$CO$_3$ (920.67 mg, 6.66 mmol) and (1R)-Indan-1-amine (325.33 mg, 2.44 mmol, 312.81 μL). The mixture was stirred at 50° C. for 16 hours. The reaction mixture was diluted with water (20 mL) and extracted with ethyl acetate (20 mL×3). The combined organic layer was washed with brine (20 mL×2), dried over sodium sulfate, filtered, and concentrated under reduced pressure to obtain Example 8A. $^1$H NMR (400 MHz, CDCl$_3$) δ=8.46 (br d, J=7.0 Hz, 1H), 8.29 (d, J=2.1 Hz, 1H), 7.60 (dd, J=2.1, 9.0 Hz, 1H), 7.54 (d, J=15.9 Hz, 1H), 7.31-7.19 (m, 4H), 7.18-7.11 (m, 1H), 7.05 (d, J=9.0 Hz, 1H), 6.26 (d, J=15.9 Hz, 1H), 5.15 (q, J=7.1 Hz, 1H), 3.73 (s, 3H), 3.08-2.99 (m, 1H), 2.96-2.86 (m, 1H), 2.70-2.60 (m, 1H), 2.02-1.96 (m, 1H).

Example 8B

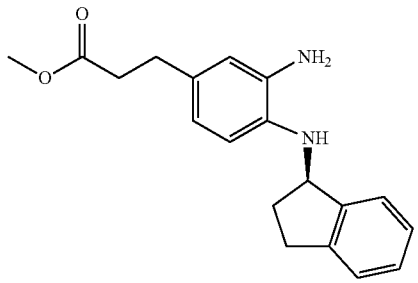 [SMILES: COC(=O)CCc1ccc(N[C@@H]2CCc3ccccc32)c(N)c1]

To a solution of Example 8A (720 mg, 2.13 mmol) in MeOH (20 mL) and DMF (5 mL), NiCl$_2$.6H$_2$O (2.02 g, 8.51 mmol) and NaBH$_4$ (563.54 mg, 14.90 mmol) were added in batches. The mixture was stirred at 0° C. for 1 hour. The reaction mixture was quenched by adding water (50 mL) and then diluted with ethyl acetate (50 mL). The mixture was filtered and extracted with ethyl acetate (30 mL×3). The combined organic layer was washed with brine (100 mL×1), dried over sodium sulfate, filtered and concentrated under reduced pressure to obtain Example 8B as a brown oil. The residue was used directly in the next step without further purification.

Example 8C

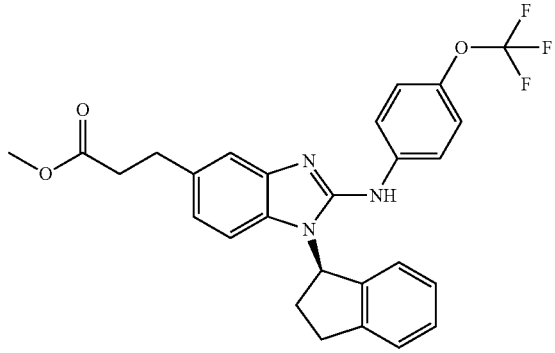 [SMILES: COC(=O)CCc1ccc2c(c1)nc(Nc1ccc(OC(F)(F)F)cc1)n2[C@@H]1CCc2ccccc21]

To a solution of Example 8B (800 mg, 2.58 mmol) in THF (10 mL) was added 4-(trifluoromethoxy)phenyl isothiocyanate (677.91 mg, 3.09 mmol, 502.16 μL). The mixture was stirred at 30° C. for 1 h. Then EDCI (988.19 mg, 5.15 mmol) was added and the mixture was stirred at 70° C. for 2 hours. The reaction mixture was diluted with water (30 mL) and extracted with ethyl acetate (20 mL×3). The combined organic layer was washed with brine (30 mL×1), dried over sodium sulfate, filtered and concentrated under reduced pressure to obtain a residue. The residue was purified by column chromatography to obtain Example 8C as a brown oil. $^1$H NMR (400 MHz, CDCl$_3$) δ=7.52-7.42 (m, 3H), 7.37-7.29 (m, 2H), 7.28-7.18 (m, 3H), 7.11 (br d, J=8.7 Hz, 2H), 7.03-6.93 (m, 1H), 6.06 (t, J=8.3 Hz, 1H), 3.70 (s, 3H), 3.30-3.20 (m, 1H), 3.16-3.09 (m, 1H), 3.06 (t, J=7.8 Hz, 2H), 2.82-2.73 (m, 1H), 2.70 (t, J=7.9 Hz, 2H), 2.34 (qd, J=8.8, 13.4 Hz, 1H).

Example 8

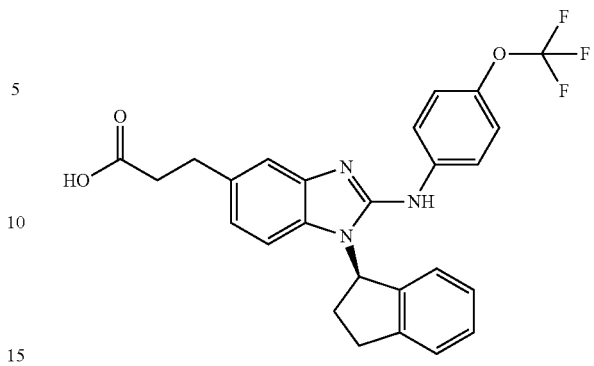

To a solution of Example 8C (450 mg, 908.19 μmol) in THF (2 mL) and H$_2$O (2 mL) was added LiOH.H$_2$O (114.33 mg, 2.72 mmol). The mixture was stirred at 20° C. for 16 hours. The mixture was adjusted to pH 7 with aqueous HCl (1M), and then extracted with ethyl acetate (10 mL×3). The combined organic layer was washed with brine (20 mL), dried over Na$_2$SO$_4$, filtered and concentrated under reduced pressure, and purified by high performance liquid chromatography to obtain Example 8. $^1$H NMR (400 MHz, METHANOL-d$_4$) δ=7.73-7.59 (m, 2H), 7.56-7.47 (m, 3H), 7.46-7.40 (m, 1H), 7.32-7.20 (m, 3H), 6.96 (d, J=8.3 Hz, 1H), 6.41-6.22 (m, 2H), 3.40-3.34 (m, 1H), 3.20 (td, J=8.5, 16.6 Hz, 1H), 2.99-2.93 (m, 2H), 2.92-2.84 (m, 1H), 2.62-2.55 (m, 2H), 2.55-2.46 (m, 1H).

Example 9

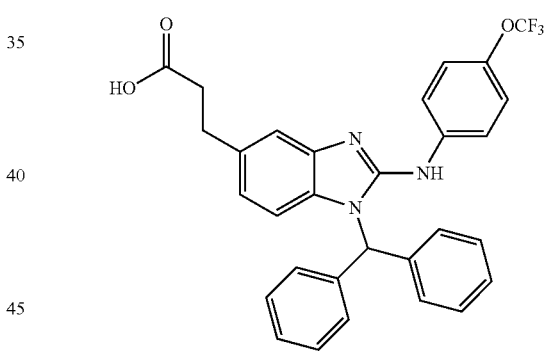

Example 9A

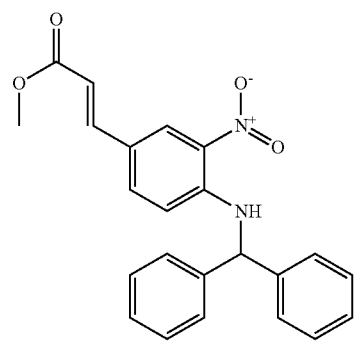 [SMILES: COC(=O)/C=C/c1ccc(NC(c2ccccc2)c2ccccc2)c([N+](=O)[O-])c1]

To a solution of methyl (E)-3-(4-fluoro-3-nitrophenyl) acrylate (0.5 g, 2.22 mmol) and diphenylmethylamine (447.60 mg, 2.44 mmol, 422.26 μL) in tetrahydrofuran (10 mL), potassium carbonate (613.78 mg, 4.44 mmol) was added, and the mixed solution was stirred at 50° C. for 12 hours. Then diphenylmethylamine (81.38 mg, 444.10 μmol, 76.77 μL) was added, and the solution was stirred at 55° C. for 12 hours. The reaction solution was diluted with 30 mL of water, and then extracted with ethyl acetate (30 mL×3). The combined organic phase was dried over anhydrous sodium sulfate, filtered, and concentrated under reduced pressure to obtain a crude product. The crude product was purified by column chromatography to obtain Example 9A as a yellow solid. $^1$H NMR (400 MHz, CDCl$_3$) δ=8.74 (br d, J=5.3 Hz, 1H), 8.27 (d, J=1.9 Hz, 1H), 7.48 (d, J=15.9 Hz, 1H), 7.42 (dd, J=1.8, 8.9 Hz, 1H), 7.32-7.20 (m, 10H), 6.69 (d, J=9.0 Hz, 1H), 6.19 (d, J=15.9 Hz, 1H), 5.70 (d, J=5.5 Hz, 1H), 3.71 (s, 3H).

Example 9B

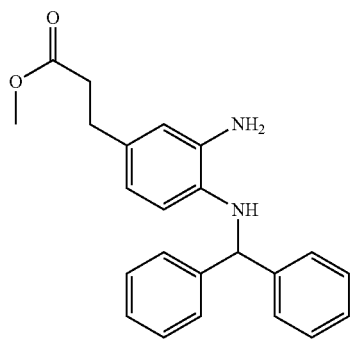 [SMILES: COC(=O)CCc1ccc(NC(c2ccccc2)c2ccccc2)c(N)c1]

Under the protection of nitrogen gas, nickel chloride (1.10 g, 8.50 mmol) was added to a solution of Example 9A (0.66 g, 1.70 mmol) in methanol (10 mL), and after cooling to 0° C., sodium borohydride (642.86 mg, 16.99 mmol) were added slowly. The mixed solution was stirred at 20° C. for 0.5 hour. The reaction was quenched by adding 50 mL of saturated ammonium chloride solution and stirring for 15 minutes. The reaction solution was extracted with ethyl acetate (50 mL×3), and the combined organic phase was dried over anhydrous sodium sulfate, filtered, and concentrated under reduced pressure to obtain Example 9B as a yellow oil, which was used directly in the next step without purification.

Example 9C

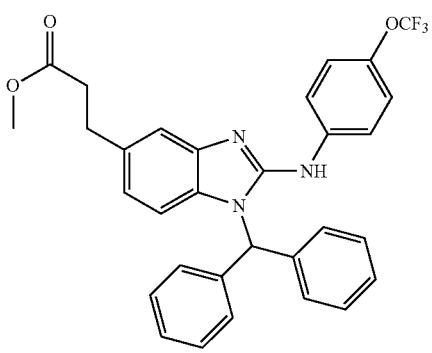 [SMILES: COC(=O)CCc1ccc2c(c1)nc(Nc1ccc(OC(F)(F)F)cc1)n2C(c1ccccc1)c1ccccc1]

To a solution of Example 9B (0.41 g, 1.14 mmol) in tetrahydrofuran (10 mL), 4-(trifluoromethoxy)phenyl isothiocyanate (278 mg, 1.27 mmol, 205.93 μL) was added and stirred at 40° C. for 1 hour. Then EDC.HCl (436.11 mg, 2.27 mmol) was added and stirred at 70° C. for 12 hours. The reaction solution was diluted with 30 mL of water, and then extracted with ethyl acetate (30 mL×3). The combined organic phase was dried over anhydrous sodium sulfate, filtered, and concentrated under reduced pressure to obtain a crude product, which was purified by column chromatography to obtain Example 9C as a yellow solid.

Example 9

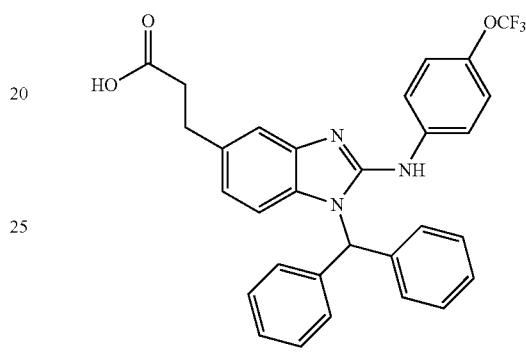

To a solution of Example 9C (0.46 g, 843.18 μmol) in tetrahydrofuran (5 mL) and water (5 mL), lithium hydroxide monohydrate (176.92 mg, 4.22 mmol) was added and stirred at 20° C. for 12 hours. The reaction solution was adjusted to pH 6 with 1M hydrochloric acid, and extracted with ethyl acetate (20 mL×3). The combined organic phase was dried over anhydrous sodium sulfate, filtered, and concentrated under reduced pressure to obtain a crude product. The crude product was diluted with 10 mL petroleum ether: ethyl acetate=10:1, stirred for 30 minutes, filtered and concentrated under reduced pressure to obtain Example 9. $^1$H NMR (400 MHz, DMSO-d6) δ=12.06 (br s, 1H), 9.33 (br s, 1H), 7.90 (br d, J=8.2 Hz, 2H), 7.46-7.35 (m, 7H), 7.32 (br d, J=8.7 Hz, 2H), 7.26 (br s, 1H), 7.20 (br d, J=7.1 Hz, 4H), 6.64 (br d, J=7.8 Hz, 1H), 6.28 (br d, J=8.2 Hz, 1H), 2.81 (br t, J=7.5 Hz, 2H), 2.53 (br s, 2H).

Example 10

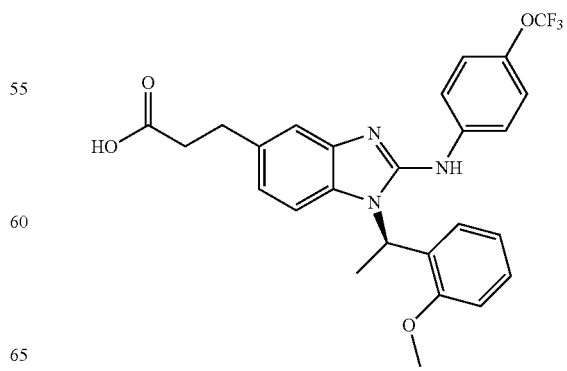

Example 10A

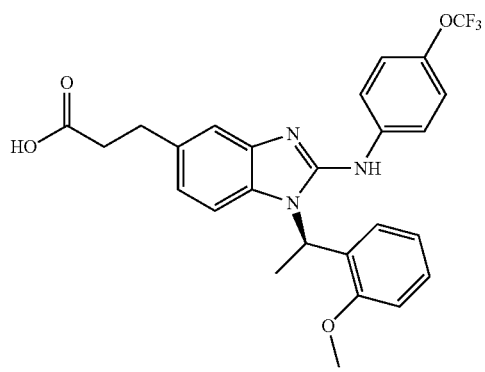 [SMILES: COc1ccccc1[C@@H](C)n1c(Nc2ccc(OC(F)(F)F)cc2)nc2cc(CCC(=O)O)ccc21]

To a solution of methyl (E)-3-(4-fluoro-3-nitro-phenyl)prop-2-enoate (750 mg, 3.33 mmol) in tetrahydrofuran (10 mL), potassium carbonate (920.67 mg, 6.66 mmol)) and (1R)-1-(2-methoxyphenyl)ethylamine (503.52 mg, 3.33 mmol) were added, and the mixture was stirred at 50° C. for 16 hours. The reaction mixture was concentrated under reduced pressure to remove the solvent. The residue was diluted with 100 mL of water and extracted with 200 mL (100 mL×2) of ethyl acetate. The combined organic layer was washed with 200 mL (100 mL×2) of saline solution, dried over anhydrous sodium sulfate, filtered and concentrated under reduced pressure to obtain a residue, and the residue was purified by column chromatography (SiO$_2$, petroleum ether/ethyl acetate=1/0 to 15:1) to obtain Example 10A.

Example 10B

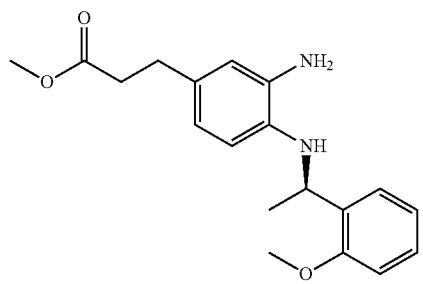 [SMILES: COC(=O)CCc1ccc(N[C@H](C)c2ccccc2OC)c(N)c1]

To a solution of Example 10A (1.19 g, 3.34 mmol) in methanol (10 mL), nickel chloride (3.97 g, 16.70 mmol) was added, and then a solution of sodium borohydride (1.39 g, 36.73 mmol) in dimethylformamide (5 mL) was added dropwise, while controlling the internal temperature not to exceed 10° C., and then the reaction mixture was stirred at 10° C. for 16 hours. The mixture was poured into water (100 mL), and ethyl acetate (40 mL) and filtered through a pad of celite. The filter cake was washed with ethyl acetate (60 mL×3) and the filtrate was extracted with 150 mL of ethyl acetate. The combined organic phases was washed with saturated brine (100 mL×2), dried over anhydrous sodium sulfate and concentrated in vacuo to obtain Example 10B.

Example 10C

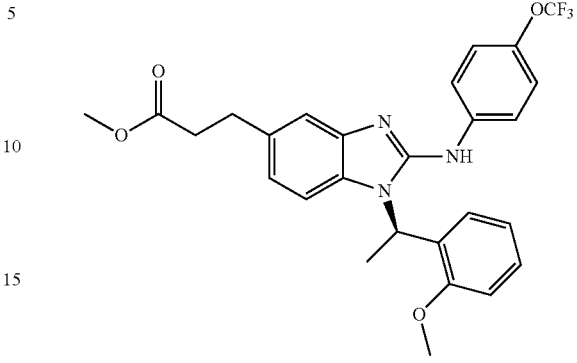

To a solution of Example 10B (1.11 g, 3.35 mmol) in tetrahydrofuran (15 mL), 1-isothiocyanoyl-4-(trifluoromethoxy)benzene (734.27 mg, 3.35 mmol, 543.90 μL) was added, and the mixture was stirred at 50° C. for 1 hour, then EDCI (642.11 mg, 3.35 mmol) was added and the mixture was stirred at 70° C. for 15 hours. The reaction mixture was concentrated under reduced pressure to remove the solvent. The residue was diluted with 100 mL of water and extracted with 200 mL (100 mL×2) of ethyl acetate. The combined organic layer was washed with 200 mL (100 mL×2) of saturated saline solution, dried over anhydrous sodium sulfate, filtered and concentrated under reduced pressure to obtain a residue. The residue was purified by column chromatography (SiO$_2$, petroleum ether/ethyl acetate=1/0 to 6:1) to obtain Example 10C.

Example 10

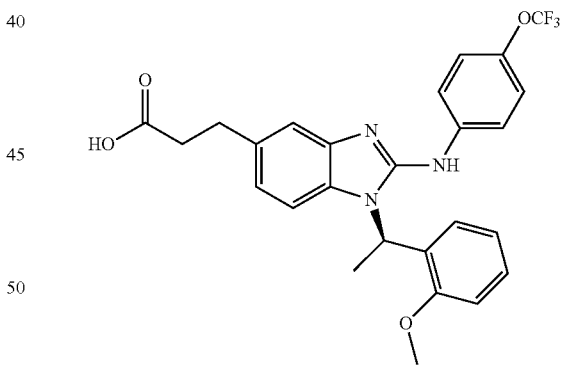

To a solution of Example 10C (1.32 g, 2.49 mmol) in tetrahydrofuran (6 mL) and water (3 mL), lithium hydroxide monohydrate (523.12 mg, 12.47 mmol) was added and the mixture was stirred at 25° C. for 16 hours. The mixture was acidified with dilute hydrochloric acid (1N, 4 ml) to pH=6, and extracted with 200 mL (100 mL×2) of ethyl acetate. The combined organic layer was washed with 200 mL (100 mL×2) of saturated saline solution, and dried over anhydrous sodium sulfate, filtered and concentrated under reduced pressure. The resulting residue was dissolved in a mixed solution of ethyl acetate (4 mL) and petroleum ether (8 mL) and stirred at 25° C. for 60 minutes. The mixture was filtered and the filter cake was washed with a mixed solution of ethyl acetate (1 mL) and petroleum ether (2 mL), to obtain Example 10. ¹H NMR (400 MHz, CDCl₃) δ=7.60-7.55 (m, 2H), 7.37-7.32 (m, 1H), 7.28-7.22 (m, 3H), 7.09-7.03 (m, 3H), 6.98 (dd, J=1.5, 8.3 Hz, 1H), 6.86 (d, J=8.3 Hz, 1H), 5.78 (q, J=7.1 Hz, 1H), 3.70 (s, 3H), 3.13-2.98 (m, 2H), 2.75-2.61 (m, 2H), 1.88 (d, J=7.1 Hz, 3H).

Example 11

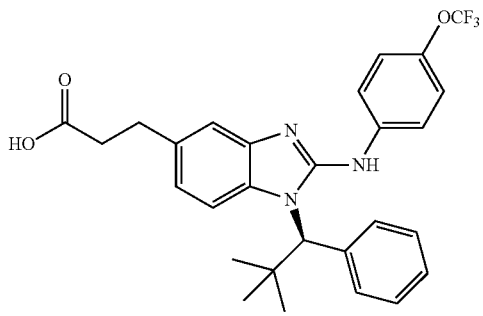 [SMILES: CC(C)(C)[C@H](c1ccccc1)n1c(Nc2ccc(OC(F)(F)F)cc2)nc2cc(CCC(=O)O)ccc21]

Example 11A

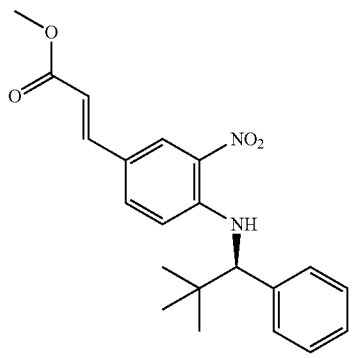 [SMILES: COC(=O)/C=C/c1ccc(N[C@@H](c2ccccc2)C(C)(C)C)c([N+](=O)[O-])c1]

To a solution of methyl (E)-3-(4-Fluoro-3-nitro-phenyl) prop-2-enoate (220 mg, 977.03 µmol) in tetrahydrofuran (10 mL), potassium carbonate (675.15 mg, 2.931 mmol) and (1R)-2,2-dimethyl-1-phenyl-prop-1-amine hydrochloride (195.13 mg, 977.03 µmol) were added. The mixture was stirred at 60° C. for 48 hours. The reaction mixture was concentrated under reduced pressure to remove the solvent. The residue was diluted with 100 mL of water and extracted with 200 mL (100 mL×2) of ethyl acetate. The combined organic layer was washed with 200 mL (100 mL×2) of saturated saline solution, dried over anhydrous sodium sulfate, filtered and concentrated under reduced pressure to obtain a residue. The residue was purified by column chromatography (SiO₂, petroleum ether/ethyl acetate=1/0 to 12:1) to obtain Example 11A.

Example 11B

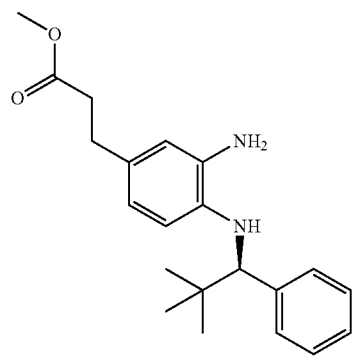 [SMILES: COC(=O)CCc1ccc(N[C@@H](c2ccccc2)C(C)(C)C)c(N)c1]

To a solution of Example 11A (420 mg, 1.14 mmol) in methanol (6 mL), nickel chloride (1.35 g, 5.70 mmol) was added and then a solution of sodium borohydride (474.42 mg, 12.54 mmol) in dimethylformamide (3 mL) was added dropwise, while controlling the internal temperature not to exceed 10° C., and then the reaction mixture was stirred at 10° C. for 2 hours. The mixture was poured into water (80 mL), ethyl acetate (20 mL) and filter through a pad of celite. The filter cake was washed with ethyl acetate (50 mL×3), and the mixture was extracted with 100 mL of ethyl acetate. The combined organic phase was washed with saturated brine (80 mL×2), dried over anhydrous sodium sulfate and concentrated in vacuo to obtain Example 11B, which was used directly in the next step without purification.

Example 11C

To a solution of Example 11B (270 mg, 793.05 µmol) in tetrahydrofuran (5 mL), 1-isothiocyanato-4-(trifluoromethoxy)benzene (173.82 mg, 793.05 µmol, 128.76 µL) was added and the mixture was stirred at 50° C. for 1 hour, then EDCI (167.23 mg, 872.35 µmol) was added and the mixture was stirred at 70° C. for 15 hours. The reaction mixture was concentrated under reduced pressure to remove the solvent. The residue was diluted with 100 mL of water and extracted with 200 mL of ethyl acetate (100 mL×2). The combined organic layer was washed with 200 mL of saturated saline solution (100 mL×2), dried over anhydrous sodium sulfate, filtered and concentrated under reduced pressure to obtain a residue, which was purified by column chromatography (SiO₂, petroleum ether/ethyl acetate=1/0 to 10:1) to obtain Example 11C.

Example 11

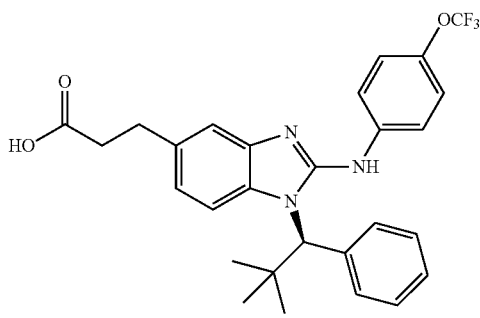 [SMILES: CC(C)(C)[C@H](c1ccccc1)n1c(Nc2ccc(OC(F)(F)F)cc2)nc2cc(CCC(=O)O)ccc21]

To a solution of Example 11C (373 mg, 695.52 μmol) in tetrahydrofuran (3 mL) and water (1 mL), lithium hydroxide (145.93 mg, 3.48 mmol) was added, and the mixture was stirred at 25° C. for 6 hours. The mixture was acidified to pH=6 with dilute hydrochloric acid (1 N, 3 ml), filtered, and the filter cake was washed with 20 mL of ethyl acetate to obtain a residue. The filter cake was dissolved in methanol (10 mL) and dichloromethane (10 mL), the mixture was stirred at 80° C. for 1 hour, and then filtered. The filter cake was the product Example 11. $^1$H NMR (400 MHz, DMSO-d6) δ=9.17 (s, 1H), 7.96 (br d, J=9.0 Hz, 2H), 7.62 (br d, J=7.6 Hz, 2H), 7.41-7.33 (m, 4H), 7.31-7.25 (m, 1H), 7.18 (s, 1H), 6.76 (d, J=8.3 Hz, 1H), 6.63 (dd, J=1.4, 8.4 Hz, 1H), 5.86 (s, 1H), 2.78 (br t, J=7.6 Hz, 2H), 2.47-2.52 (m, 2H), 1.22 (s, 9H).

Example 12

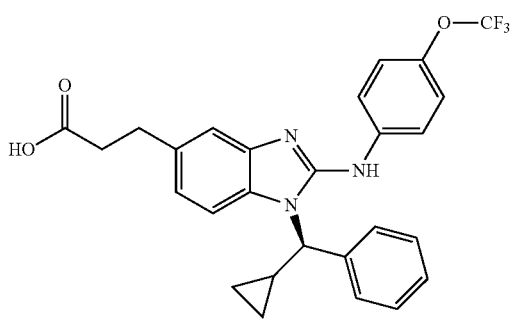 [SMILES: O=C(O)CCc1ccc2c(c1)nc(Nc1ccc(OC(F)(F)F)cc1)n2[C@@H](c1ccccc1)C1CC1]

Example 12A

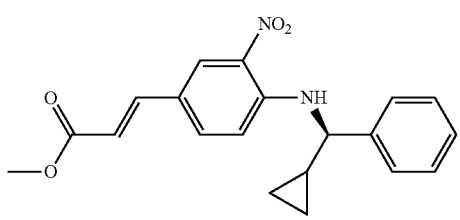 [SMILES: COC(=O)/C=C/c1ccc(N[C@@H](c2ccccc2)C2CC2)c([N+](=O)[O-])c1]

Methyl (E)-3-(4-Fluoro-3-nitro-phenyl)prop-2-enoate (0.26 g, 1.15 mmol) was dissolved in acetonitrile (10 mL), then potassium carbonate (558.55 mg, 3.45 mmol) and (R)-cyclopropyl(phenyl)methylamine hydrochloride (233.30 mg, 1.27 mmol) were added and stirred at 80° C. for 2 hours. The reaction mixture was diluted with 100 mL of water and extracted with 100 mL (50 mL×2) of ethyl acetate. The combined organic layer was washed with 50 mL (50 mL×1) of brine, dried over sodium sulfate, filtered and concentrated under reduced pressure, and purified by column chromatography to obtain Example 12 as a yellow oil. $^1$H NMR (400 MHz, CDCl$_3$) δ=0.34-0.56 (m, 2H), 0.60-0.80 (m, 2H), 1.30-1.43 (m, 1H), 3.78 (s, 3H), 4.04 (dd, J=7.95, 5.38 Hz, 1H), 6.23 (d, J=15.89 Hz, 1H), 6.56 (d, J=8.93 Hz, 1H), 6.52-6.62 (m, 1H), 7.27-7.42 (m, 6H), 7.53 (d, J=15.89 Hz, 1H), 8.32 (d, J=2.08 Hz, 1H), 8.88 (br d, J=5.01 Hz, 1H).

Example 12B

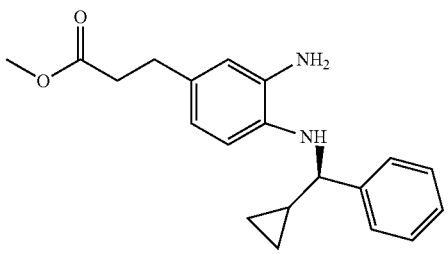 [SMILES: COC(=O)CCc1ccc(N[C@@H](c2ccccc2)C2CC2)c(N)c1]

To Example 12A (388 mg, 1.10 mmol) and nickel chloride hexahydrate (1.31 g, 5.51 mmol), MeOH (6 mL) and THF (6 mL) were added, and sodium borohydride (416.54 mg, 11.01 mmol) was added in batches at 5° C., and stirred at 5° C. for 0.5 hours. The reaction mixture was quenched by adding 100 mL of water, filtered, and the filtrate was extracted with 100 mL (50 mL×2) of ethyl acetate. The combined organic layer was washed with 50 mL (50 mL×1) of brine, dried over sodium sulfate, filtered, and concentrated under reduced pressure to obtain Example 12B.

Example 12C

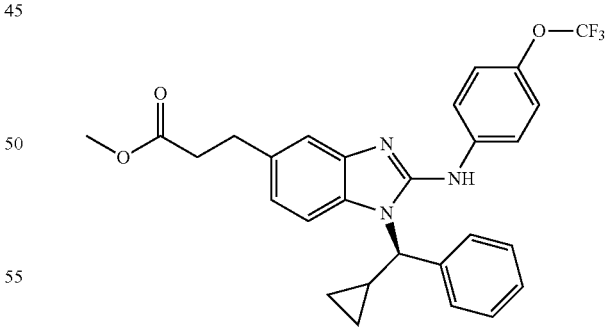

To a solution of Example 12B (280 mg, 863.09 μmol) in THF (15 mL), isothiocyanoyl-4-(trifluoromethoxy)benzene (227.01 mg, 1.04 mmol, 168.16 μL) was added. After the addition, the mixture was stirred at 40° C. for 1 hour, and then EDCI (330.91 mg, 1.73 mmol) was added and stirred at 70° C. for 1 hour. The reaction mixture was concentrated under reduced pressure to remove THF, diluted with 80 mL of water and extracted with 100 mL (50 mL×2) of ethyl acetate. The combined organic layer was washed with 50 mL (50 mL×1) of brine, dried over sodium sulfate, filtered, and concentrated under reduced pressure, and purified by column chromatography to obtain Example 12C as a colorless oil. ¹H NMR (400 MHz, CDCl₃) δ=0.47-0.70 (m, 3H), 0.95-1.07 (m, 1H), 1.74-1.83 (m, 1H), 2.70 (t, J=7.89 Hz, 2H), 3.06 (t, J=7.95 Hz, 2H), 3.69 (s, 3H), 4.84 (d, J=9.54 Hz, 1H), 6.97 (dd, J=8.19, 1.34 Hz, 1H), 7.05-7.16 (m, 3H), 7.28-7.33 (m, 2H), 7.40-7.54 (m, 6H).

Example 12

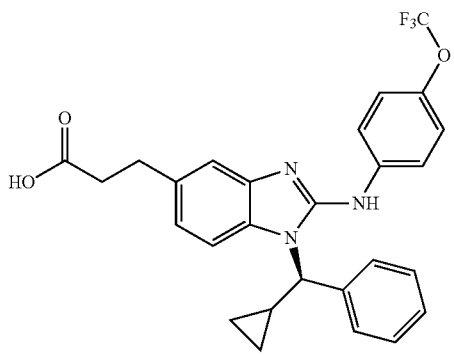 [SMILES: O=C(O)CCc1ccc2c(c1)nc(Nc1ccc(OC(F)(F)F)cc1)n2[C@@H](c1ccccc1)C1CC1]

To a solution of Example 12C (0.29 g, 569.16 µmol) in THF (3 mL), MeOH (3 mL) and H₂O (3 mL), lithium hydroxide monohydrate (119.41 mg, 2.85 mmol) was added and stirred at 20° C. for 16 hours. The reaction mixture was slowly adjusted to pH=4 with 1N HCl solution, and extracted with ethyl acetate (40 mL×2). The combined organic layer was washed with 50 mL of brine, dried over sodium sulfate, filtered and concentrated under reduced pressure, stirred with MeOH (10 mL), filtered, and dried under vacuum to obtain Example 12. ¹H NMR (400 MHz, CDCl₃) δ=4.38 (br s, 1H), 4.79-4.97 (m, 1H), 6.51-6.62 (m, 2H), 7.25-7.27 (m, 1H), 7.27-7.29 (m, 1H), 7.38-7.51 (m, 5H).

Example 13

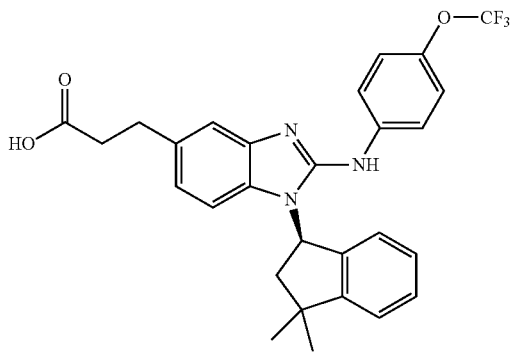 [SMILES: CC1(C)C[C@@H](n2c(Nc3ccc(OC(F)(F)F)cc3)nc3cc(CCC(=O)O)ccc32)c2ccccc21]

Example 13A

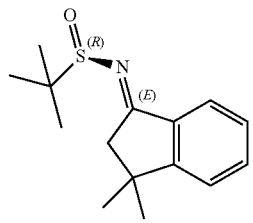

3,3-Dimethylinden-1-one (3 g, 18.73 mmol) was dissolved in toluene (40 mL), into which titanium tetraisopropoxide (10.64 g, 37.46 mmol, 11.05 mL) and 2-methylpropane-2-sulfinamide (2.72 g, 22.48 mmol) were added, stirred at 60° C. for 24 hours, then 2-methylpropane-2-sulfinamide (2.72 g, 22.48 mmol) and titanium tetraisopropoxide (5.32 g, 18.73 mmol, 5.53 mL) were further added and stirred at 110° C. for 16 hours. The reaction mixture was quenched by adding 200 mL of water, and then filtered. The filtrate was extracted with 160 mL (80 mL×2) of ethyl acetate. The combined organic layer was washed with 80 mL (80 mL×1) of brine, dried over sodium sulfate, filtered, and concentrated under reduced pressure, and purified by column chromatography to obtain compound Example 13A as a brown oil. ¹H NMR (400 MHz, CDCl₃) δ=1.29-1.43 (m, 15H) 2.98 (d, J=19.07 Hz, 1H) 3.34 (d, J=19.20 Hz, 1H) 7.29-7.42 (m, 2H) 7.48-7.58 (m, 1H) 7.76 (d, J=7.70 Hz, 1H).

Example 13B

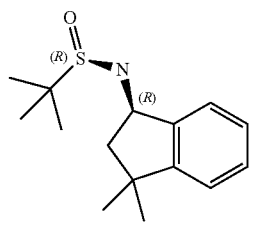

Example 13A (1.4 g, 5.32 mmol) was dissolved in THF (20 mL) and water (574.67 mg, 31.89 mmol, 574.67 µL), into which sodium borohydride (1.01 g, 26.58 mmol) was added, and the mixture was stirred at 25° C. for 4 hours. The reaction mixture was quenched by adding 100 mL of water, and then extracted with 100 mL (50 mL×2) of ethyl acetate. The combined organic layer was washed with 50 mL of saturated saline solution, dried over sodium sulfate, filtered and concentrated under reduced pressure, and purified by column chromatography to obtain compound Example 13B as a white solid. ¹H NMR (400 MHz, CDCl₃) δ=1.21-1.28 (m, 12H) 1.38 (s, 3H) 1.88 (dd, J=12.84, 7.46 Hz, 1H) 2.37 (dd, J=12.84, 7.21 Hz, 1H) 3.49 (br d, J=6.60 Hz, 1H) 4.88-4.99 (m, 1H) 7.14-7.21 (m, 1H) 7.23-7.29 (m, 2H) 7.51-7.60 (m, 1H).

Example 13C (1R)-3,3-Dimethylinden-1-amine

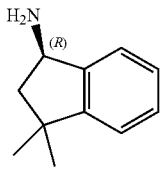

Example 13E

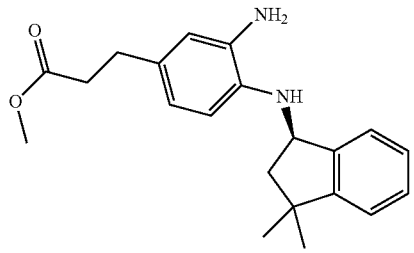

To a solution of Example 13B (810 mg, 3.05 mmol) in MeOH (8 mL), HCl/dioxane (4M, 3 mL) was added and stirred at 20° C. for 0.5 hours. The mixture was diluted with methyl tert-butyl ether (15 mL) and stirred at 25° C. for 30 minutes, filtered, and dried in vacuum to obtain Example 13C as a white solid. $^1$H NMR (400 MHz, METHANOL-d4) δ=1.15-1.30 (m, 3H) 1.40-1.50 (m, 3H) 1.93 (dd, J=13.02, 8.13 Hz, 1H) 2.53 (dd, J=12.96, 7.70 Hz, 1H) 3.31 (dt, J=3.30, 1.65 Hz, 1H) 7.21-7.59 (m, 4H).

Example 13D (300 mg, 818.75 μmol) was dissolved in THF (5 mL) and MeOH (5 mL), into which Pd/C (50 mg, 10%) was added, the atmosphere was replaced with hydrogen gas for 3 times, and the mixture was stirred at 25° C. under H$_2$ (15 psi) for 16 hours. After filtration, the filtrate was concentrated under reduced pressure to obtain Example 13E as a brown oil.

Example 13D

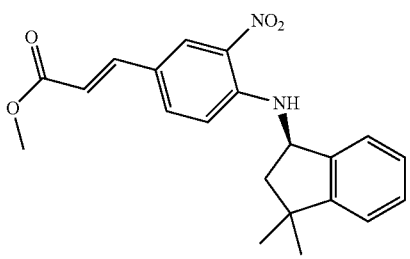 [SMILES: COC(=O)/C=C/c1ccc(N[C@@H]2CC(C)(C)c3ccccc32)c([N+](=O)[O-])c1]

Example 13F

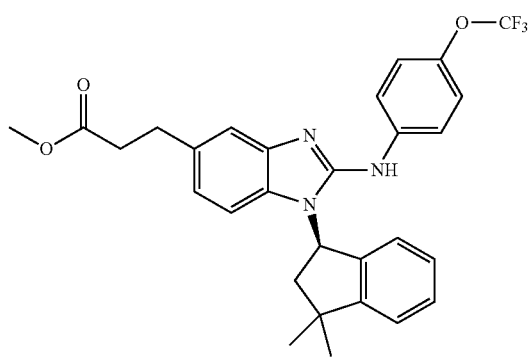 [SMILES: COC(=O)CCc1ccc2c(c1)nc(Nc1ccc(OC(F)(F)F)cc1)n2[C@@H]1CC(C)(C)c2ccccc21]

To a solution of methyl (E)-3-(4-fluoro-3-nitro-phenyl)prop-2-enoate (400 mg, 1.78 mmol) in THF (12 mL), potassium carbonate (982.04 mg, 7.11 mmol) and Example 13C (491.69 mg, 2.49 mmol) were added and stirred at 65° C. for 16 hours. The mixture was diluted with 100 mL of water and extracted with 120 mL (60 mL×2) of ethyl acetate. The combined organic layer was washed with 50 mL (50 mL×1) of brine, dried over sodium sulfate, filtered and concentrated under reduced pressure, and purified by column chromatography to obtain Example 13D as a yellow oil. $^1$H NMR (400 MHz, CDCl$_3$) δ=1.33 (s, 3H) 1.43 (s, 3H) 1.95 (dd, J=12.72, 7.34 Hz, 1H) 2.60 (dd, J=12.65, 7.15 Hz, 1H) 3.82 (s, 3H) 5.25 (q, J=7.21 Hz, 1H) 6.34 (d, J=15.89 Hz, 1H) 7.14 (d, J=9.05 Hz, 1H) 7.25-7.27 (m, 1H) 7.27-7.29 (m, 1H) 7.30-7.39 (m, 2H) 7.57-7.73 (m, 2H) 8.38 (d, J=2.20 Hz, 1H) 8.57 (br d, J=7.09 Hz, 1H)

Example 13E (255 mg, 753.45 μmol) was dissolved in THF (8 mL), into which 1-isothiocyanoyl-4-(trifluoromethoxy)benzene (198.17 mg, 904.14 μmol, 146.79 μL) was added and stirred at 40° C. for 1 hour, then EDCI (288.87 mg, 1.51 mmol) was added and stirred at 70° C. for 1 hour. The reaction mixture was concentrated under reduced pressure to remove THF, diluted with 80 mL of water and extracted with 100 mL (50 mL×2) of ethyl acetate. The combined organic layer was washed with 50 mL (50 mL×1) of brine, dried over sodium sulfate, filtered and concentrated under reduced pressure, and purified by column chromatography, and then subjected to chiral resolution to obtain Example 13F as a white solid compound. $^1$H NMR (400 MHz, CDCl$_3$) δ=1.28-1.55 (m, 6H) 2.14-2.72 (m, 4H) 3.06 (br s, 2H) 3.69 (s, 3H) 5.50 (br s, 1H) 6.06 (br s, 1H) 6.92-7.60 (m, 11H).

Example 13

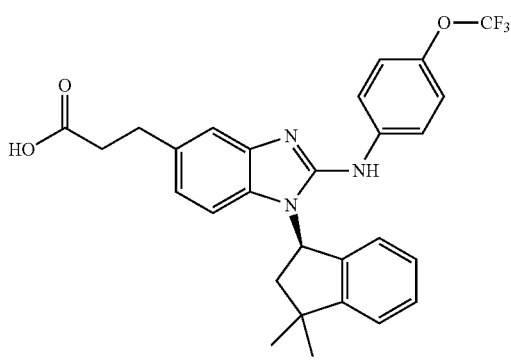 [SMILES: CC1(C)C[C@@H](n2c(Nc3ccc(OC(F)(F)F)cc3)nc3cc(CCC(=O)O)ccc32)c2ccccc21]

To a solution of Example 13F (180 mg, 343.81 μmol) in MeOH (2Ml), lithium hydroxide monohydrate (43.28 mg, 1.03 mmol), THF (2 mL) and H$_2$O (2 mL) were added and stirred at 25° C. for 1 hour. The reaction mixture was slowly adjusted to pH=4 with 1N HCl, and then the precipitate was collected by filtration and dried under vacuum to obtain Example 13. $^1$H NMR (400 MHz, METHANOL-d4) δ=1.34 (s, 3H) 1.54 (s, 3H) 2.37 (dd, J=12.65, 9.48 Hz, 1H) 2.48-2.63 (m, 3H) 2.90 (br t, J=7.58 Hz, 2H) 6.05-6.37 (m, 2H) 6.69 (br d, J=8.07 Hz, 1H) 6.93 (br d, J=7.58 Hz, 1H) 7.14-7.32 (m, 4H) 7.35-7.42 (m, 2H) 7.59 (br d, J=7.58 Hz, 2H).

Example 14 and Example 15

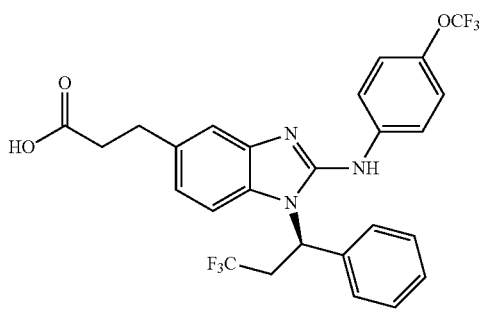 [SMILES: O=C(O)CCc1ccc2c(c1)nc(Nc1ccc(OC(F)(F)F)cc1)n2[C@H](CC(F)(F)F)c1ccccc1]

Example 14A

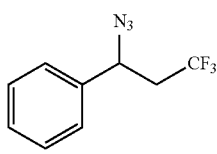 [SMILES: [N-]=[N+]=NC(CC(F)(F)F)c1ccccc1]

A dry bottle was filled with 1-(trifluoromethyl)-1,2-benzoiodo-3-one (3.28 g, 10.37 mmol) and CuBr (123.96 mg, 864.15 μmol, 26.32 μL). The bottle was evacuated and backfilled with nitrogen gas for three times. Then, azido (trimethyl)silane (2.49 g, 21.60 mmol, 2.84 mL) and styrene (900 mg, 8.64 mmol) dissolved in ACN (40 mL) were added to the above bottle. The reaction mixture was stirred at 40° C. for 1.5 hours. The reaction mixture was diluted with water (40 mL) and extracted with DCM (20 mL×3). The combined organic layer was washed with brine (20 mL×1), dried over Na$_2$SO$_4$, filtered and concentrated under reduced pressure to obtain a residue, which was purified by column chromatography to obtain Example 14A as a colorless oily compound. $^1$H NMR (400 MHz, CDCl$_3$) δ=7.50-7.36 (m, 5H), 4.81 (dd, J=5.1, 8.4 Hz, 1H), 2.73-2.45 (m, 2H).

Example 14B

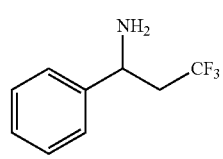 [SMILES: NC(CC(F)(F)F)c1ccccc1]

To a solution of Example 14A (1.1 g, 5.11 mmol) in MeOH (15 mL), CuSO$_4$ (81.59 mg, 511.21 μmol, 78.46 μL) and NaBH$_4$ (290.11 mg, 7.67 mmol) were added. The mixture was stirred at 0° C. for 1 h and then at 20° C. for 16 h. The reaction mixture was diluted with water (20 mL) and extracted with ethyl acetate (20 mL×3). The combined organic layer was washed with brine (20 mL×2), dried over anhydrous sodium sulfate, filtered and concentrated under reduced pressure to obtain Example 14B as a brown oil, which was used in the next step without further purification.

Example 14C

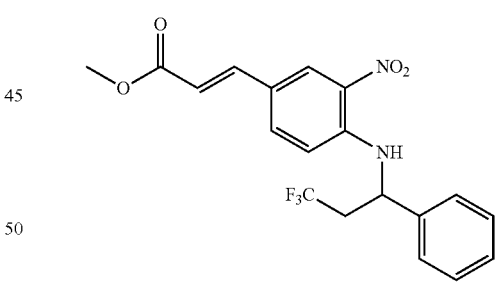

To a solution of methyl (E)-3-(4-fluoro-3-nitro-phenyl) prop-2-enoate (600 mg, 2.66 mmol) in THF (10 mL), K$_2$CO$_3$ (1.10 g, 7.99 mmol) and Example 14B (720 mg, 3.81 mmol) were added. The mixture was stirred at 50° C. for 16 hours. The mixture was then stirred at 70° C. for 32 hours. The reaction mixture was concentrated under reduced pressure to remove the solvent. The residue was diluted with water (50 mL) and extracted with ethyl acetate (50 mL×3). The combined organic layer was washed with brine (50 mL), dried over Na$_2$SO$_4$, filtered and concentrated under reduced pressure to obtain the crude product Example 14C as a yellow oil, which was used in the next step without further purification.

Example 14D

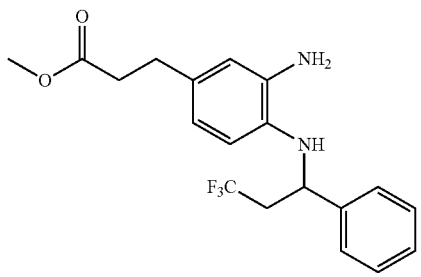 [SMILES: COC(=O)CCc1ccc(NC(CC(F)(F)F)c2ccccc2)c(N)c1]

To a solution of Example 14C (1 g, 2.54 mmol) in MeOH (20 mL), $NiCl_2 \cdot 6H_2O$ (2.41 g, 10.14 mmol) was added, and then $NaBH_4$ (959.38 mg, 25.36 mmol) was added in portions at 0° C., and the mixture was kept at 0° C. for 1 hour. The reaction mixture was diluted with water (50 mL) and extracted with ethyl acetate (50 mL×3). The combined organic layer was washed with brine (50 mL×1), dried over $Na_2SO_4$, filtered and concentrated under reduced pressure to obtain Example 14D as a brown oily residue, which was used directly in the next step without further purification.

Example 14E and Example 14F

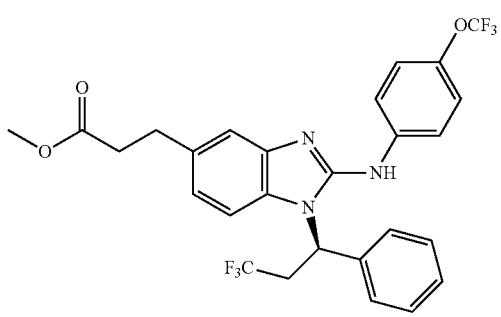

Example 14E or Example 14F

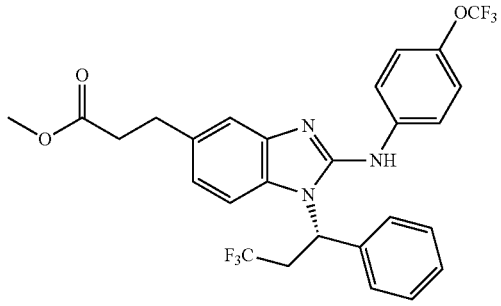

Example 14E or Example 14F

To Example 14D (770 mg, 2.10 mmol) in THF (20 mL), 1-isothiocyanoyl-4-(trifluoromethoxy)benzene (552.78 mg, 2.52 mmol, 409.47 µL) was added. The mixture was stirred at 40° C. for 1 h. Then EDCI (805.79 mg, 4.20 mmol) was added and the mixture was stirred at 70° C. for 2 hours. The reaction mixture was diluted with water (50 mL) and extracted with ethyl acetate (30 mL×3). The combined organic layer was washed with brine (50 mL), dried over $Na_2SO_4$, filtered and concentrated under reduced pressure to obtain a residue, which was purified by column chromatography to obtain a residue. The residue was separated by SFC (chiral column: Chiralcel OD-3 50×4.6 mm ID, 3 µm; mobile phase: A: $CO_2$, B: methanol (containing 0.05% DEA); gradient: methanol 5% to 40%; flow rate: 3 mL per minute; wavelength: 220 nm) to obtain Example 14E (retention time RT=1.546 minutes) and Example 14F (retention time RT=1.941 minutes).

Example 14 and Example 15

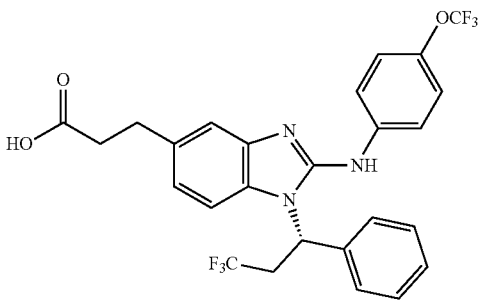

Example 14 or Example 15

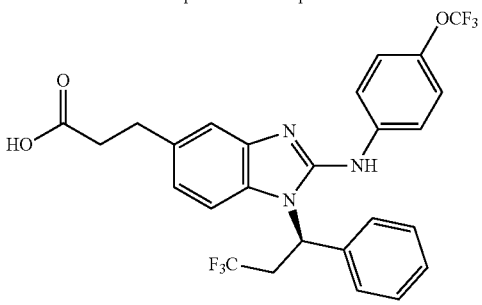

Example 14 or Example 15

To a solution of Example 14E (220 mg, 398.93 µmol) in MeOH (3 mL) and $H_2O$ (3 mL), $LiOH \cdot H_2O$ (50.22 mg, 1.20 mmol) was added. The mixture was stirred at 30° C. for 16 h. The mixture was stirred at 30° C. for another 3 hours. The mixture was adjusted to pH 5-6 with HCl (1M) solution to precipitate a solid, which was filtered and dried to obtain Example 14. $^1H$ NMR (400 MHz, METHANOL-d4) δ=7.57-7.47 (m, 2H), 7.43 (d, J=4.4 Hz, 4H), 7.38-7.33 (m, 1H), 7.30 (s, 1H), 7.25 (d, J=8.3 Hz, 2H), 6.88 (d, J=0.6 Hz, 2H), 6.30 (dd, J=3.6, 10.5 Hz, 1H), 3.61-3.37 (m, 2H), 2.96 (t, J=7.7 Hz, 2H), 2.61 (t, J=7.7 Hz, 2H).

To a solution of Example 14F (300 mg, 543.99 µmol) in MeOH (4 mL) and $H_2O$ (4 mL), $LiOH \cdot H_2O$ (68.48 mg, 1.63 mmol) was added. The mixture was stirred at 30° C. for 16 hours. The mixture was adjusted to pH 5-6 with HCl (1M) solution to precipitate a solid, which was filtered and dried to obtain Example 15. $^1H$ NMR (400 MHz, METHANOL-d4) δ=7.55-7.49 (m, 2H), 7.43 (d, J=4.4 Hz, 4H), 7.38-7.33 (m, 1H), 7.30 (s, 1H), 7.28-7.21 (m, 2H), 6.87 (s, 2H), 6.30 (dd, J=3.5, 10.5 Hz, 1H), 3.56-3.41 (m, 2H), 2.96 (t, J=7.6 Hz, 2H), 2.61 (t, J=7.7 Hz, 2H).

Experimental Example 1: IDH1 In Vitro Enzyme Activity Test

The IDH1 mutant catalyzes the NADPH-dependent reduction of α-KG (α-ketoglutarate) to 2-HG (2-hydroxyglutarate), and the consumed NADPH can be read by fluorescence.

Reagents:

Basic reaction buffer: 50 mM $KH_2PO_4$, pH 7.5, 10 mM $MgCl_2$, 10% glycerol, 150 mM NaCl, 0.05% BSA (bovine serum albumin), 2 mM b-ME (2-mercaptoethanol), 0.003% Brij35 (polyethylene glycol lauryl ether)

Substrates and cofactors:
IDH1 wt (wild type): 65 µM isocitrate+50 µM NADP
IDH1(R132H): 1500 µM α-KG+15 µM NADPH
IDH1(R132C): 500 µM α-KG+15 µM NADPH Reaction Process:

1.33× enzyme (no enzyme in the control well), buffer, and NADP or NADPH (control well) were added into the wells of the reaction plate. The test compound was dissolved in 100% DMSO and then added to the enzyme mixture (Echo550, nanoliter level), and incubated for 60 minutes after simple centrifugation. A mixture of 4× substrate and cofactor were added to start the reaction. After simple centrifugation, the plate was incubated under shaking at room temperature for 45 minutes. A mixture of 3× lipoamide dehydrogenase and Resazurin was prepared, added to the reaction solution to test the amount of NADPH generated or remaining, and incubated at room temperature for 10 minutes after simple centrifugation. Multifunctional microplate reader Envision was used to measure (Ex/Em=535/590 nm).

The experimental results are shown in Table 1 and Table 2:

TABLE 1

IDH1 in vitro enzyme (IDH1R132H) activity $IC_{50}$ test results

| Example | Structure | IDH1 R132H (nM) |
|---|---|---|
| Example 1 | 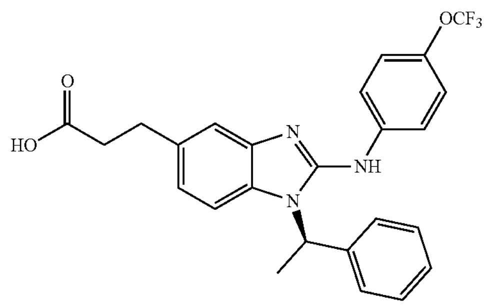 [SMILES: C[C@H](c1ccccc1)n1c(Nc2ccc(OC(F)(F)F)cc2)nc2cc(CCC(=O)O)ccc21] | 7.9 |
| Example 2 | 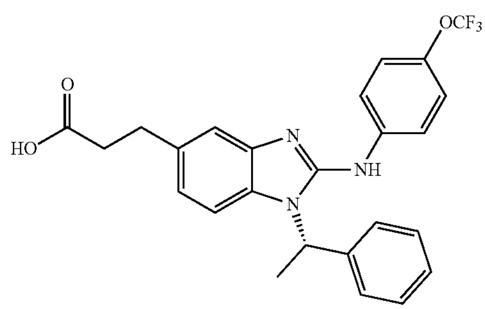 [SMILES: C[C@@H](c1ccccc1)n1c(Nc2ccc(OC(F)(F)F)cc2)nc2cc(CCC(=O)O)ccc21] | 464.5 |
| Example 3 | 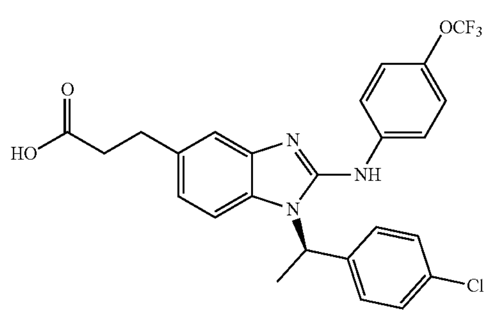 [SMILES: C[C@H](c1ccc(Cl)cc1)n1c(Nc2ccc(OC(F)(F)F)cc2)nc2cc(CCC(=O)O)ccc21] | 320 |

TABLE 1-continued

IDH1 in vitro enzyme (IDH1R132H) activity IC$_{50}$ test results

| Example | Structure | IDH1 R132H (nM) |
|---|---|---|
| Example 4 | 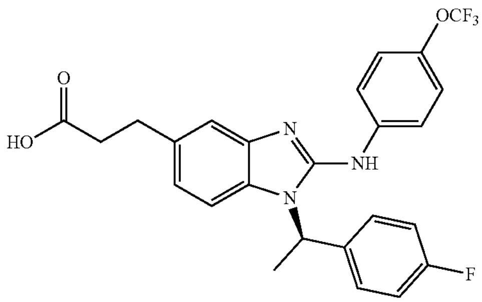 [SMILES: C[C@H](c1ccc(F)cc1)n1c(Nc2ccc(OC(F)(F)F)cc2)nc2cc(CCC(=O)O)ccc21] | 125.5 |
| Example 5 | 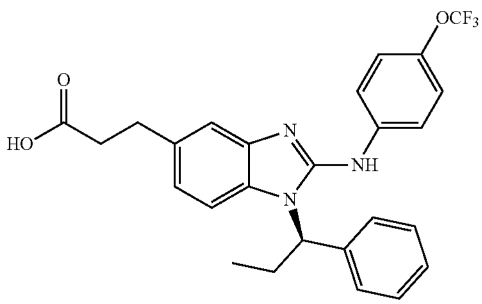 [SMILES: CC[C@H](c1ccccc1)n1c(Nc2ccc(OC(F)(F)F)cc2)nc2cc(CCC(=O)O)ccc21] | 89.53 |
| Example 6 | 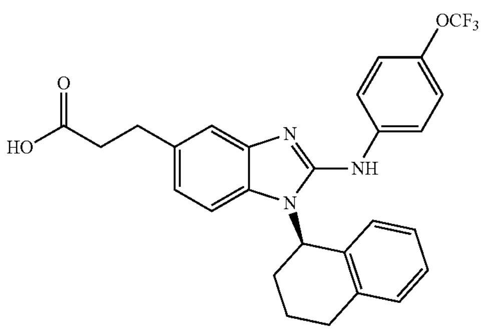 [SMILES: O=C(O)CCc1ccc2c(c1)nc(Nc1ccc(OC(F)(F)F)cc1)n2[C@@H]1CCCc2ccccc21] | 3.94 |
| Example 7 | 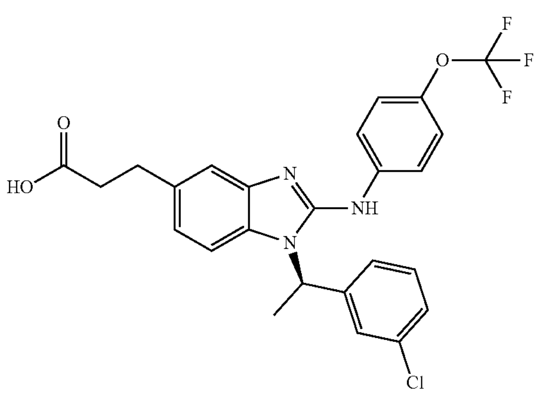 [SMILES: C[C@H](c1cccc(Cl)c1)n1c(Nc2ccc(OC(F)(F)F)cc2)nc2cc(CCC(=O)O)ccc21] | 121.1 |

TABLE 1-continued
IDH1 in vitro enzyme (IDH1R132H) activity IC$_{50}$ test results
| Example | Structure | IDH1 R132H (nM) |
|---|---|---|
| Example 8 | 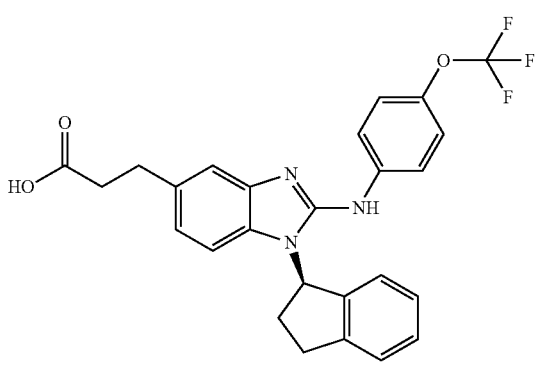 [SMILES: O=C(O)CCc1ccc2c(c1)nc(Nc1ccc(OC(F)(F)F)cc1)n2[C@@H]1CCc2ccccc21] | 2.88 |
| Example 9 | 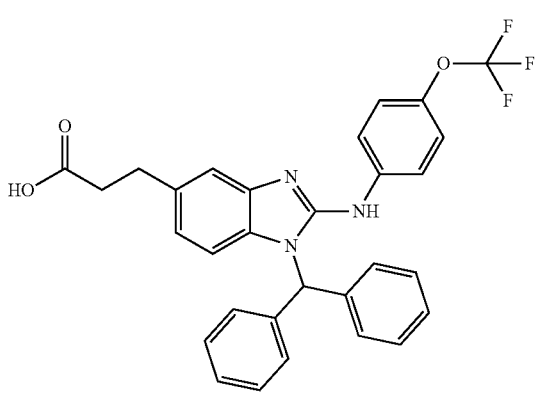 [SMILES: O=C(O)CCc1ccc2c(c1)nc(Nc1ccc(OC(F)(F)F)cc1)n2C(c1ccccc1)c1ccccc1] | 21.9 |
| Example 10 | 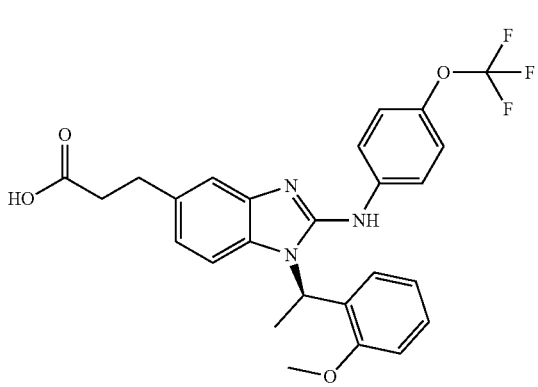 [SMILES: COc1ccccc1[C@@H](C)n1c(Nc2ccc(OC(F)(F)F)cc2)nc2cc(CCC(=O)O)ccc21] | 343.6 |
| Example 11 | 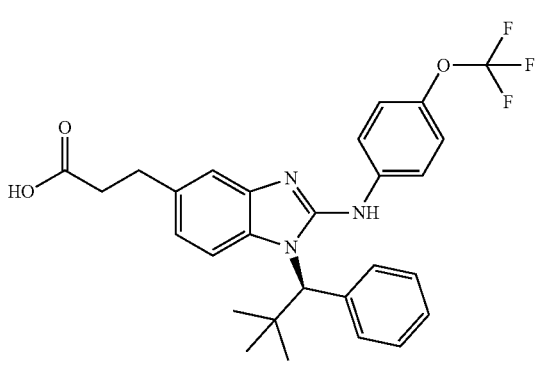 [SMILES: CC(C)(C)[C@H](c1ccccc1)n1c(Nc2ccc(OC(F)(F)F)cc2)nc2cc(CCC(=O)O)ccc21] | 24.5 |

TABLE 1-continued

IDH1 in vitro enzyme (IDH1R132H) activity IC$_{50}$ test results

| Example | Structure | IDH1 R132H (nM) |
|---|---|---|
| Example 12 | (structure) | 15.69 |

TABLE 2

IDH1 in vitro enzyme (IDH1 R132C, WT) activity IC$_{50}$ test results

| Example | Structure | IDH1 R132C (nM) | IDH1 WT (nM) |
|---|---|---|---|
| Example 1 | (structure) | 101.8 | >10000 |
| Example 6 | (structure) | 12.79 | >10000 |

Conclusion: At the enzymatic level, the compounds of the present disclosure have a good inhibitory effect on the mutant IDH1R132H and IDH1R132C, and at the same time have no inhibitory effect on the wild-type IDH protein.

Experimental Example 2: IDH1 Cytological Activity Test

In this study, the compound was incubated with the IDH1 mutant cell line, and the 2HG content in the cell culture supernatant was detected by LC-MS to determine the inhibitory activity of the compound on the IDH1 mutant. IDH1 catalyzes the reduction of isocitrate to α-ketoglutarate (α-KG) in organisms, and the IDH1 mutant further catalyzes the reduction of α-KG to 2-hydroxyglutarate (2HG).

The U87MG-IDH1-R132H cell strain is a stable transfected cell strain that can stably express IDH1-R132H mutant, obtained via screening by transfecting U87MG cells with IDH1-R132H, and the HT1080 cell strain contains an endogenous IDH1-R132C mutant.

The experimental process is as follows:
1) The compound was diluted 3-fold with DMSO and then added to the cell culture plate, at a total of 10 concentrations, double duplicate holes for each concentration. The negative control well contains only DMSO, and the positive control well contained BAY1436032 at a final concentration of 5 μM. The final concentration of DMSO in all wells was 0.5%.

2) The IDH1 mutant cell line was seeded into a cell culture plate containing the compound at a density of 40,000 cells/well. The cells were incubated with the compound in a incubator at 37° C., 5% $CO_2$ for 3 days.

3) After 3 days, 10 μl of cell culture supernatant was taken and diluted 21 folds with 200 μl dd$H_2O$ water to 210 μl and mixed well, from which 50 μl diluted solution was taken and 200 μl precipitant (acetonitrile containing 0.4 μg/ml D-2-hydroxyglutaric acid $^{13}C5$) was added. After centrifugation at 4000 rpm for 10 minutes, 100 μl of supernatant was taken for detecting the content of 2-HG by LC-MS.

4) At the same time, the ATPlite 1 Step kit was used to detect the effect of the compound on the cell viability of the IDH1 mutant cell strain according to the instructions.

5) 2HG content data was used to calculate the percentage of inhibition rate (inhibition rate %) of each concentration of compound against IDH1 mutant by the following calculation formula:

Inhibition rate %=(CPD-ZPE)/(HPE-ZPE)×100% cell viability data was used to calculate the cytotoxicity percentage (cytotoxicity %) of the compound against IDH1 mutant cell strain by the following calculation formula:

Cytotoxicity %=(1-CPD/ZPE)×100%

CPD: signal of compound wells
ZPE: average signal of negative control wells, with 0.5% DMSO instead of compound
HPE: average signal of positive control wells 6) The inhibition rate % and cytotoxicity % were fitted with GraphPad Prism software to the dose-effect curve, to obtain the $IC_{50}$ value of the test compound.

The experimental results are shown in Table 3:

TABLE 3

IDH1 in vitro cell (U87MG) activity $IC_{50}$ test results

| Example | Structure | U87MG IDH1-R132H (nM) |
|---|---|---|
| Example 1 | 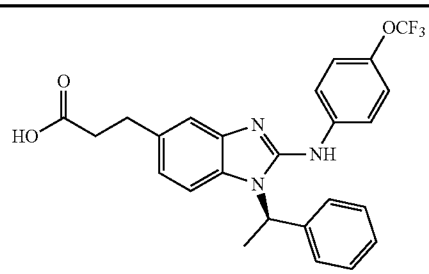 | 92.75 |
| Example 6 | 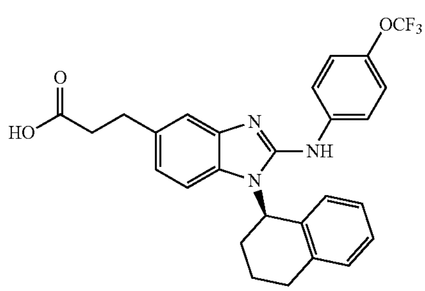 [SMILES: O=C(O)CCc1ccc2c(c1)nc(Nc1ccc(OC(F)(F)F)cc1)n2[C@@H]1CCCc2ccccc21] | 38.25 |

Conclusion: At the cellular level, the compounds of the present disclosure have a good 2-HG inhibitory effect on U87MG brain glioma cells with IDH1R132H mutation.

Experimental Example 3. Evaluation of Pharmacokinetics in Mice

Purpose:

Test the pharmacokinetic parameters of the compound of the present disclosure in mice Experimental Scheme 1) Experimental drug: Example 6;
2) Experimental animals: 8 male CD-1 mice aged 7-10 weeks, divided into 2 groups, 4 in each group;
3) Drug preparation: for the tail vein injection group, an appropriate amount of the drug was weighted, and dissolved in a mixed solvent of DMSO: 20% hydroxypropyl betacyclodextrin (HPbCD)=10:90 to prepare a 0.5 mg/mL solution; for the intragastric administration group, an appropriate amount of the drug was weighted, and dissolved in DMSO: polyoxyethylene castor oil EL (Cremophor EL):5% sulfobutyl cyclodextrin (Captisol)=5:10:85 to prepare a suspension.

Experimental Operation

Animals in group 1 were given a single injection of the drug at a dose of 1 mg/kg and a concentration of 0.5 mg/mL via tail vein, and animals in group 2 were given a compound at a dose of 20 mg/kg and a concentration of 2 mg/mL via gavage. Plasma samples were cross-collected from the animals at 0.0833 (tail vein injection group only), 0.25, 0.5, 1, 2, 4, 6, 8 and 24 hours after administration. The LC-MS/MS method was used to determine the drug concentration in the plasma sample, and the kinetic parameters of the tested drug are shown in Table 4:

TABLE 4

Pharmacokinetic evaluation parameters in mice

Tail vein injection group

| Clearance Cl (mL/min/kg) | Initial concentration $C_0$ (nM) | Volume of distribution Vd (L/Kg) | Half-life $T_{1/2}$ (h) | Area under curve $AUC_{0-last}$ (nM · h) |
|---|---|---|---|---|
| 2.17 | 3541 | 0.690 | 2.90 | 15463 |

Intragastric administration group

| Highest concentration $C_{max}$ (nM) | Time of highest concentration $T_{1/2}$(h) | Area under curve $AUC_{0-last}$ (nM · h) | Bioavailability F (%) |
|---|---|---|---|
| 33350 | 1.00 | 306609 | 99.1 |

Conclusion: Example 6 of the present disclosure has good pharmacokinetic properties in mice.

The invention claimed is:
1. A compound as shown in formula (I),

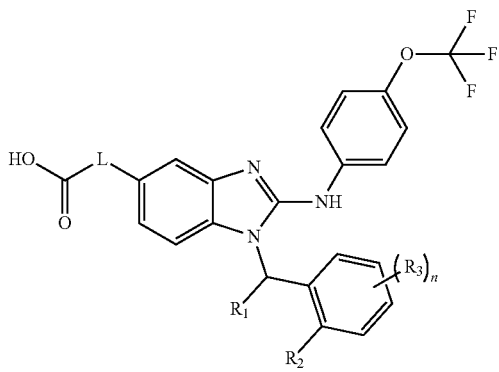

wherein
R₁ is selected from $C_{1-6}$ alkyl, $C_{3-6}$ cycloalkyl and phenyl, the $C_{1-6}$ alkyl, $C_{3-6}$ cycloalkyl and phenyl being optionally substituted with 1, 2 or 3 $R_a$;
R₂ and R₃ are each independently selected from H, F, Cl, Br, I, OH, NH₂, CN, COOH, $C_{1-6}$ alkyl and $C_{1-6}$ alkoxy, the $C_{1-6}$ alkyl and $C_{1-6}$ alkoxy being optionally substituted with 1, 2 or 3 $R_b$;
alternatively, R₁ and R₂ are joined together to form a $C_{4-6}$ cycloalkenyl optionally substituted with 1, 2 or 3 $R_c$;
L is selected from —CH₂CH₂— and —$C_{3-6}$ cycloalkyl-CH₂—;
n is selected from 1, 2 and 3; and
$R_a$, $R_b$, and $R_c$ are each independently selected from F, Cl, Br, I, OH, NH₂, CN, COOH, and Me;
or an isomer thereof, or a pharmaceutically acceptable salt thereof.

2. The compound or an isomer thereof or a pharmaceutically acceptable salt thereof according to claim 1, wherein R₁ is selected from $C_{1-3}$ alkyl, cyclopropanyl and phenyl, the $C_{1-3}$ alkyl, cyclopropanyl and phenyl being optionally substituted with 1, 2 or 3 $R_a$.

3. The compound or an isomer thereof or a pharmaceutically acceptable salt thereof according to claim 2, wherein R₁ is selected from CH₃, CH₂F, CHF₂, CF₃, CH₂CH₃, CH₂CF₃, CH₂CH₂CH₃, C(CH₃)₃,

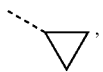,

CH(CH₃)₂ and

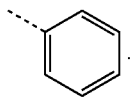.

4. The compound or an isomer thereof or a pharmaceutically acceptable salt thereof according to claim 1, wherein R₂ and R₃ are each independently selected from H, F, Cl, Br, I, OH, NH₂, CN, COOH, $C_{1-3}$ alkyl and $C_{1-3}$ alkoxy, the $C_{1-3}$ alkyl and $C_{1-3}$ alkoxy being optionally substituted with 1, 2 or 3 $R_b$.

5. The compound or an isomer thereof or a pharmaceutically acceptable salt thereof according to claim 4, wherein R₂ and R₃ are each independently selected from H, F, Cl, Br, I, OH, NH₂, CN, COOH, CH₃ and CH₃O, the CH₃ and CH₃O being optionally substituted with 1, 2 or 3 $R_b$.

6. The compound or an isomer thereof or a pharmaceutically acceptable salt thereof according to claim 5, wherein R₂ and R₃ are each independently selected from H, F, Cl, Br, I, OH, NH₂, CN, COOH, CH₃, CH₂F, CHF₂, CF₃ and OCH₃.

7. The compound or an isomer thereof or a pharmaceutically acceptable salt thereof according to claim 1, wherein L is selected from —CH₂CH₂— and

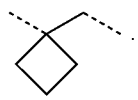.

8. The compound or an isomer thereof or a pharmaceutically acceptable salt thereof according to claim 1, wherein the structural unit

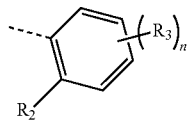

is selected from

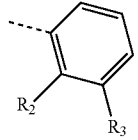 and 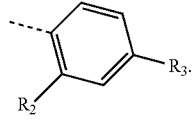.

9. The compound or an isomer thereof or a pharmaceutically acceptable salt thereof according to claim 8, wherein the structural unit

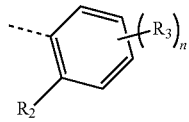

is selected from

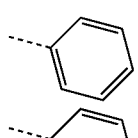, 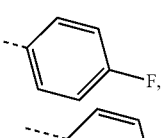,

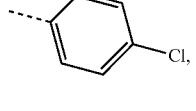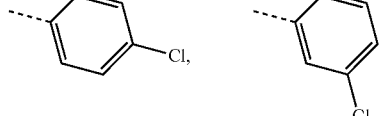

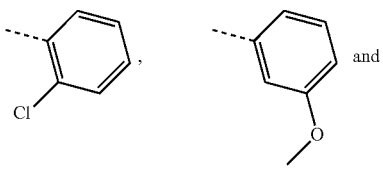, 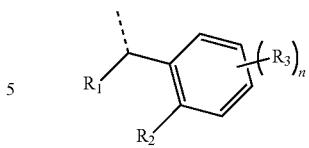
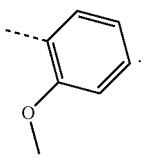.
10. The compound or an isomer thereof or a pharmaceutically acceptable salt thereof according to claim 1, wherein the structural unit
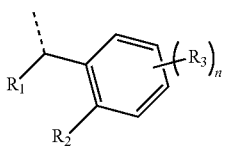
is selected from
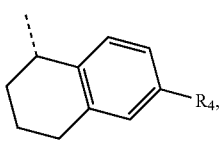, 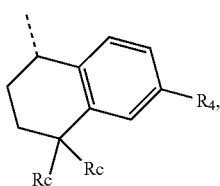,
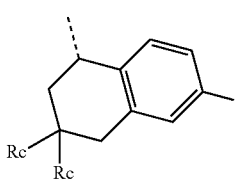, 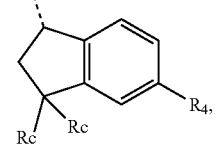,
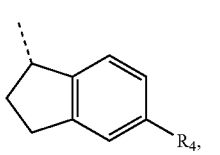, 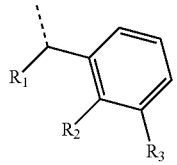 and
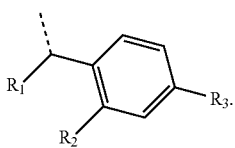.
11. The compound or an isomer thereof or a pharmaceutically acceptable salt thereof according to claim 10, wherein the structural unit
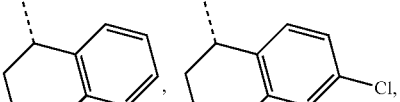
is selected from
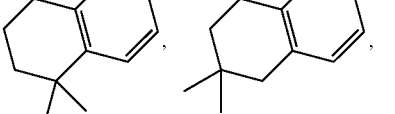
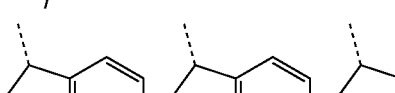
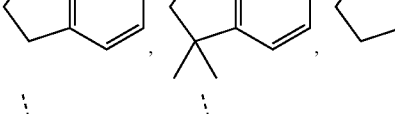
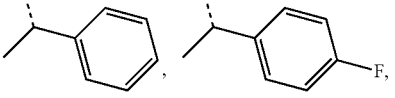
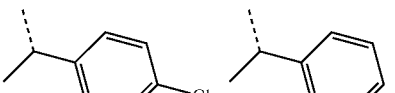
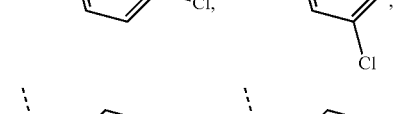
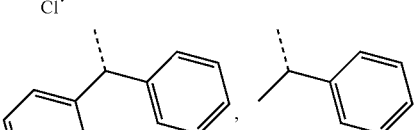
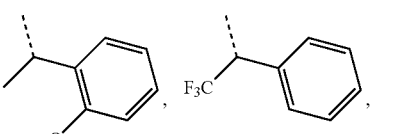
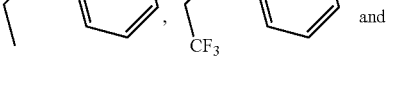

-continued

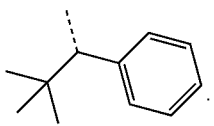

12. The compound or an isomer thereof or a pharmaceutically acceptable salt thereof according to claim 1, which is selected from

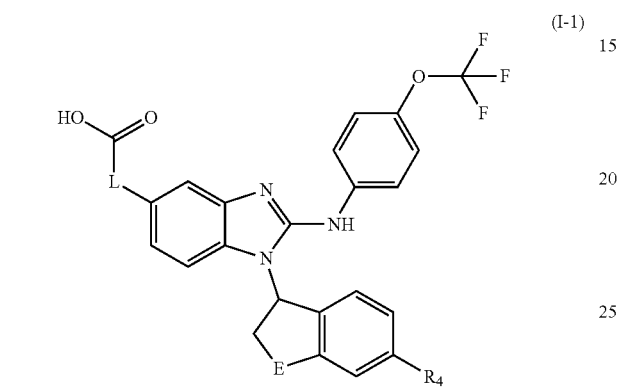
(I-1)

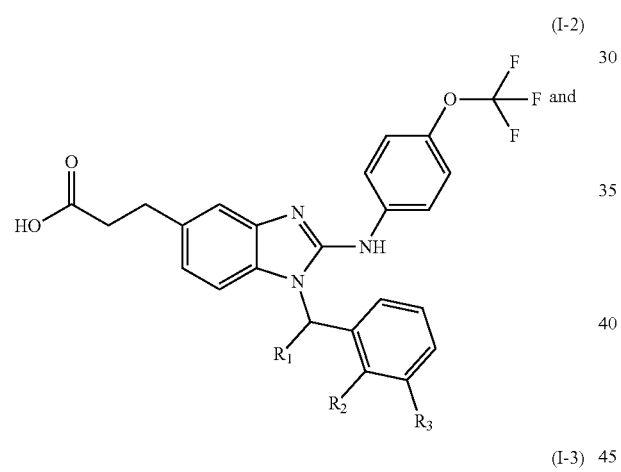
(I-2)

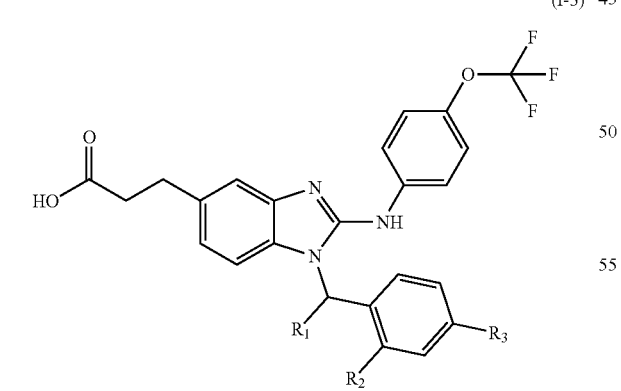
(I-3)

wherein

E is selected from —CH$_2$—, —CH$_2$CH$_2$—, —C(CH$_3$)$_2$— and —C(CH$_3$)$_2$CH$_2$—;

L is selected from —CH$_2$CH$_2$— and

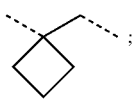
;

R$_1$ is as defined in any one of claims 2 to 3; and

R$_2$ and R$_3$ are as defined in any one of claims 4 to 6.

13. The compound or an isomer thereof or a pharmaceutically acceptable salt thereof according to claim 12, which is selected from

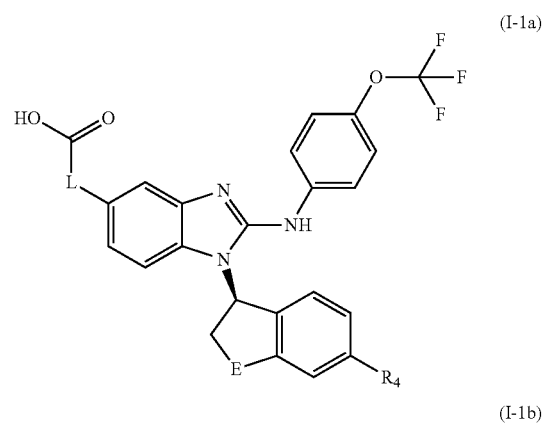
(I-1a)

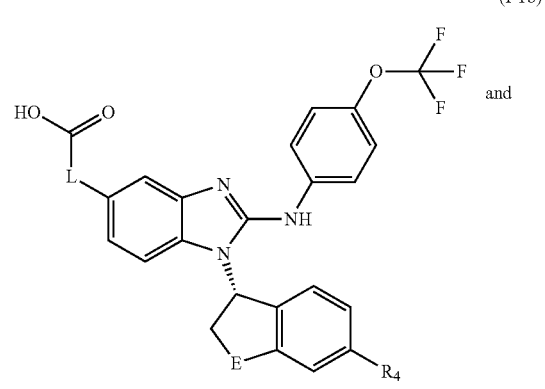
(I-1b) and

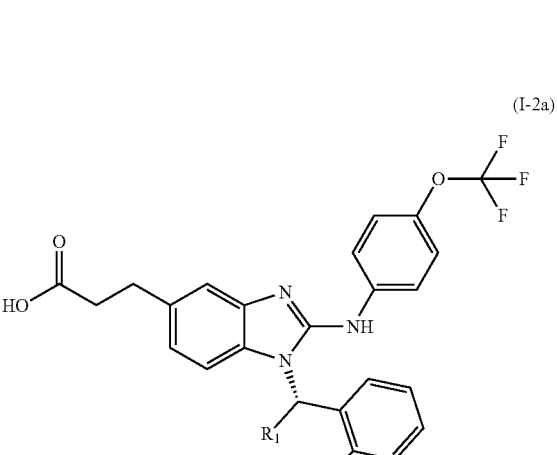
(I-2a)

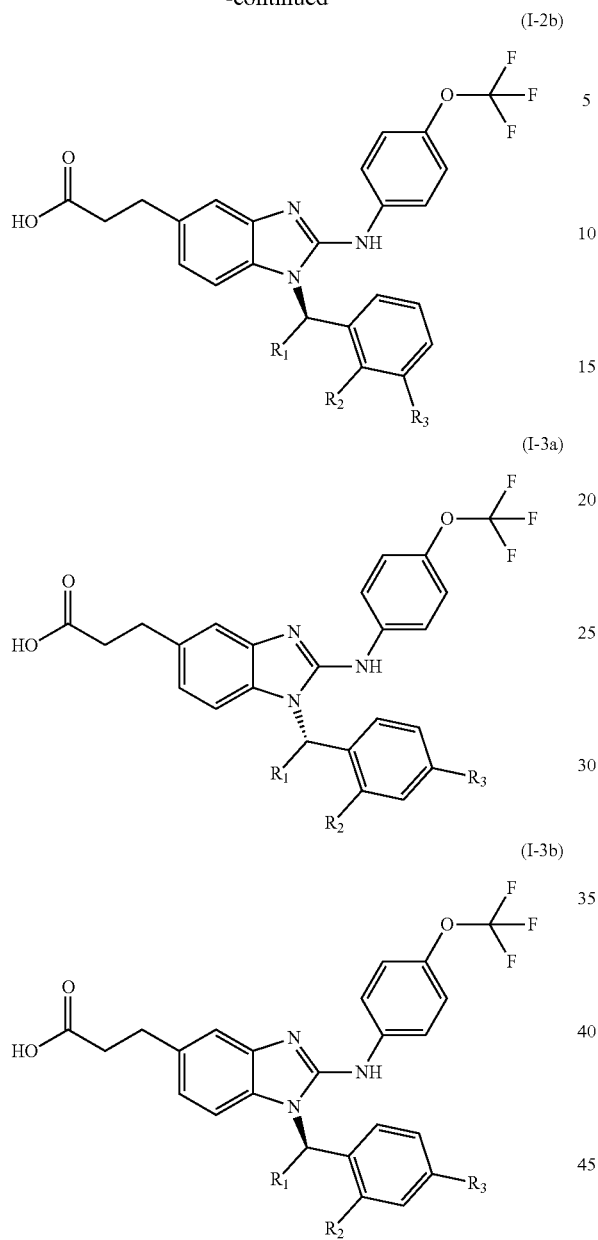
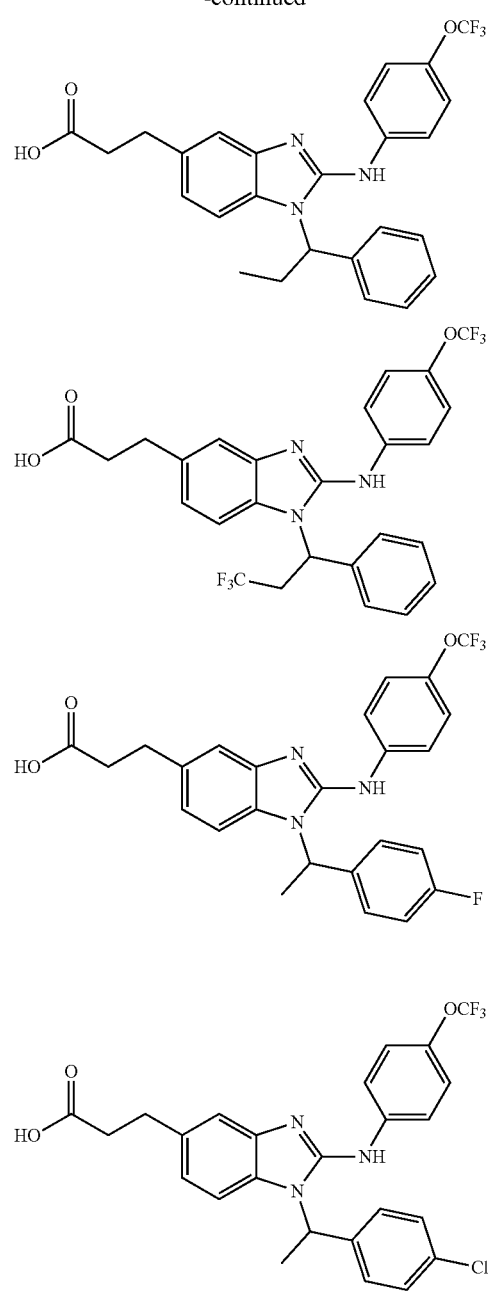
wherein
E, L, R₁, R₂ and R₃ are as defined in claim 12.
14. A compound as shown in the following formula, which is selected from
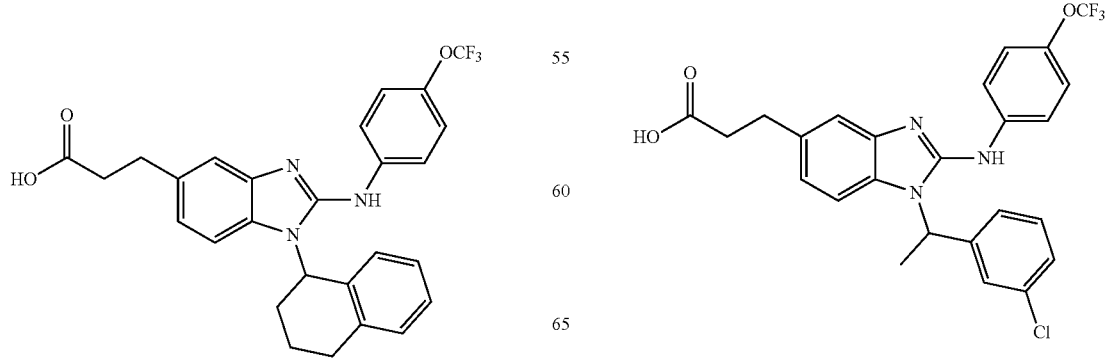

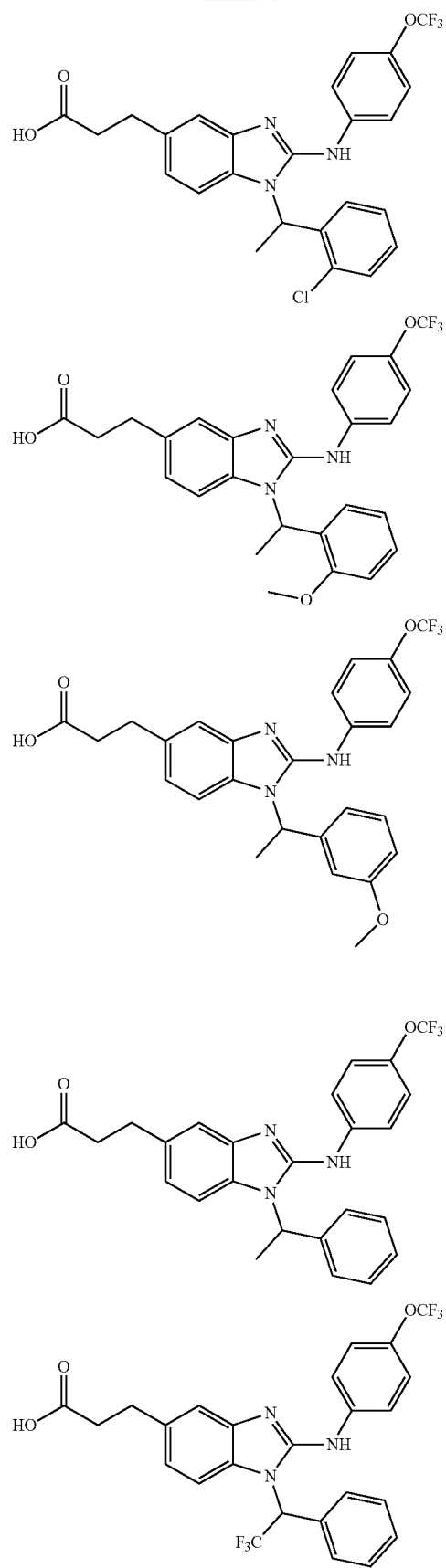
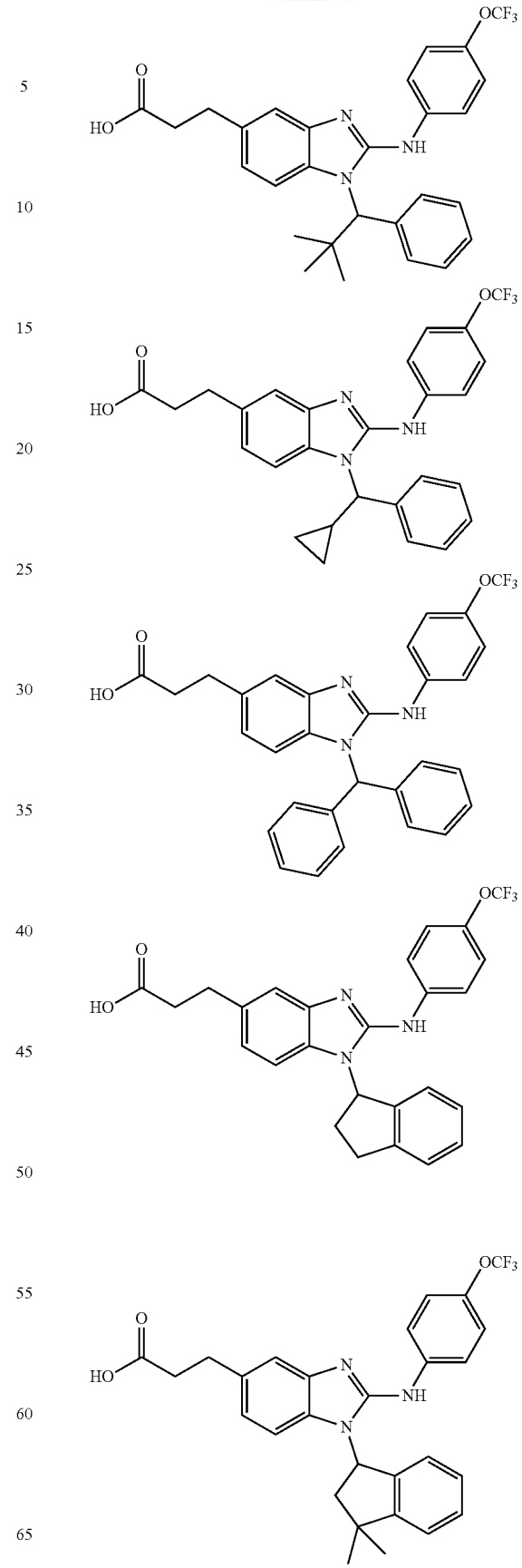

-continued
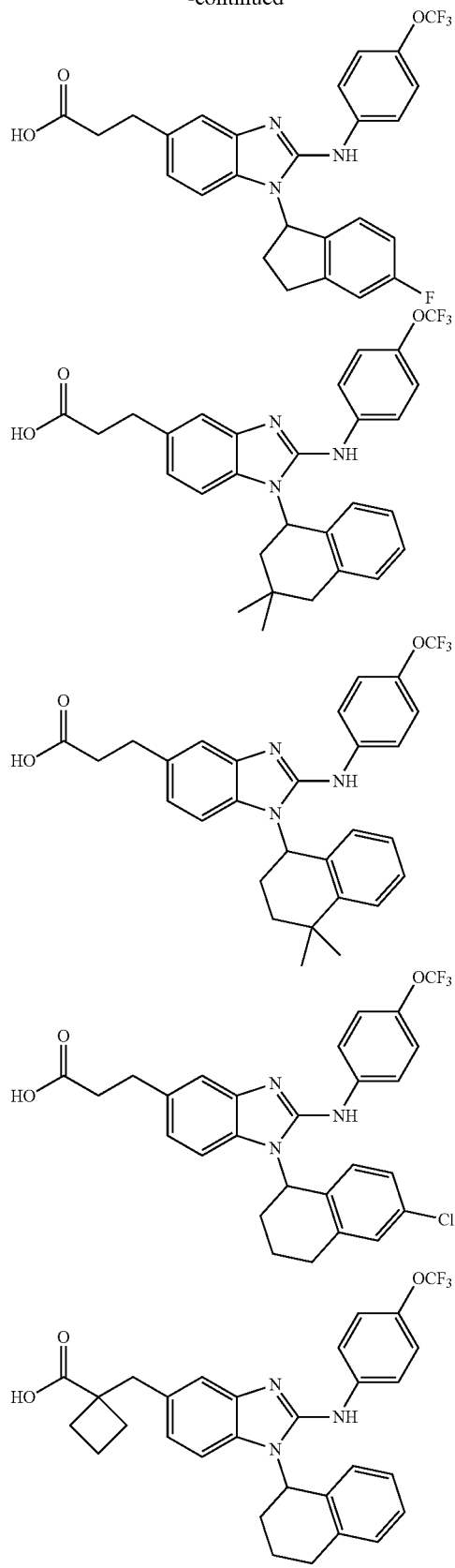
or an isomer thereof, or a pharmaceutically acceptable salt thereof.
15. The compound or an isomer thereof or a pharmaceutically acceptable salt thereof according to claim 14, which is selected from
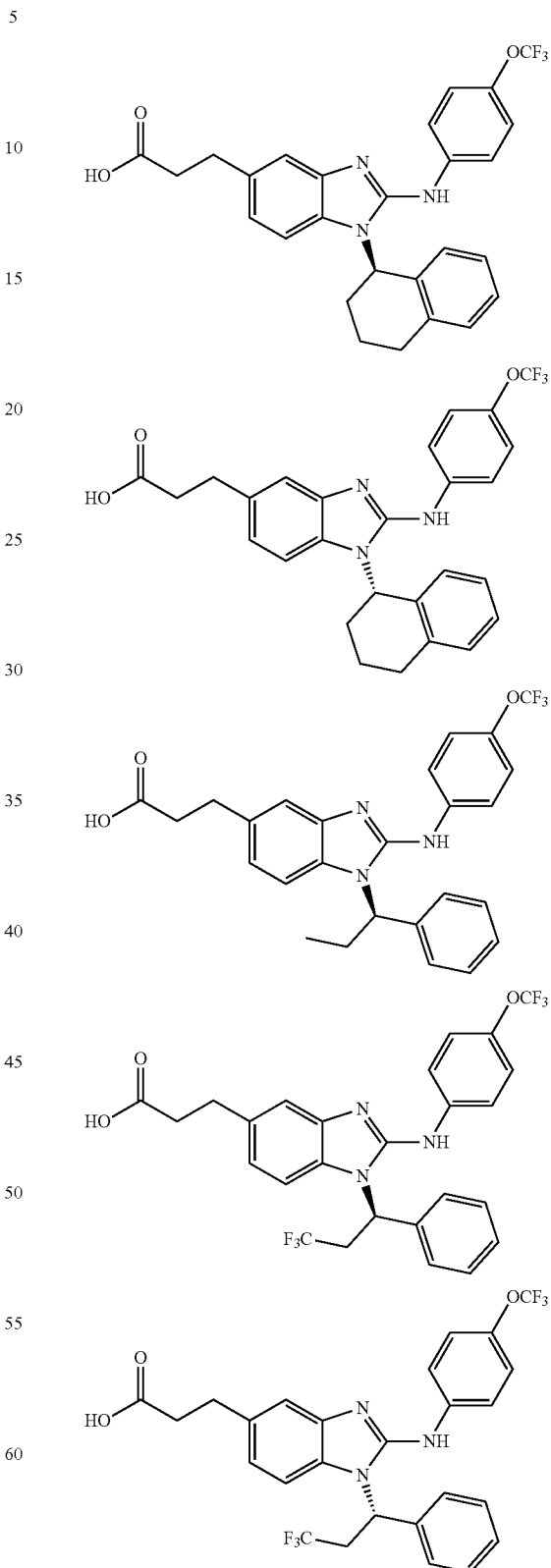
and

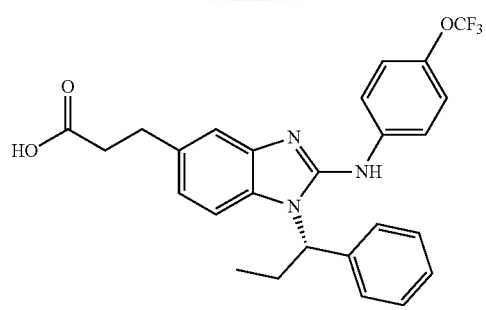
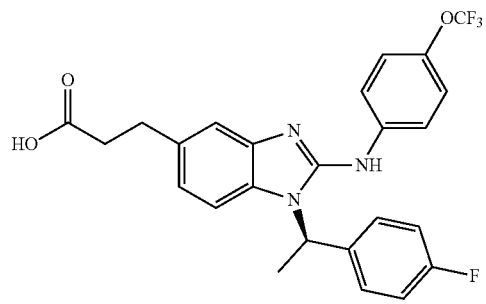
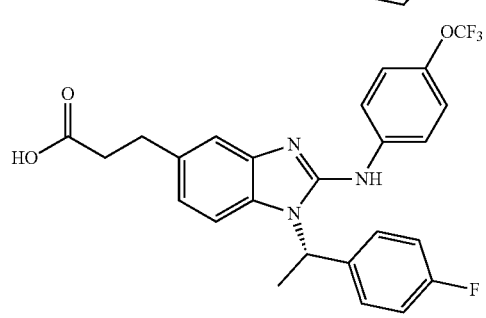
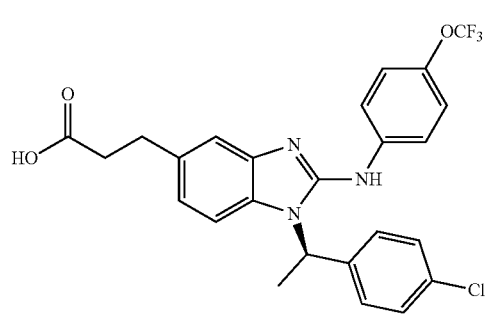
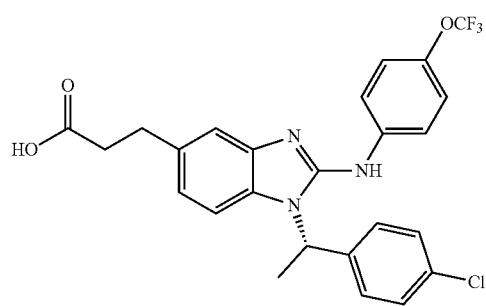
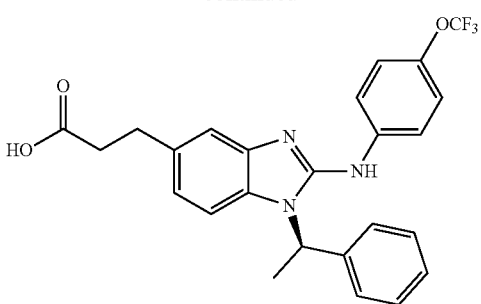
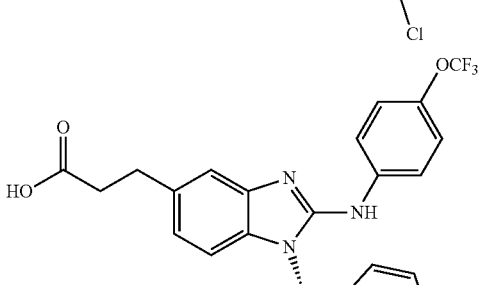
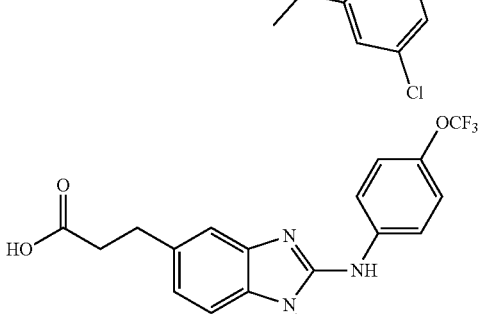
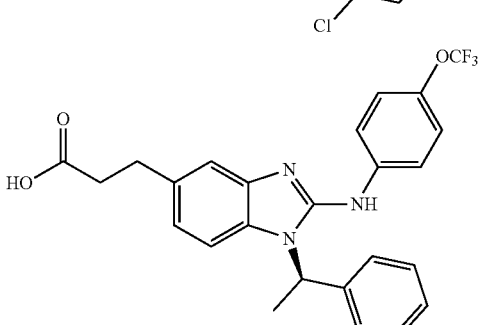
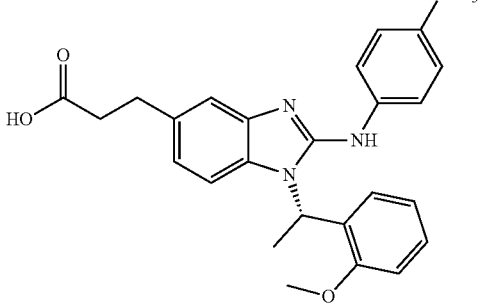

89
-continued
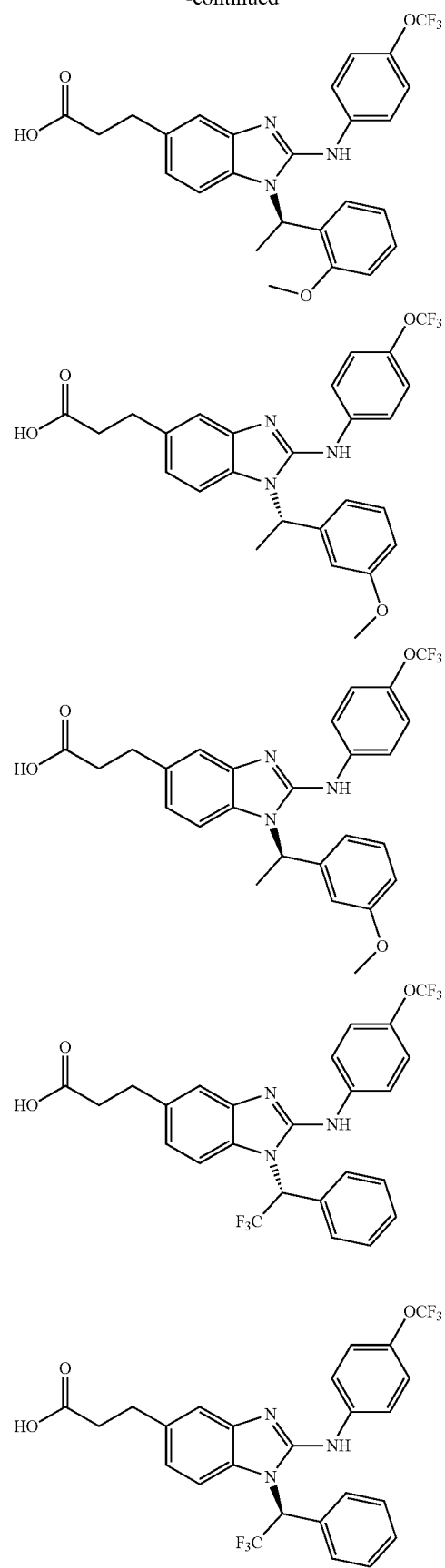
90
-continued
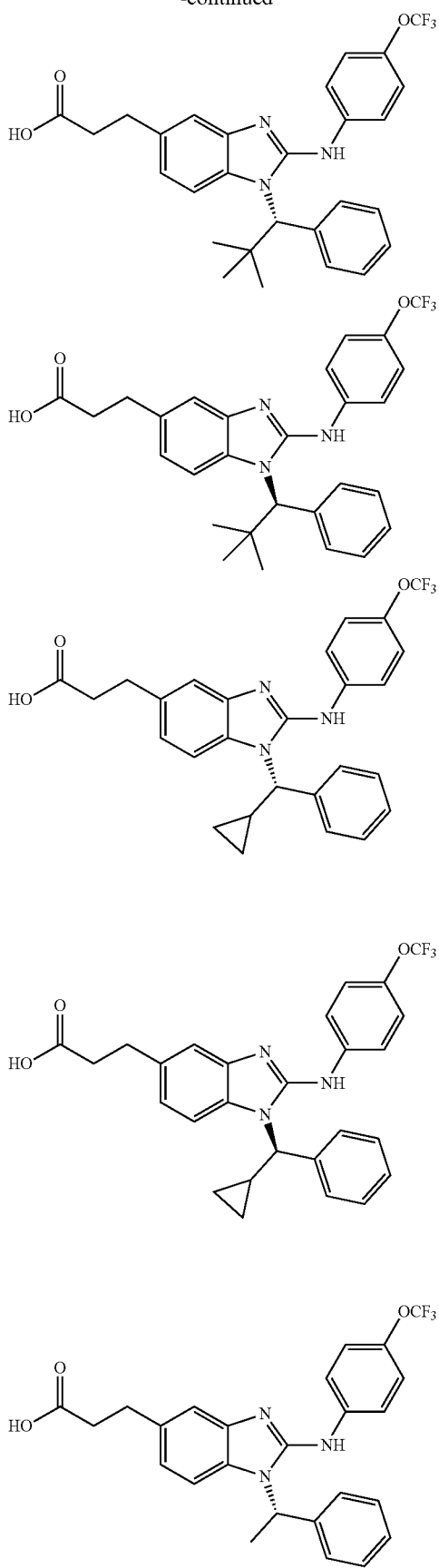

91
-continued
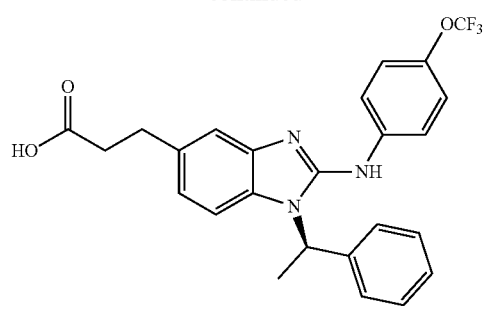
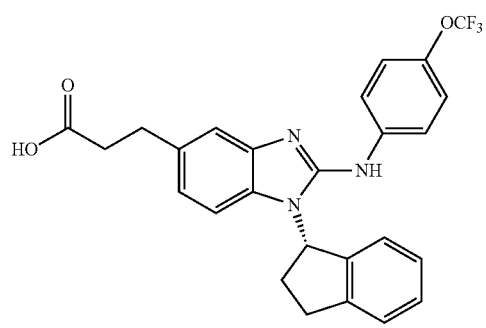
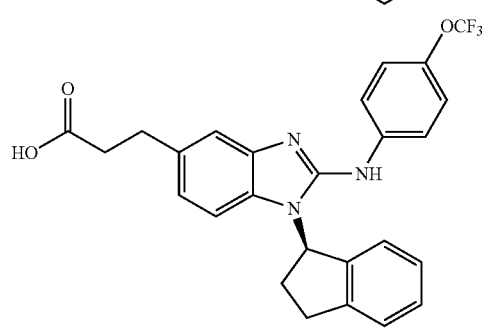
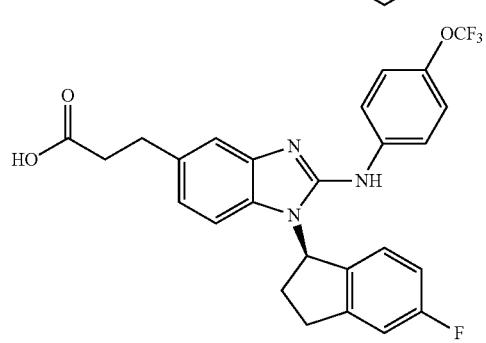
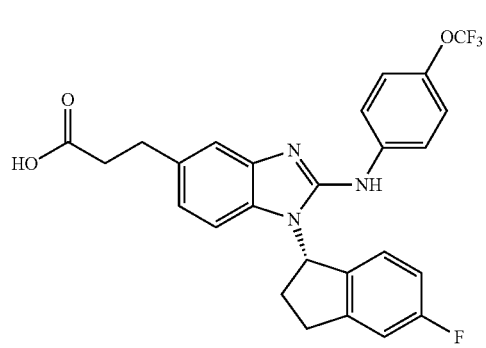
92
-continued
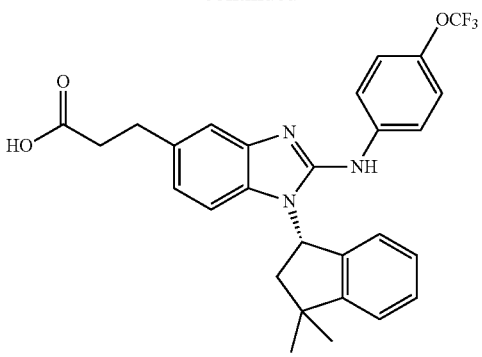
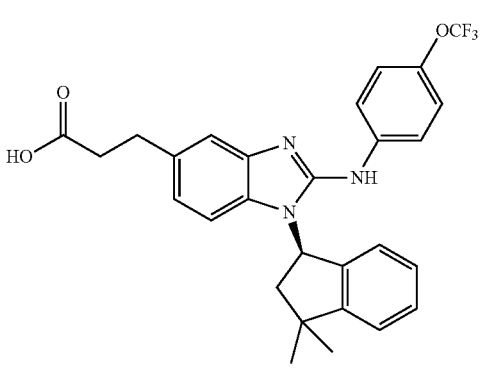
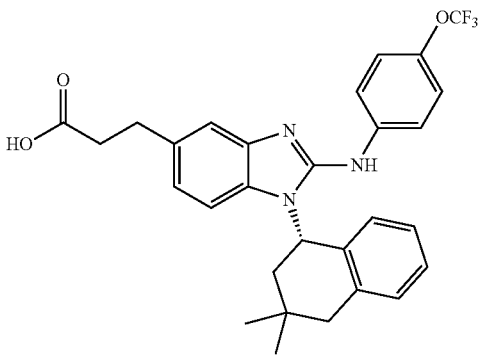
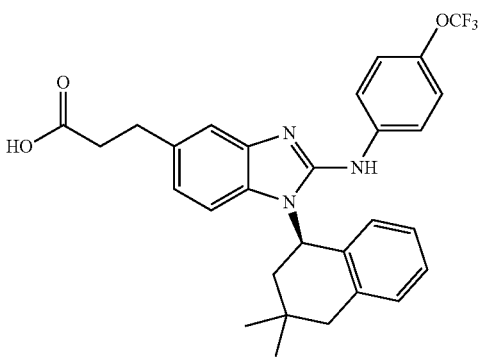

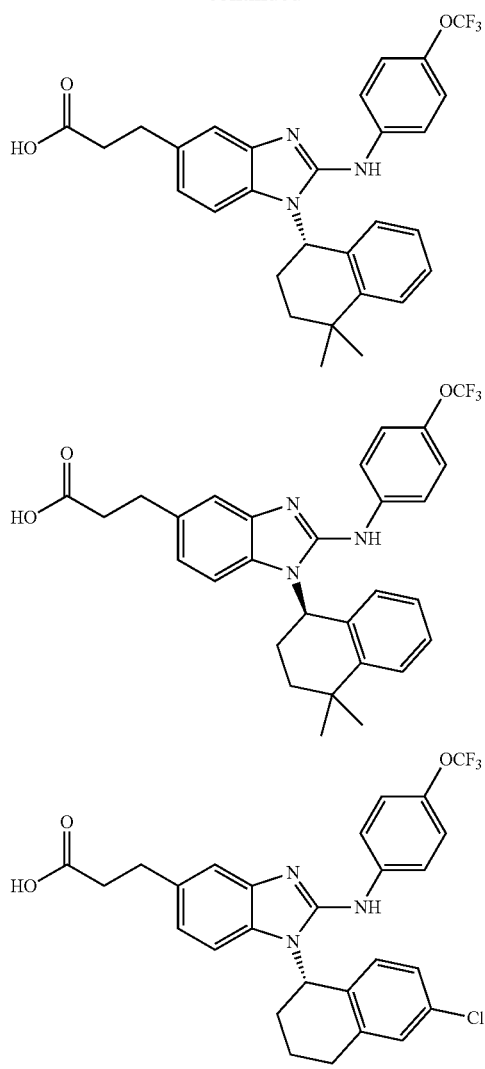
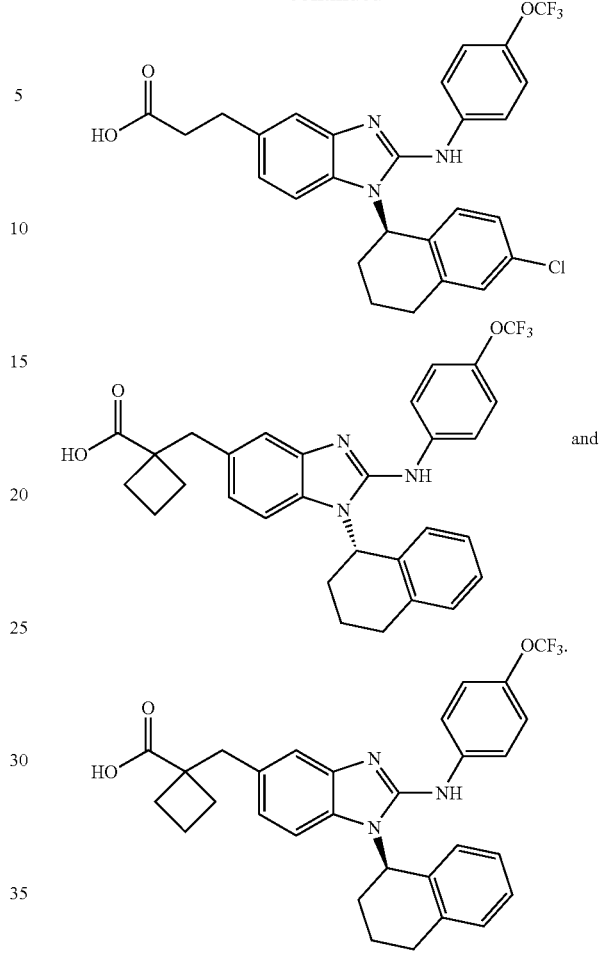
16. A method of treating a tumor disease related to IDH1 mutations, comprising administering the compound or an isomer thereof or a pharmaceutically acceptable salt thereof according to claim 1 to a subject in need thereof.
* * * * *